(12) United States Patent
Hassibi et al.

(10) Patent No.: US 8,048,626 B2
(45) Date of Patent: Nov. 1, 2011

(54) MULTIPLEX Q-PCR ARRAYS

(75) Inventors: Arjang Hassibi, Austin, TX (US);
Babak Hassibi, San Marino, CA (US);
Haris Vikalo, Pasadena, CA (US)

(73) Assignee: California Institute of Technology,
Pasadena, CA (US)

( * ) Notice: Subject to any disclaimer, the term of this patent is extended or adjusted under 35 U.S.C. 154(b) by 653 days.

(21) Appl. No.: 11/829,861

(22) Filed: Jul. 27, 2007

(65) Prior Publication Data

US 2008/0176757 A1   Jul. 24, 2008

Related U.S. Application Data

(60) Provisional application No. 60/834,051, filed on Jul. 28, 2006.

(51) Int. Cl.
*C12Q 1/68* (2006.01)
*C07H 21/04* (2006.01)

(52) U.S. Cl. .............. 435/6.11; 435/6.12; 536/24.3

(58) Field of Classification Search .............. None
See application file for complete search history.

(56) References Cited

U.S. PATENT DOCUMENTS

| | | |
|---|---|---|
| 4,562,157 A | 12/1985 | Lowe et al. |
| 4,711,955 A | 12/1987 | Ward et al. |
| 4,994,373 A | 2/1991 | Stavrianopoulos et al. |
| 5,082,830 A | 1/1992 | Brakel et al. |
| 5,328,824 A | 7/1994 | Ward et al. |
| 5,449,767 A | 9/1995 | Ward et al. |
| 5,476,928 A | 12/1995 | Ward et al. |
| 5,491,063 A | 2/1996 | Fisher et al. |
| 5,571,673 A | 11/1996 | Picone |
| 5,573,906 A | 11/1996 | Bannwarth et al. |
| 5,632,957 A | 5/1997 | Heller et al. |
| 5,656,493 A | 8/1997 | Mullis et al. |
| 5,744,305 A | 4/1998 | Fodor et al. |
| 5,807,522 A | 9/1998 | Brown et al. |
| 5,871,928 A | 2/1999 | Fodor et al. |
| 5,974,164 A | 10/1999 | Chee |
| 6,025,601 A | 2/2000 | Trulson et al. |
| 6,040,193 A | 3/2000 | Winkler et al. |
| 6,048,690 A | 4/2000 | Heller et al. |

(Continued)

FOREIGN PATENT DOCUMENTS

EP   02360691 B1   5/1997

(Continued)

OTHER PUBLICATIONS

Gunderson, et al.-Decoding Randomly Ordered DNA Arrays. Genome Res. 14:870-877, 2004.

(Continued)

*Primary Examiner* — Samuel Woolwine
(74) *Attorney, Agent, or Firm* — Milstein Zhang & Wu LLC; Joseph B. Milstein

(57) ABSTRACT

This invention provides methods and systems for measuring the concentration of multiple nucleic acid sequences in a sample. The nucleic acid sequences in the sample are simultaneously amplified, for example, using polymerase chain reaction (PCR) in the presence of an array of nucleic acid probes. The amount of amplicon corresponding to the multiple nucleic acid sequences can be measured in real-time during or after each cycle using a real-time microarray. The measured amount of amplicon produced can be used to determine the original amount of the nucleic acid sequences in the sample.

20 Claims, 23 Drawing Sheets

U.S. PATENT DOCUMENTS

| | | | |
|---|---|---|---|
| 6,054,270 | A | 4/2000 | Southern |
| 6,110,426 | A | 8/2000 | Shalon et al. |
| 6,124,102 | A | 9/2000 | Fodor et al. |
| 6,174,670 | B1 | 1/2001 | Wittwer et al. |
| 6,225,625 | B1 | 5/2001 | Pirrung et al. |
| 6,261,776 | B1 | 7/2001 | Pirrung et al. |
| 6,291,183 | B1 | 9/2001 | Pirrung et al. |
| 6,319,958 | B1 | 11/2001 | Johnson et al. |
| 6,465,175 | B2 | 10/2002 | Horn et al. |
| 6,600,996 | B2 | 7/2003 | Webster et al. |
| 6,610,482 | B1 | 8/2003 | Fodor et al. |
| 6,750,963 | B2 | 6/2004 | Sampas |
| 6,814,934 | B1 | 11/2004 | Higuchi |
| 7,064,197 | B1 | 6/2006 | Rabbani et al. |
| 2002/0150917 | A1 | 10/2002 | Weidenhammer et al. |
| 2006/0088844 | A1* | 4/2006 | Xu .......... 435/6 |
| 2008/0085839 | A1* | 4/2008 | Klapproth .......... 506/12 |

FOREIGN PATENT DOCUMENTS

| | | |
|---|---|---|
| WO | WO 00/79009 A2 | 12/2000 |
| WO | WO 01/86001 A1 | 11/2001 |
| WO | WO 00/79009 A3 | 1/2002 |
| WO | WO 02/30946 A1 | 4/2002 |
| WO | WO 03/062791 A2 | 7/2003 |
| WO | WO 03/062791 A3 | 7/2003 |

OTHER PUBLICATIONS

Hall. Biosensors. Pretice-Hall. Englewood Cliffs, NJ. 1991. (Table of Contents only).

Han, et al. Quantum-dot-tagged microbeads for multiplexed optical coding of biomolecules. Nature Biotechnology 19, 631-635 (2001).

Hassibi, et al. A stochastic model and simulation algorithm for polymerase chain reaction (PCR) systems. Proc of Workshop on Genomics Signal Processing and Statistics. 2004: 1-4.

Lockhart, et al. Multiplex metallica. Nat Biotechnol. Dec. 2001;19(12):1122-3.

Michael, et al. Randomly Ordered Addressable High-Density Optical Sensor Arrays. Anal. Chem., 70 (7), 1242-1248, 1998.

Petersson, et al. A review of the parameter estimation problem of fitting positive exponential sums to empirical data. Technical Report IMa-TOM-1997-08, Department of Mathematics and Physics. Malardalen University, Sweden. 1997: 1-29.

Schena. Microarray Analysis, Wiley, New York, 2003. (Table of Contents only).

Stolovitzky, et al. Efficiency of DNA replication in the polymerase chain reaction. Proc Natl Acad Sci USA. 1996; 93: 12947-52.

Wang, et al. Estimation of the mutation rate during error-prone polymerase chain reaction. J Comput Biol. 2000; 7(1-2): 143-58.

Wittwer, et al. Continuous fluorescence monitoring of rapid cycle DNA amplification Biotechniques. Jan. 1997;22(1):130-8.

Zhu, et al. Protein chip technology. Current Opinion in Chemical Biology. 2003; 7: 55-63.

Cady, et al. Real-time PCR detection of Listeria monocytogenes using an integrated microfluidics platform. Sensors and Actuators B: Chemical. 2005; 107: 332-341.

Ginzinger. Gene quantification using real-time quantitative PCR: an emerging technology hits the mainstream. Exp Hematol. 2002; 30(6): 503-12.

Giordano, et al. Distinct transcriptional profiles of adrenocortical tumors uncovered by DNA microarray analysis. Am J Pathol. 2003; 162(2):521-531.

\* cited by examiner

Block Diagram of QPCR System

MULTIPLEX Q-PCR ARRAYS

CROSS-REFERENCE

This application claims priority to U.S. Provisional Application No. 60/834,051, filed Jul. 28, 2006, which is incorporated herein by reference in its entirety.

BACKGROUND OF THE INVENTION

Nucleic acid target amplification assays such as polymerase chain reaction process (PCR), in principle, amplify and replicate specific sequences of nucleic acids of a DNA template in vitro. These assays have become a powerful tool in molecular biology and genomics, since they can increase the number of copies of target molecules with great specificity. It is of great interest to efficiently multiplex the amplification process and thus allow for multiple target amplification and quantification.

Currently, various homogeneous (closed-tube) assays are available for PCR. These assays detect the target amplicons (i.e., Quantitative PCR or QPCR). Nevertheless, the number of different nucleic acid sequences that can be simultaneously amplified and detected is very limited. Typically, an individual reaction chamber (or well) where the target is amplified and detected contains only a single amplicon. Multiplexed QPCR, defined as the process of amplifying and detecting a plurality of nucleic acid sequences simultaneously in a single reaction chamber, is generally practical only for a small number of amplicons.

PCR relies on an enzymatic replication process in each of its temperature-regulated cycles (typically, 30-40). A PCR cycle typically consists of three distinct phases: denaturing, annealing, and extension. Ideally, at the end of the extension phase, there are twice as many double-stranded target DNA fragments as there were at the beginning of the cycle. This implies an exponential growth of the amount of the target DNA as one proceeds through the cycles. However, practical issues affect the replication process adversely and the efficiency of PCR, defined as the probability of generating a replica of each template molecule, is usually smaller than the desired factor of two.

Quantification of the amplified targets in PCR is typically based on measuring the light intensity emanating from fluorescent reporter molecules incorporated into the double-stranded DNA copies of the target. The measured light intensity is an indication of the actual number of the amplified targets. Some of the commonly used probes are SYBR Green, hybridization, and TaqMan probes. SYBR Green I is a dye whose fluorescence increases significantly upon binding to (intercalating) double-stranded DNA. SYBR Green is non-discriminatory and will bind to non-specific byproducts of PCR (such as the primer-dimers). For this reason, special attention needs to be paid to optimizing the conditions of PCR with SYBR Green reporters. Hybridization probes are specific to the target DNA sequence. A hybridization probe typically consists of two short probe sequences, one labeled with a fluorescence resonance energy transfer donor and the other with an acceptor dye. The two probe sequences can be designed such that they hybridize next to each other on the target sequence; the co-location of the donor and the acceptor initiates energy transfer and, therefore, the change in their respective light intensities indicates successful replication of the target. The TaqMan probes are also specific to the target sequence, and are designed so that they contain a fluorescent dye in the vicinity of a quenching dye. Where the TaqMan probe hybridizes to the template, and the template is replicated, the TaqMan probe is degraded by the exo activity of the polymerase, separating the fluorescent dye from the quenching dye, resulting in an increased fluorescent signal.

In Q-PCR, fluorescent signal is measured at the end of each temperature cycle. The measured light intensities create a reaction profile, which can be plotted against the number of cycles and used to determine the concentration of the nucleic acid sequence that was amplified.

Attempts at employing QPCR for the simultaneous amplification and detection of many target amplicons in a single well are plagued with practical issues that present obstacles to achieving a truly multiplexed Q-PCR. A common approach used is to divide the biological sample of interest into equal-sized quantities which are then mechanically delivered into separate wells (typically, 96, 192, or 384). This type of sample splitting reduces the amount of material in each individual amplification well, creating issues of sample size, and necessitating precise sample distribution across the wells.

On the other hand, high-throughput screenings of multiple target analytes in biological samples is typically obtained by exploiting the selective binding and interaction of recognition probes in massively-parallel affinity-based biosensors, such as microarrays. Gene expression microarrays, for example are widely used microarray platforms. These systems measure the expression level of thousands of genes simultaneously.

To increase the quality of microarray data, real-time microarray (RT-μArray) systems have been developed. (see U.S. patent application Ser. No. 11/758,621). These systems can evaluate the abundance of a plurality of target analytes in the sample by real-time detection of target-probe binding events. To achieve this, RT-μArrays employ a detection scheme that is a major departure from the techniques typically used in conventional fluorescent-based microarrays and other extrinsic reporter-based biosensors assays. In the latter, the detection of captured analytes is carried out after the hybridization (incubation) step. This is due to the characteristics of the assays used therein, which require removing the solution during the fluorescent and reporter intensity measurements that are done either by scanning and/or various other imaging techniques. This limitation is due in part to the high concentration in solution of unbound labeled species which can overwhelm the target-specific signal from the captured targets. Furthermore, when the hybridization is ceased and the solution is taken away from array surface, washing artifacts typically occur which can make the analysis of the data challenging.

Thus, while Q-PCR provides a convenient and accurate method for measuring the amount of nucleic acid sequences in a sample, it is limited to a single sequence or a small number of sequences in a single fluid volume. And while microarray technology provides for measuring over hundreds of thousands of sequences simultaneously, conventional arrays are not amenable to the type of detection required for practical multiplexed Q-PCR. Thus there exists a strong need for methods and systems for performing multiplex Q-PCR to accurately measure the presence and/or amount of multiple nucleic acid sequences in a single fluid volume in a single amplification reaction.

SUMMARY OF THE INVENTION

One aspect of the invention is a method comprising; performing a nucleic acid amplification on two or more nucleotide sequences to produce two or more amplicons in a fluid wherein the array comprises a solid surface with a plurality of nucleic acid probes at independently addressable locations;

and measuring the hybridization of the amplicons to the two or more nucleic acid probes while the fluid is in contact with the array to obtain an amplicon hybridization measurement. In some embodiments the invention further comprises using the amplicon hybridization measurement to determine the concentration of the amplicons in the fluid. In some embodiments the invention further comprises using the amplicon hybridization measurement to determine the original amount of nucleotide sequences.

In some embodiments the concentration of amplicon is measured during or after some, but not all of the amplification cycles. In some embodiments the concentration of amplicon is measured during or after each of the amplification cycles. In some embodiments the concentration of amplicon is measured during on average every 2, 3, 4, 5, 6, 7, 8, 9 or 10 amplification cycles. In some embodiments the nucleic acid amplification is polymerase chain reaction (PCR), and an amplification cycle corresponds with a temperature cycle. In some embodiments at least some temperature cycles comprise (a) a probe hybridization phase at one temperature, and (b) primer annealing phase at a higher temperature than the probe hybridization temperature. In some embodiments at least some temperature cycles comprise 4 or more temperature phases, wherein one or more of the phases is a probe hybridization phase wherein the hybridization of amplicons to the nucleic acid probes is measured. In some embodiments the temperature is changed during probe hybridization phase. In some embodiments the method comprises two or more hybridization phases, carried out at different temperatures. In some embodiments at least some temperature cycles comprise a first denaturing phase, a probe hybridization phase, a second denaturing phase, a primer annealing phase, and an extension phase.

In some embodiments the array is in contact with the fluid during the amplification.

In some embodiments the two or more nucleotide sequences are not only two complementary nucleotide sequences.

In some embodiments the amplification is an isothermal amplification. In some embodiments the amplification is a linear amplification.

In some embodiments the measuring of hybridization comprises measuring the kinetics of hybridization of the amplicons to the nucleic acid probes. In some embodiments the measuring of the kinetics of hybridization comprises measuring a light signal at multiple time points.

In some embodiments the amplicons comprise a quencher. In some embodiments primers are used to create the amplicons and the primers comprise a quencher. In some embodiments one of the primers in a primer pair comprises a quencher. In some embodiments both of the primers in a primer pair comprise a quencher. In some embodiments quenchers are incorporated into the amplicons as they are formed. In some embodiments d-NTP's are used to make the amplicons, and one or more of the d-NTP's used to make the amplicon comprises a quencher.

In some embodiments the amplicon hybridization measurement is performed by measuring fluorescence from fluorescent moieties attached to the solid surface. In some embodiments the fluorescent moieties are covalently attached to the nucleic acid probes. In some embodiments the fluorescent moieties are attached to the substrate and are not covalently attached to the nucleic acid probes. In some embodiments the amplicons comprise quenchers, and the measuring of hybridization is performed by measuring a decrease in fluorescence due to hybridization of amplicons to the nucleic acid probes. In some embodiments the array comprises at least about 3, 4, 5 10, 50, 100, 100, 1000, 10,000, 100,000, or 1,000,000 nucleic acid probes. In some embodiments the nucleic acid probe comprises a PNA or LNA probe.

One aspect of the invention is a method comprising: (a) providing an array comprising a solid support having a surface and a plurality of different probes, the different probes immobilized to the surface at different addressable locations, each addressable location comprising a fluorescent moiety; (b) performing PCR amplification on a sample comprising a plurality of nucleotide sequences; the PCR amplification carried out in a fluid, wherein: (i) a PCR primer for each nucleic acid sequence comprises a quencher; and (ii) the fluid is in contact with the probes, whereby amplified molecules can hybridize with probes, thereby quenching signal from the fluorescent moiety; (c) detecting the signals from the fluorescent moieties at the addressable locations over time; (d) using the signals detected over time to determine the amount of amplified molecules in the fluid; and (e) using the amount of amplified molecules in the fluid to determine the amount of the nucleotide sequences in the sample.

In some embodiments the determining of the amount of amplified molecules is performed during or after multiple temperature cycles of the PCR amplification. In some embodiments more than one PCR primer for each nucleic acid sequence comprises a quencher. In some embodiments detecting of the signals from the fluorescent moieties at the addressable locations over time comprises measuring the rate of hybridization of the amplified molecules with the probes.

In some embodiments the sample comprises messenger RNA or nucleotide sequences derived from messenger RNA, and the determination of the amount of nucleic acid sequence in the sample is used to determine the level of gene expression in a cell or group of cells from which the sample was derived. In some embodiments the sample comprises genomic DNA or nucleotide sequences derived from genomic DNA, and the determination of the amount of nucleic acid sequence in the sample is used to determine the genetic makeup of a cell or group of cells from which the sample was derived In some embodiments two or more PCR primers corresponding to two or more different nucleotide sequences have different quenchers. In some embodiments two or more different addressable locations comprise different fluorescent moieties. In some embodiments the different quenchers and/or different fluorescent moieties are used to determine cross-hybridization.

One aspect of the invention is a diagnostic test for determining the state of health of an individual comprising performing a method described herein on a sample from such individual.

One aspect of the invention is a method comprising measuring the amount of 10 or more amplicons corresponding to 10 or more different nucleotide sequences in a single fluid volume during or after multiple amplification cycles to determine amplicon amount-amplification cycle values, and using the amplicon amount-amplification cycle values to determine the presence or amount of the 10 or more nucleotide sequences in a sample. In some embodiments 20 or more amplicons corresponding to 20 or more different nucleotide sequences are used to determine the amount of 20 or more nucleotide sequences. In some embodiments 50 or more amplicons corresponding to 50 or more different nucleotide sequences are used to determine the amount of 50 or more nucleotide sequences.

In some embodiments the multiple amplification cycles comprise about 10-40 amplification cycles. In some embodiments the amount of the 10 or more amplicons is measured in real-time. In some embodiments amount of the 10 or more amplicons is measured by measuring the kinetics of binding of the amplicons to nucleic acid probes. In some embodiments the amount of the 10 or more amplicons is measured by measuring the quenching of fluorescence.

One aspect of the invention is system comprising: a PCR amplification reaction chamber capable of receiving: a substrate comprising a surface with an array of nucleic acid probes at independently addressable locations, and a fluid to be held contact with the substrate, the fluid comprising a nucleic acid sample comprising multiple nucleotide sequences, primers, and enzymes; a temperature controller capable of carrying out multiple PCR temperature phases and temperature cycles comprising: a heating and cooling module for raising and lowering the temperature of the fluid and/or the substrate; and a temperature sensor; and a detector capable of detecting light signals as a function of time from the independently addressable locations on the substrate within the chamber at a specific phase or phases during or after a plurality of temperature cycles while the fluid is in contact with the substrate.

In some embodiments the invention further comprises: (d) an analysis block comprising a computer and software capable of determining the amounts of amplified products hybridized to the array of probes using the detected light as a function of time, and of determining the amounts of multiple nucleotide sequences in a sample using the amounts of amplified products determined during or after a plurality of temperature cycles.

In some embodiments the detector comprises a photodiode, a CCD array, or a CMOS array.

In some embodiments the detector is in contact with the substrate, and different areas of the detector correspond to different detectable locations. In some embodiments the detector is optically coupled to the substrate with lenses and/or waveguides.

In some embodiments the heating and cooling module is capable of raising or lowering the temperature at a rate of greater than 5° C. per sec. In some embodiments the heating and cooling module is capable of raising or lowering the temperature at a rate of greater than 10° C. per sec. In some embodiments the heating and cooling module is capable of raising or lowering the temperature at a rate of greater than 20° C. per sec. In some embodiments the temperature sensor is capable of measuring temperature at an accuracy of 0.1° C.

In some embodiments the system comprises a microfluidic device having multiple arrays, each of the multiple arrays is in a chamber which can hold the fluid to be held in contact with the substrate. In some embodiments at least some of the multiple arrays are addressed with different temperature profiles. In some embodiments the microfluidic device has about 4, 5, 6, 7, 8, 9, or 10 arrays.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Introduction

Figure 1:
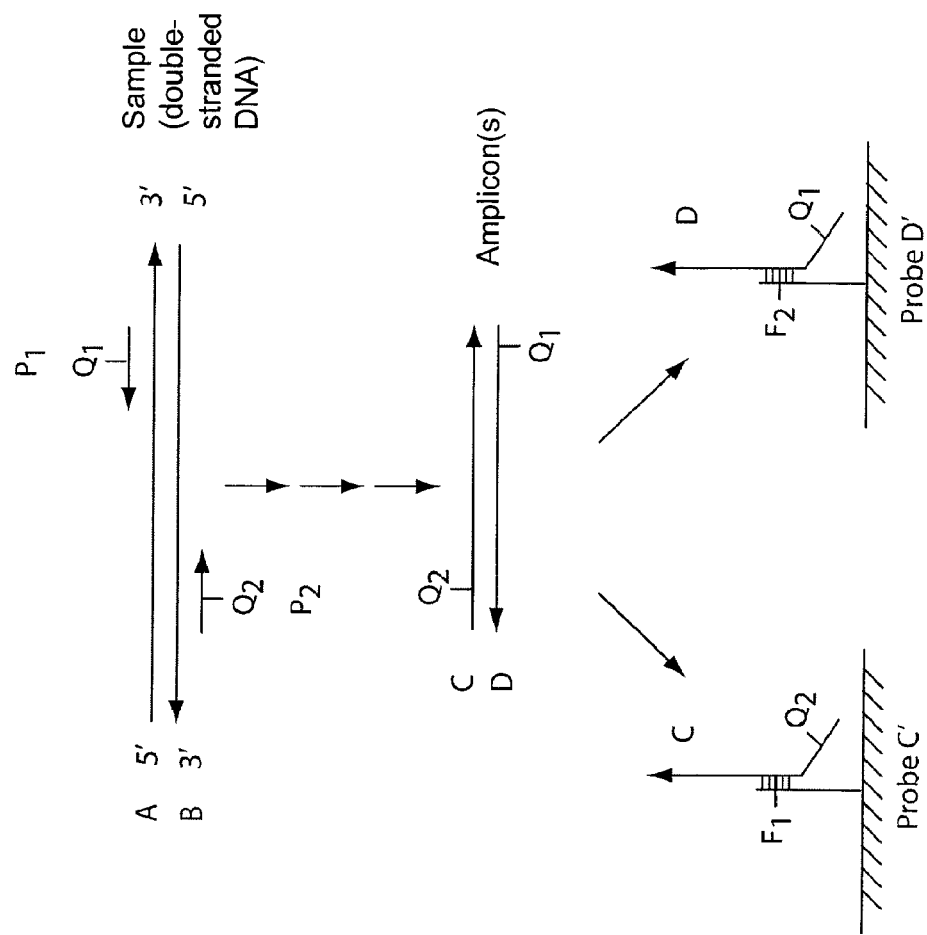
FIG. 1 illustrates an embodiment of the invention wherein primers (P1, P2) with quenchers (Q1, Q2) are incorporated into amplicons in an amplification reaction, allowing the amplicons to be detected in real-time by hybridization with probes on an array resulting in quenching of the fluorescence of fluorescent moieties (F1, F2) attached to the probes. The measurement of amplicons after multiple amplification cycles can be used to determine the concentration of the starting target nucleotide sequence (A and/or B).

The methods, devices, and systems disclosed herein relate to the detection and measurement of multiple nucleotide sequences in a sample by performing real-time measurements of amplicon binding events to nucleic acid probes bound to microarrays. The methods and systems described herein utilize real-time microarray (RT-µArray) systems. Real-time microarray systems are described in the U.S. patent application Ser. No. 11/758,621 which is incorporated herein by reference.

One aspect of the invention involves performing a PCR amplification in a solution in contact with a probe array, where the solution contains nucleotide sequences of interest. The probes are bound to the array at independently addressable locations and have fluorescent moieties. The probes are designed to specifically hybridize with amplicons generated by the PCR, and the amplicons are designed such that hybridization of the amplicon to the probe results in quenching of the fluorescent signals from the probes. During each cycle of PCR, hybridization between amplicon and probe is detected, and the denaturing step of PCR releases the amplicons for continued amplification. Preferably, the hybridization is measured in real-time during hybridization of amplicons to probes, producing kinetic measurements that can be used to determine the amount of amplicon in solution. Performing the measurement over many cycles allows the measurement of the build-up of amplicon as a function of amplification cycle, which can be extrapolated back in order to determine the concentration of the nucleotide sequence in the sample. The determination of the amount of nucleotide sequence by amplicon build-up is analogous to a CT measurement using Q-PCR, but the present invention, being in an array format, allows for a multiplex assay.

In one aspect of the invention, rather than having the fluorescent moieties that are quenched by the amplicons attached to the probe, the fluorescent moieties are attached to the surface within the independently addressable location of the probe. While the fluorescent moiety is not covalently bound to the probe, we have found that the fluorescence can still be quenched upon hybridization. This aspect allows for the measurement of amplicon-probe binding without the need for synthesizing fluorescently labeled probes.

The real-time measurement of the kinetics of multiple binding events allows for an accurate and sensitive determination of binding characteristics or of analyte concentrations for multiple species simultaneously. Real-time measurements also allow for the rapid determination of the amount of analyte present in a fluid, because the measurement can be made without waiting for saturation of binding. One aspect of present invention is the evaluation of the abundance of nucleotide sequences in a sample by the real-time detection of amplicon-probe binding events of amplicons derived from the nucleotide sequences. In certain embodiments, RT-µArray detection systems measure the concentration of the amplicons by analyzing the binding rates and/or the equilibrium concentration of the captured amplicons in a plurality of spots.

In some embodiments, the amplification method that is used is quantitative-PCR or Q-PCR. In Q-PCR, a PCR reaction is carried out to amplify a nucleotide sequence. The amount of amplicon produced is measured at the end of each amplification cycle. After a number of amplification cycles, the amount of nucleic acid in the original sample can be determined by analyzing the build-up of amplicon over the number of amplification cycles. Q-PCR allows for the determination of the presence or the amount very small amounts of sample, in some cases, down to the detection of a single molecule. While Q-PCR is a valuable technique for measuring nucleic acid sequences, the ability to measure multiple sequences at a time in a single fluid with Q-PCT reaction is limited. The present invention utilizes an array of multiple nucleic acids, thus allowing for the measurement of the presence or amount of multiple nucleic acid sequences in the same sample during the same Q-PCR amplification reaction. In some embodiments, the present invention allows for the determination of more than about 3, 5, 10, 100, 1000, 10,000, 100,000, 1,000,000 or more nucleic acid sequences in the same sample during the same amplification reaction.

The term "quantitative-PCR" or "Q-PCR" as used herein to refer to the process that is also referred to outside of this application as "real-time PCR". The term "Q-PCR" as used herein encompasses both the qualitative and quantitative determination of nucleic acid sequences. Q-PCR involves the measurement of the amount of amplicon as a function of amplification cycle, and using this information in order to determine the amount of the nucleic acid sequence corresponding to the amplicon that was present in the original sample. The Q-PCR process can be described in the following manner. A PCR reaction is carried out with a pair of primers designed to amplify a given nucleic acid sequence in a sample. The appropriate enzymes and dNTP's are added to the reaction, and the reaction is subjected to a number of amplification cycles. The amount of amplicon generated from each cycle is detected, but in the early cycles, the amount of amplicon can be below the detection threshold. The amplification can be seen as occurring in two phases, an exponential phase, followed by a non-exponential plateau phase. During the exponential phase, the amount of PCR product approximately doubles in each cycle. As the reaction proceeds, however, reaction components are consumed, and ultimately one or more of the components becomes limiting. At this point, the reaction slows and enters the plateau phase (generally between cycles 28-40). Initially, the amount of amplicon remains at or below background levels, and increases are not detectable, even though amplicon product accumulates exponentially. Eventually, enough amplified product accumulates to yield a detectable signal. The cycle number at which this occurs is called the threshold cycle, or CT. Since the CT value is measured in the exponential phase when reagents are not limited, Q-PCR can be used to reliably and accurately calculate the initial amount of template present in the reaction. The CT of a reaction is determined mainly by the amount of nucleic acid sequence corresponding to amplicon present at the start of the amplification reaction. If a large amount of template is present at the start of the reaction, relatively few amplification cycles will be required to accumulate enough product to give a fluorescent signal above background. Thus, the reaction will have a low, or early, CT. In contrast, if a small amount of template is present at the start of the reaction, more amplification cycles will be required for the fluorescent signal to rise above background. Thus, the reaction will have a high, or late, CT. The present invention allows for the measurement of the accumulation of multiple amplicons in a single fluid in a single amplification reaction, and thus the determination of the amount of multiple nucleic acid sequences in the same sample with the methodology of Q-PCR described above.

In some embodiments the Q-PCR can incorporate a blocker. For example, a sequence that is complementary to the nucleotide sequence being amplified can act as a blocker by blocking the synthesis of the amplicon. Blockers that are sensitive to small changes in nucleotide sequence can be used, for example, for single nucleotide polymorphism (SNP) determination. In some embodiments, the blocker is made from a non-natural nucleic acid with different, for example, stronger, hybridization characteristics. In some embodiments the blocker is made from locked nucleic acid (LNA) or protein nucleic acid (PNA).

In the current invention, the amplification is carried out in a fluid that is in contact with an array comprising multiple nucleic acids probes, each nucleic acid probe attached to an independently addressable location. An independently addressable location is a region of the array that can be addressed by a detector to obtain information about amplicon binding to that specific region. The multiple amplicons that are generated can each bind specifically to one or more nucleic acid probes bound to the array, and the rate of binding of the amplicons to the nucleic acids is measured in real-time to determine the amount of the amplicon in the fluid. As with Q-PCR, the sample can be subjected to multiple amplification cycles, and the amount of amplicon during or after the cycles can be measured. At the end of multiple amplification cycles, the build-up of amplicon as a function of amplification cycle can be determined, and can be used to determine the presence or amount of the nucleic acid sequences present in the original sample. This method allows the measurement of the presence or amount of tens to hundreds to millions of different nucleotide sequences in the same sample during a single amplification. This type of analysis is not practical on conventional microarrays that require hybridizations to reach saturation, require washing and drying of the array before detection, and often require a separate labeling step. The real-time arrays of the present invention allow for this multiplex Q-PCR because the fluid need not be removed from the array to detect the amplicons, and because the measurement of the amount of amplicon can be carried out rapidly without waiting for saturation of binding.

In some embodiments of the present invention, fluorescent resonance energy transfer (FRET) and/or quenching of fluorescence is used in order to determine the amount of amplicon present in the solution. For example, primers in a PCR amplification reaction are labeled with a quencher, and the nucleic acid probes on the array are labeled with a fluorescent moiety that is quenched upon binding of the amplicon to the nucleic acid probe. As the PCR amplification proceeds, the quenchers are incorporated into the amplicons formed in the amplification. During or after the temperature cycles of the PCR reaction, the decrease in the fluorescent signal with time from the probes is measured in real-time to determine the rate of binding of the amplicon to the probe which is used to determine the amount of amplicon in solution. The values obtained for the amount of amplicon as a function of amplification cycle can then be used to calculate the presence or amount of the nucleotide sequences corresponding to the amplicons in the original sample. FIGS. 1-5, described in more detail below, show embodiments of the invention that utilize FRET and quenching. The use of quenchers rather than fluorescently labeled amplicons in solution has the advantage that it minimizes the fluorescent background of the solution, thus increasing the quality of the measurement of the fluorescence at the surface. Because the different nucleic acid probes on the surface are at differently addressable locations on the surface, the binding of multiple amplicons to multiple probes can be determined in the same amplification reaction. The invention thus provides a multiplex Q-PCR system that can determine the presence or concentration of about 2, 3, 4, 5, 6, 8, 10, 20, 30, 50; 100, 200, 500, 1,000, 10,000, 100,000, 1,000,000 or more nucleotide sequences in the same fluid in same amplification reaction.

While a conventional multiplex Q-PCR allows the measurement of a small number of nucleic acid sequences in the same fluid by using dyes of different wavelengths, it has disadvantages, and is limited to a small number of amplicons. The current method carrying out multiple Q-PCR reactions on a sample, especially for larger numbers of amplicons greater than 5 or 8 is to split the sample containing the nucleotide sequence into multiple samples, and perform Q-PCR on all of the samples in parallel. This method has the disadvantages of uncertainties due to sample splitting, and that a larger sample may be needed in order to have enough material in each of the split samples. Thus, the present invention provides a unique multiplex Q-PCR system allowing for the determination of the concentration or presence of about 10 or more, about 20 or more, or about 50 or more nucleotide sequences in the same fluid in the same amplification reaction.

FIG. 1 illustrates an embodiment of the invention in which the primers have attached quenchers such that the quenchers become incorporated into the amplicons. In FIG. 1, the sample comprises a double stranded DNA, having complementary strands A and B. The sample is amplified using two primers of a primer pair (P1 and P2) each primer comprising a quencher (Q1 and Q2). In some embodiments, Q1 and Q2 will be the same quencher. In some embodiments, Q1 and Q2 will be different quenchers. In some embodiments, only one member of the primer pair will have a quencher. The primers are chosen so as to amplify the nucleotide region defined by the nucleotide region to which each of the primers are complementary on each of the two strands. The nucleotide sequences of both the A and the B strand are amplified. The double stranded DNA and the primers are then subjected to multiple temperature cycles in the presence of polymerase and dNTP's to generate amplified product, or amplicon. Here, either the generated double stranded DNA or each of the strands of the generated DNA can be referred to as amplicons. The primers comprising the quenchers become incorporated into the amplicons, resulting in amplicons which contain quenchers. Since the primers are incorporated at the 5' end of the strand that they become incorporated into, the quencher will tend to be at the 5' end of the amplicon that incorporates the primer. The quencher can be at any location along the primer. The quencher can be at the 3' end of the primer, at the 5' end of the primer, or it can be attached to nucleotides in between the ends of the primer.

During the amplification, the temperature phases are controlled to allow the measurement of binding of the generated amplicons to the probes on the array which is in contact with the fluid containing the amplicons. The amplicons can hybridize to the probes on the array as shown in FIG. 1. FIG. 1 shows, for example probe C' attached to the surface of an array. A portion of the sequence of probe C' is complementary to a portion of the sequence on amplicon C. The length of overlap illustrated in the figures is not necessarily indicative of the region of overlap between the probe and the amplicon, which can be, for example, from several bases to thousands of bases long.

Typically, as illustrated in the figures, the region of the amplicon that corresponds to the primer (and the primers themselves) will not be complementary to the probe. This design can be useful in preventing primer from binding the probe, which could result in unwanted quenching, and could result in unwanted nucleic acid strands by priming synthesis on the probes.

In this embodiment, probe C' has a fluorescent moiety attached to it. The fluorescent moiety can be attached at any place along the length of the probe. The hybridization of the probe C' to the amplicon C brings the quencher Q2 and the fluorescent moiety, F1 into proximity which can result in quenching of fluorescence from F1. The quencher Q2 and the fluorescent moiety F1, and their attachment to the amplicon and probe can be modified using methods known in the art in order to increase the interaction between F1 and Q2 and to increase the effectiveness of quenching.

The decrease in the fluorescence from F1 thus provides a measure of the amount of binding of amplicon C to probe C', and can thus be used to measure the rate of hybridization of the amplicon C to the probe C'. The measured rate of hybridization can be used to determine the amount of amplicon C in solution. The measurement of the amount of amplicon can be done during or after some or all of the temperature cycles of the amplification, and the values measured for amount of amplicon as a function of temperature cycle can be used to determine the original amount of nucleotide sequence from strand A and or strand B.

In some embodiments, amplicon D, which is complementary to amplicon C can concurrently be measured using probe D', attached to another independently addressable region of the array. By measuring the concentration of both C and D, complementary amplicon sequences, the reliability of the measurement of amplicon amount, and thus the reliability of the amount of the nucleotide sequences from A and/or B can be increased.

Figure 2:
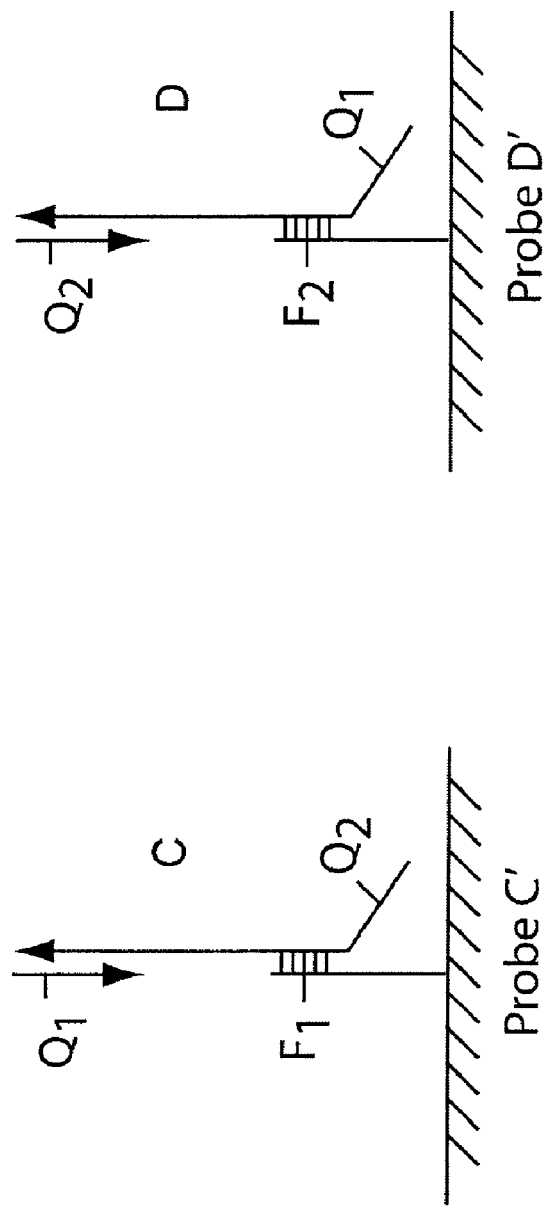
FIG. 2 shows how, for the embodiment shown in FIG. 1, primers (P1, P2) with quenchers (Q1, Q2) can, in some instances, hybridize to the 3' end of amplicons that are hybridized to probes (C', D') on the array.

FIG. 2 illustrates that in some embodiments, when amplicon C bind to probe C' near its 5' ends, the complementary primer P1 with quencher Q1 can hybridize to the 3' end of the amplicon C. In some embodiments this binding of primer can be minimized or prevented by controlling the design of the primer, amplicon, and probe or by controlling the stringency conditions such as the temperature. For example, the hybridization temperature can be chosen to allow amplicon to probe binding, but not to allow primer binding. In some embodiments, the components can be selected such that the hybridization of Q1 to C does not affect the quenching of the fluorescence at the surface of array. In other embodiments, the hybridization of Q1 to C can act to further quench the fluorescence at the surface of the array. FIG. 2 shows that primer P2 with quencher Q2 can analogously hybridize to amplicon D, which is hybridized to probe D'.

Figure 3:
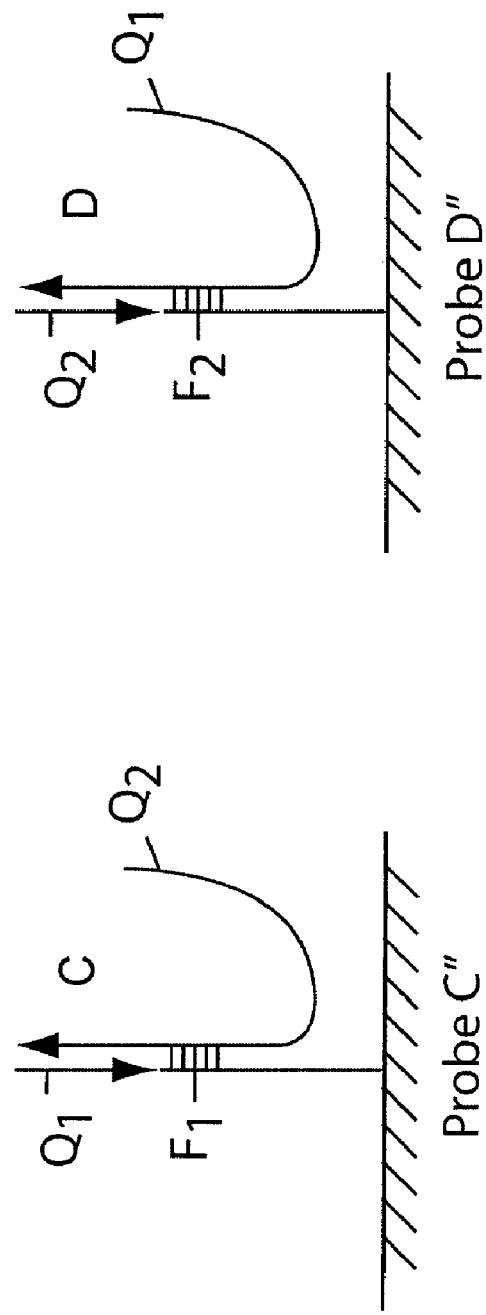
FIG. 3 illustrates an embodiment of the invention in which the probes (P1, P2) and amplicons are designed such that a primer with a quencher (Q1, Q2) hybridizes to the 3' end of an amplicon which is hybridized to a probe on an array, resulting in quenching of the fluorescence of a fluorescent moiety (F1, F2) attached to the probe.

FIG. 3 shows an embodiment where the Probe C" is designed to be complementary to a nucleotide sequence on amplicon C near the 3' region rather than near the 5' region as in FIGS. 1 and 2. In this embodiment, primer, amplicon, probe and conditions are chosen such that primer P1 with quencher Q1 is hybridized to the 3' end of C. The quencher Q1 on primer P1 is brought into proximity of the fluorescent moiety F1 on probe C", resulting in quenching of fluorescence of F1, and providing a measure of the concentration of the amplicon C. Here, quencher Q2 which is near the 5' end of C does not participate in quenching. In some embodiments both the quenching from both Q1 and Q2 can be used. FIG. 3 also shows that the same quenching strategy can be used for the complementary amplicon D.

Figure 4:
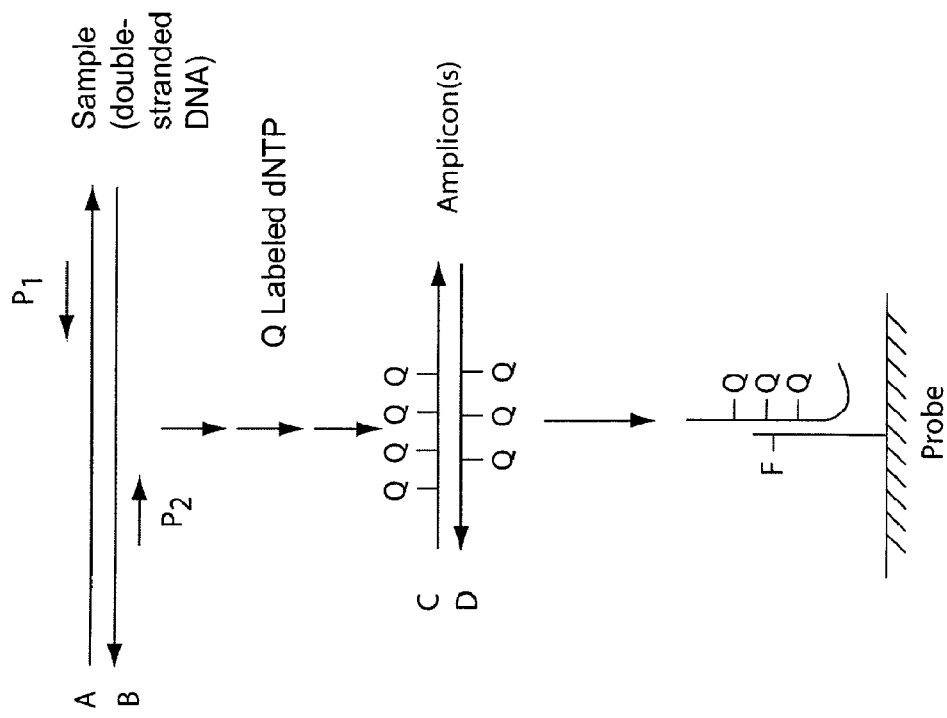
FIG. 4 illustrates an embodiment of the invention in which quenchers (Q) are incorporated into amplicons during the amplification reaction by using a d-NTP containing a quencher in the amplification. The quencher-labeled amplicons are detected in real-time by hybridization to probes on an array resulting in quenching of fluorescent moieties (F) attached to the array. The measurement of amplicons after multiple amplification cycles can be used to determine the concentration of the starting target nucleotide sequence (A and/or B).

FIG. 4 shows an alternative method of incorporating quenchers into the amplicons. Here, one or more of the dNTP's that will become incorporated into the amplicons has a quencher Q attached. The quenchers thus become incorporated into the formed amplicons. When the amplicons containing the quenchers Q bind to the surface, the probes and amplicons are designed such that the quenchers interact with and quench the fluorescence of the fluorescent moiety F on the surface bound probe. The probe can be complementary to either amplicon C or amplicon D, or the array could incorporate probes to both amplicons C and D. In some embodiments all of the dNTP's of a single type will carry a quencher. In other cases, only a fraction of the dNTP's of a single type will carry a quencher, resulting in the statistical incorporation of quenchers into the amplicons.

Figure 5:
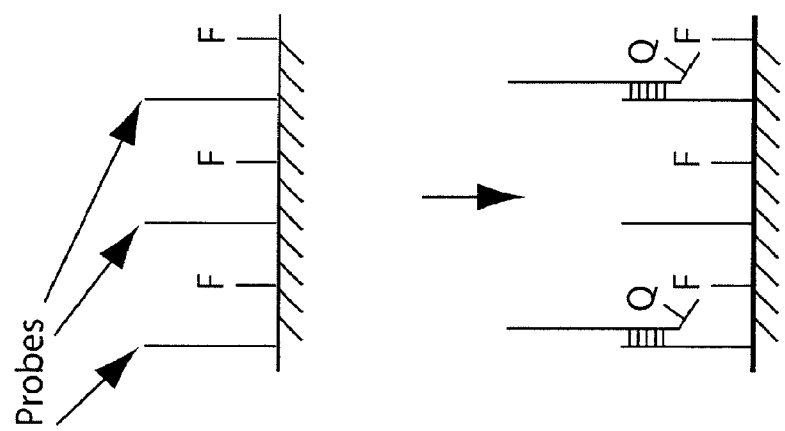
FIG. 5 shows how, in some embodiments of the invention, the fluorescent moieties (F) are bound to the surface of the array, but are not covalently bound to the probes. The fluorescent moieties can be bound directly or attached to another molecule bound to the surface. The surface bound fluorescent moieties can be quenched upon hybridization of amplicons containing quenchers (Q) to probes on the array, allowing the measurement of amplicon hybridization in real time.

FIG. 5 illustrates how, in some embodiments, the fluorescent moiety on the array is not covalently bound directly to the probes, but is bound directly to the surface of the array, or is bound through another species on the surface of the array. In FIG. 5, amplicons with quenchers Q hybridize to the probes on the array, and the quencher Q is brought into proximity of the fluorescent moiety on the surface, resulting in quenching that can be used as a measure of the amount of amplicons hybridized to the probes. This aspect of the invention can be useful in that having the fluorescent moiety attached directly to the surface can simplify manufacturing, which can improve costs, and improve the reliability of the system. For example, in some embodiments, one might be required to synthesize fluorescently labeled probe for each spot which can be costly, but by attaching the fluorescent group directly to the surface, no fluorescently labeled probes need be synthesized.

While the embodiments in FIGS. 1-5 describe quenchers and fluorescent moieties, it would be understood by persons of skill in the art that in the above embodiments, any members of a FRET pair could be incorporated into the primers, probes, and/or amplicons in the same manner. The use of quenchers on the species in solution has the advantage that the solution molecules will not create a significant background fluorescence that could interfere with the measurement of surface fluorescence. In some embodiments, the member of the FRET pair attached to the amplicon is fluorescent. In some embodiments, the member of the FRET pair that is attached to the amplicon has an emission spectrum that is different than the member of the FRET pair that is attached to the surface. When the FRET pairs interact upon binding of the amplicon to the probe, in some cases, the interaction will result in a shift in the fluorescence emission peak, for example due to charge transfer between the members of the FRET pair.

The methods and systems of the present invention comprise real-time microarray systems. Some of the advantages of RT-microarray systems over conventional microarray platforms are in their higher detection dynamic range, lower minimum detection level (MDL), robustness, faster measurement times, and lower sensitivity to array fabrication systematic errors, analyte binding fluctuation, and biochemical noise, as well as in the avoidance of the washing step required for conventional microarrays.

One aspect of the invention is a method of measuring binding of analytes to a plurality of probes on surface in "real time". As used herein in reference to monitoring, measurements, or observations of binding of probes and analytes of this invention, the term "real-time" refers to measuring the status of a binding reaction while that reaction is occurring, either in the transient phase or in biochemical equilibrium. Real time measurements are performed contemporaneously with the monitored, measured, or observed binding events, as opposed to measurements taken after a reaction is fixed. Thus, a "real time" assay or measurement generally contains not only the measured and quantitated result, such as fluorescence, but expresses this at various time points, that is, in hours, minutes, seconds, milliseconds, nanoseconds, etc. "Real time" includes detection of the kinetic production of signal, comprising taking a plurality of readings in order to characterize the signal over a period of time. For example, a real time measurement can comprise the determination of the rate of increase or decrease in the amount of analyte bound to probe. While the measurement of signal in real-time can be useful for determining rate by measuring a change in the signal, in some cases the measurement of no change in signal can also be useful. For example, the lack of change of a signal over time can be an indication that hybridization has reached steady-state.

The measurements are performed in real time with a plurality of probes and amplicons. The invention is useful for measuring probes and amplicons that bind specifically to one another. A probe and an amplicon pair that specifically bind to one another can be a specific binding pair.

One aspect of the invention is a method of measuring binding between analyte and probe which lowers, and in some cases eliminates the noise which is present in conventional microarrays and which decreases the quality of the amplicon-probe binding information. In conventional microarrays and most of the affinity-based biosensors, the detection and incubation phases of the assay procedure are carried out at different times. First the hybridization is carried out in the presence of the fluid, then the fluid is removed, the array is rinsed and dried, and conventional detection via scanning and/or imaging technique used to assess the captured targets in the dry phase. This type of conventional microarray technique is not amenable to the multiplex Q-PCR reactions of the present invention.

Figure 6:
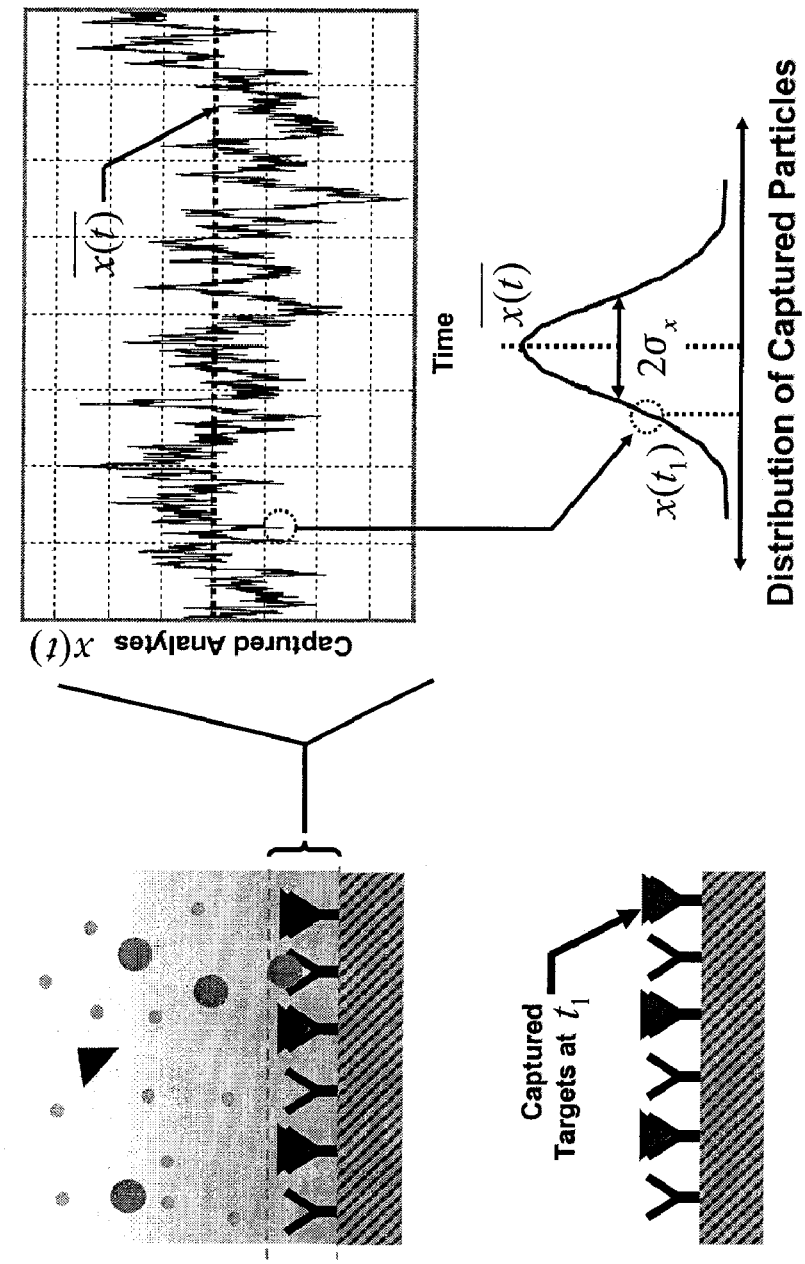
FIG. 6 shows conventional detection in the dry state after completing incubation at time $t_1$ and the uncertainty associated with it.

The following analysis illustrates inherent problems with conventional microarray analysis techniques, and the advantages of the real time microarray systems of the present invention in improving the quality of the binding measurement. Let $x(t)$ denote the total number of captured analyte in a given spot of the microarray and/or affinity-based biosensor at a given time instant t. Furthermore, let $\overline{x(t)}$ denote the expected value of $x(t)$ when the incubation process has reached biochemical equilibrium. A typical microarray procedure is focused on estimating $\overline{x(t)}$, and using its value as an indication of the analyte concentration in the sample; in fact, most data analysis techniques deduce their results based on $\overline{x(t)}$. Nevertheless, if we measure the number of captured analytes at time $t_1$ in the equilibrium, for any given microarray spot it holds that $x(t_1) \neq \overline{x(t)}$. This is due to the inherent biochemical noise and other uncertainties of the system. This phenomenon is illustrated in FIG. 6, where the number of captured analytes in each spot of the microarray fluctuates in time, even in biochemical equilibrium. Accordingly, a single measurement taken at time $t_1$, which is what conventional microarray experiments provide, essentially samples a single point of the random process of analyte binding.

Figure 7:
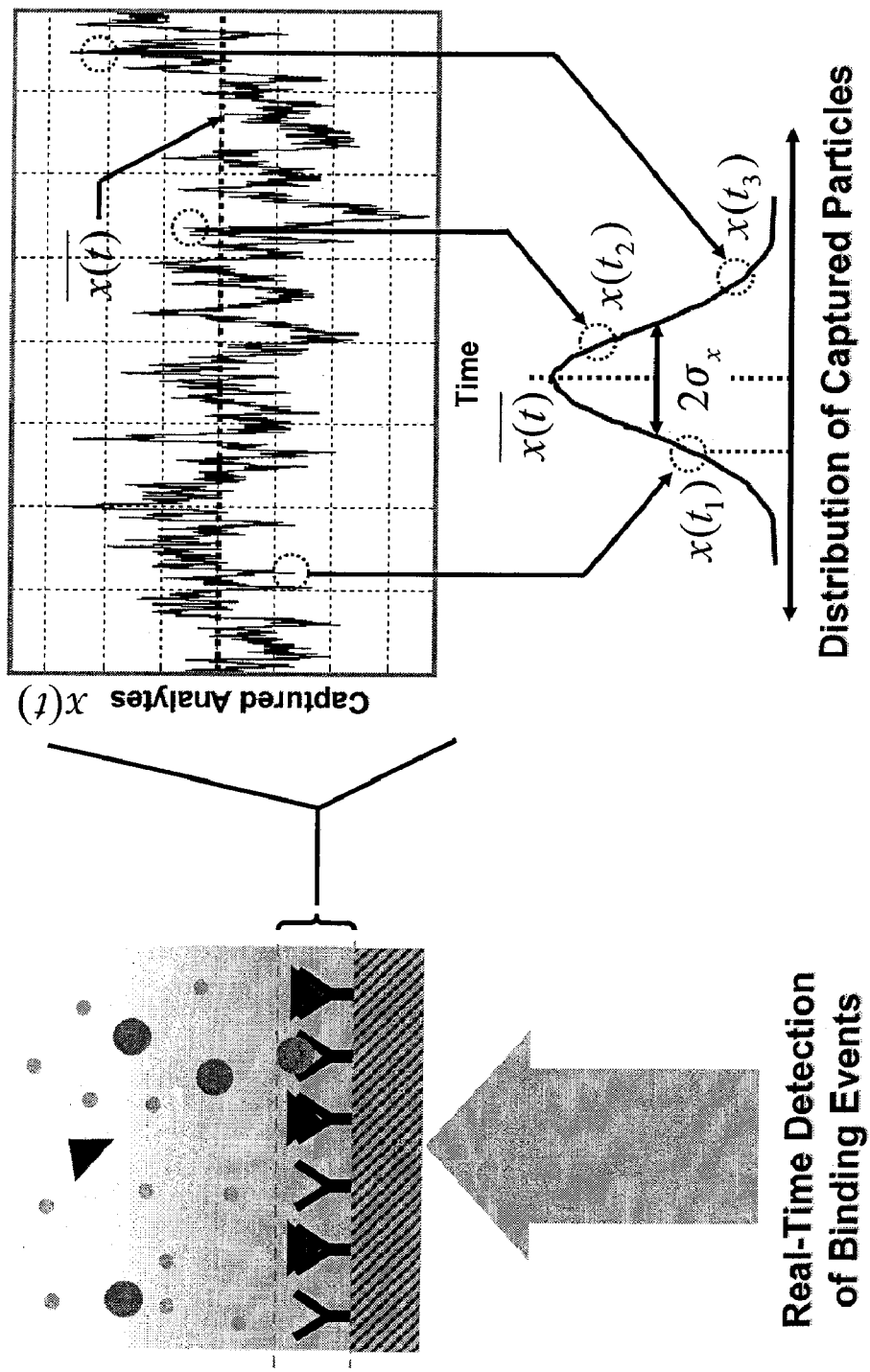
FIG. 7 shows that in real-time microarray systems of the present invention, multiple measurement of the number of captured amplicons can be carried out, providing more accurate information about binding.

Now, consider the case where we are able measure $x(t)$ multiple times, in real-time without the necessity of stopping the incubation and analyte binding reaction. This platform, which we call the real-time microarrays (RT-µArrays), has many advantages over the conventional method. In some embodiments of RT-µArrays, the kinetic of the bindings can be observed. Therefore, one can test whether the system has reached biochemical equilibrium or not. In other embodiments, multiple samples of $x(t)$ are measured (see FIG. 7), and different averaging techniques and/or estimation algorithms can be used to estimate $\overline{x(t)}$ and other characteristics of process $x(t)$.

Figure 8:
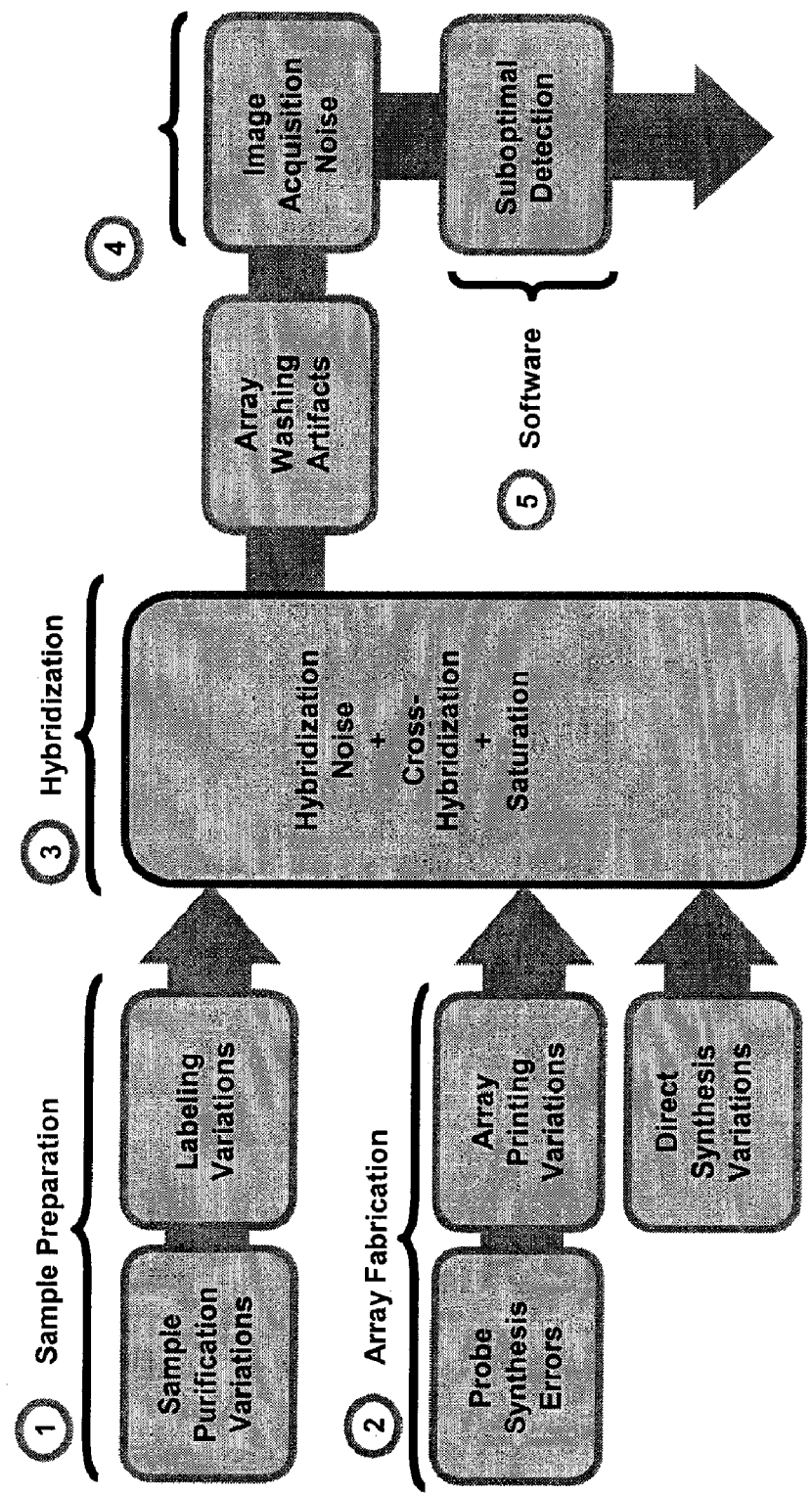
FIG. 8 shows a block diagram of the errors associated with conventional DNA microarrays that require washing and drying before detection.

FIG. 8 shows a block diagram of the errors associated with conventional DNA microarrays. These may be categorized into three stages: pre-hybridization (steps 1 and 2), hybridization (step 3), and post-hybridization (steps 4 and 5). The pre-hybridization errors arise from sample purification variations and the errors or variations in reverse transcribing mRNA to cDNA, in generating in vitro transcribed RNA complementary to the cDNA (cRNA, or IVT RNA), and or in labeling the analytes (step 1), and the errors arising from non-uniform probe spotting and or synthesis on the array (step 2). The hybridization errors arise from the inherent biochemical noise, cross-hybridization to similar targets, and the probe saturation (step 3). Post-hybridization errors include washing artifacts, image acquisition errors (step 4), and suboptimal detection (step 5). The most critical of these are probe density variations (step 2), probe saturation and cross-hybridization (step 3) and washing artifacts (step 4).

The methods and systems of the present invention can compensate for all the above errors except for those of sample preparation (step 1). Probe density variations can be measured prior to incubation and therefore accounted for in post-processing (step 5), incubation noise can be reduced by taking many samples (rather than a single one), as mentioned earlier, probe saturation can be avoided by estimating target concentrations from the reaction rates, and finally washing is avoided altogether.

Methods

One aspect of the invention is a method comprising: (a) performing a nucleic acid amplification on two or more nucleotide sequences to produce two or more amplicons in a fluid in contact with the array wherein the array comprises a solid surface with a plurality of nucleic acid probes at independently addressable locations; and (b) measuring the hybridization of the amplicons to the two or more nucleic acid probes while the fluid is in contact with the array to obtain an amplicon hybridization measurement.

In one embodiment the method involves the use of probe arrays in which each addressable location comprises a fluorescent moiety capable of emitting a signal that is quenchable upon binding of an amplicon. For example, the quenchable moiety (e.g., a fluorescent moiety) is attached to the probe on the array or in close physical proximity thereto. The surface of such array will emit signal from each addressable location which can be detected using, for example, a series of lenses and a light detector (e.g., a CCD camera or CMOS image sensor). The primers and/or the amplicons in the sample are tagged with a quencher moiety that can quench the signal from the quenchable moiety. When the quencher does not, itself, emit a light signal, there is little interference with the signal from the array. This diminishes the noise in the measurement of fluorescence from the array surface. During the course of a binding reaction between amplicons and substrate-bound probes, the signal at each addressable location is quenched. The signal at each addressable location is measured in real time, for example, by a CCD camera focused on the array surface. As the signal at any location changes as a result of binding and quenching, the change is measured. These measurements over time allow determination of the kinetics of the reaction which, in turn, allows determination of the concentration of amplicons in the sample.

Alternatively if the primers and/or amplicons can be labeled with a light-emitting reporter, such as a fluorescent label, and the background signal from these species can be diminished by focusing the detector at the array surface, thereby enhancing the signal from the surface bound moieties, and minimizing the noise from signal in solution. In addition, the interference from background fluorescence can be improved by having fluorescent labels on the surface with different emission spectra than the fluorescent moieties in solution on the primers and/or amplicons.

In another embodiment, the probes are attached to the surface of an array comprising sensors, such as a CMOS sensor array, which produce electrical signals that change as a result of binding events on the probes. This also affords real time measurement of a plurality of signals on an array (Hassibi and Lee, IEEE Sensors journal, 6-6, pp. 1380-1388, 2006, and Hassibi, A. "Integrated Microarrays," Ph.D. Thesis Stanford University, 2005.

Accordingly, the methods of this invention allow real time measurements of a plurality of binding events of amplicons to an array of probes on a solid support.

Probe and Amplicon, and Nucleotide Sequence

One aspect of the invention is the determination of the presence or amount of a nucleotide sequence. The term "nucleotide sequence" or "nucleic acid sequence" as used in this context refers to a sequence of nucleotides of which it is desired to know the presence or amount. The nucleotide sequence is typically RNA or DNA, or a sequence derived from RNA or DNA. Examples of nucleotide sequences are sequences corresponding to natural or synthetic RNA or DNA including genomic DNA and messenger RNA. The length of the sequence can be any length that can be amplified into amplicons, for example up to about 20, 50, 100, 200, 300, 400, 500, 600, 700, 800, 1,000, 1,200, 1,500, 2,000, 5,000, 10,000 or more than 10,000 nucleotides in length. It will be understood by those of skill in the art that as the number of nucleotides gets very large, the amplification can be less effective.

An "amplicon" as used herein is a molecular species that is created from the amplification of a nucleotide sequence. An amplicon is typically a polynucleotide such as RNA or DNA or mixtures thereof, in which the sequence of nucleotides in the amplicon correlates with the sequence of the nucleotide sequence from which it was generated (i.e. either corresponding to or complimentary to the sequence). The amplicon can be either single stranded or double stranded. In some embodiments, the amplicon is created using one or more primers that is incorporated into the amplicon. In some embodiments, the amplicon is generated in a polymerase chain reaction or PCR amplification, wherein two primers are used, creating what can be referred to as either a pair of complementary single stranded amplicons or a double-stranded amplicon.

The terms "probe" as used herein refers to a molecular species that binds to an amplicon in solution. A single probe or a single amplicon is generally one chemical species. That is, a single amplicon or probe may comprise many individual molecules. In some cases, a probe or amplicon may be a set of molecules that are substantially identical. A "probe" can be any type of molecule that can specifically bind to an amplicon in order to measure its amount in the fluid. A probe is a molecule that can specifically hybridize to amplicons in solution.

The probes of the present invention are bound to the substrate or solid surface. For instance, the probe can comprise biological materials deposited so as to create spotted arrays; and materials synthesized, deposited, or positioned to form arrays according to other technologies. Thus, microarrays formed in accordance with any of these technologies may be referred to generally and collectively hereafter for convenience as "probe arrays." Moreover, the term "probe" is not limited to probes immobilized in array format. Rather, the functions and methods described herein may also be employed with respect to other parallel assay devices. For example, these functions and methods may be applied with respect to probe-set identifiers that identify probes immobilized on or in beads, optical fibers, or other substrates or media. The construction of various probe arrays of the invention are described in more detail below.

In some embodiments, the probe, the amplicon, and/or the nucleotide sequence comprise a polynucleotide. The terms "polynucleotide," "oligonucleotide," "nucleic acid" and "nucleic acid molecule" as used herein include a polymeric form of nucleotides of any length, either ribonucleotides (RNA) or deoxyribonucleotides (DNA). This term refers only to the primary structure of the molecule. Thus, the term includes triple-, double- and single-stranded DNA, as well as triple-, double- and single-stranded RNA. It also includes modifications, such as by methylation and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), any other type of polynucleotide which is an N- or C-glycoside of a purine or pyrimidine base, and other polymers containing nonnucleotidic backbones. A nucleic acid of the present invention will generally contain phosphodiester bonds, i.e. a natural nucleic acid, although in some cases, as outlined below, nucleic acid analogs are included that may have alternate backbones, comprising, for example, phosphoramide (Beaucage et al., Tetrahedron 49(10):1925 (1993) and U.S. Pat. No. 5,644,048), phosphorodithioate (Briu et al., J. Am. Chem. Soc. 11 1:2321 (1989), O-methylphosphoroamidite linkages (see Eckstein, Oligonucleotides and Analogues: A Practical Approach, Oxford University Press), and peptide nucleic acid (PNA) backbones and linkages (see Carlsson et al., Nature 380:207 (1996)). Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp 169-176). These modifications of the ribose-phosphate backbone may be done to facilitate the addition of labels, or to increase the stability and half-life of such molecules in physiological environments.

In some embodiments of the invention, oligonucleotides are used. An "oligonucleotide" as used herein is a single-stranded nucleic acid ranging in length from 2 to about 1000 nucleotides, more typically from 2 to about 500 nucleotides in length. In some embodiments, it is about 10 to about 100 nucleotides, and in some embodiments, about 20 to about 50 nucleotides. It can be advantageous to use an oligonucleotide in these size ranges as probes.

In some embodiments of the invention, for example, expression analysis, the invention is directed toward measuring the nucleic acid or nucleotide sequence concentration in a sample. In some cases the nucleic acid concentration, or differences in nucleic acid concentration between different samples, reflects transcription levels or differences in transcription levels of a gene or genes. In these cases it can be desirable to provide a nucleic acid sample comprising mRNA transcript(s) of the gene or genes, or nucleic acids derived from the mRNA transcript(s). As used herein, a nucleic acid derived from an mRNA transcript refers to a nucleic acid for whose synthesis the mRNA transcript or a subsequence thereof has ultimately served as a template. Thus, a cDNA reverse transcribed from an mRNA, an RNA transcribed from that cDNA, a DNA amplified from the cDNA, an RNA transcribed from the amplified DNA, etc., are all derived from the mRNA transcript and detection of such derived products is indicative of the presence and/or abundance of the original transcript in a sample. Thus, suitable samples include, but are not limited to, mRNA transcripts of the gene or genes, cDNA reverse transcribed from the mRNA, cRNA transcribed from the cDNA, DNA amplified from the genes, RNA transcribed from amplified DNA, and the like. All of the above can comprise the nucleotide sequence for which the presence or amount is measured.

In the simplest embodiment, such a nucleic acid sample is the total mRNA or a total cDNA isolated and/or otherwise derived from a biological sample. The term "biological sample", as used herein, refers to a sample obtained from an organism or from components (e.g., cells) of an organism. The sample may be of any biological tissue or fluid. Frequently the sample will be a "clinical sample" which is a sample derived from a patient. Such samples include, but are not limited to, sputum, blood, blood cells (e.g., white cells), tissue or fine needle biopsy samples, urine, peritoneal fluid, and pleural fluid, or cells therefrom. Biological samples may also include sections of tissues such as frozen sections taken for histological purposes.

The nucleic acid (either genomic DNA or mRNA) may be isolated from the sample according to any of a number of methods well known to those of skill in the art. One of skill will appreciate that where alterations in the copy number of a gene are to be detected genomic DNA is preferably isolated. Conversely, where expression levels of a gene or genes are to be detected, preferably RNA (mRNA) is isolated.

Methods of isolating total mRNA are well known to those of skill in the art. For example, methods of isolation and purification of nucleic acids are described in detail in Chapter 3 of Laboratory Techniques in Biochemistry and Molecular Biology Hybridization With Nucleic Acid Probes, Part I. Theory and Nucleic Acid Preparation, P. Tijssen, ed. Elsevier, N.Y. (1993) and Chapter 3 of Laboratory Techniques in Biochemistry and Molecular Biology: Hybridization With Nucleic Acid Probes, Part I. Theory and Nucleic Acid Preparation, P. Tijssen, ed. Elsevier, N.Y. (1993)).

In some embodiments, the probe may comprise a polypeptide. Polypeptides and proteins can have specific binding properties. For instance, an enzyme can have a region that binds specifically with a substrate such as an amplicon. Antibodies, which can have very specific binding properties are polypeptides that can be used as probes.

Probes on a Solid Substrate

For the methods of the present invention, the probes are attached to a solid substrate. The solid substrate may be biological, nonbiological, organic, inorganic, or a combination of any of these, existing as particles, strands, precipitates, gels, sheets, tubing, spheres, containers, capillaries, pads, slices, films, plates, slides, semiconductor integrated chips etc. The solid substrate is preferably flat but may take on alternative surface configurations. For example, the solid substrate may contain raised or depressed regions on which synthesis or deposition takes place. In some embodiments, the solid substrate will be chosen to provide appropriate light-absorbing characteristics. For example, the substrate may be a polymerized Langmuir Blodgett film, functionalized glass, Si, Ge, GaAs, GaP, $SiO_2$ $SiN_4$, modified silicon, or any one of a variety of gels or polymers such as (poly)tetrafluoroethylene, (poly)vinylidenedifluoride, polystyrene, polycarbonate, or combinations thereof. The solid support and the chemistry used to attach the solid support are described in detail below.

The substrate can be a homogeneous solid and/or unmoving mass much larger than the capturing probe where the capturing probes are confined and/or immobilized within a certain distance of it. The mass of the substrate is generally at least 100 times larger than capturing probes mass. In certain embodiments, the surface of the substrate is planar with roughness of 0.1 nm to 100 nm, but typically between 1 nm to 10 nm. In other embodiments the substrate can be a porous surface with roughness of larger than 100 nm. In other embodiments, the surface of the substrate can be non-planar. Examples of non-planar substrates are spherical magnetic beads, spherical glass beads, and solid metal and/or semiconductor and/or dielectric particles.

For the methods of the present invention, the plurality of probes may be located in one addressable region and/or in multiple addressable regions on the solid substrate. In some embodiments the solid substrate has about 2, 3, 4, 5, 6, or 7-10, 10-50, 50-100, 100-500, 500-1,000, 1,000-5,000, 5,000-10,000, 10,000-50,000, 50,000-100,000, 100,000-500,000, 500,000-1,000,000 or over 1,000,000 addressable regions with probes.

In some embodiments it is also useful to have addressable regions which do not contain probe, for example, to act as control spots in order to increase the quality of the measurement, for example, by using binding to the spot to estimate and correct for non-specific binding.

Amplicon/Probe Hybridization or Binding

The methods of the present invention utilize the measurement of the hybridization or binding characteristics of multiple amplicons to multiple probes in real-time. The method is particularly useful for characterizing the binding of probes and amplicons which specifically bind or hybridize to one another. As used herein, a probe "specifically binds" to a specific analyte if it binds to that analyte with greater affinity than it binds to other substances in the sample.

The binding between the probes and the amplicons in the present invention occurs in solution; usually in an aqueous solution. An aqueous solution is a solution comprising solvent and solute where the solvent is comprised mostly or completely of water. The methods of the invention, however, can be used in any type of solution where the binding between a probe and an amplicon can occur and be observed.

Typically, the probe and amplicon will specifically bond by hybridization, but in some cases the binding can be through other molecular recognition mechanisms. Molecular recognition generally involves detecting binding events between molecules. The strength of binding can be referred to as "affinity". Affinities between biological molecules are influenced by non-covalent intermolecular interactions including, for example, hydrogen bonding, hydrophobic interactions, electrostatic interactions and Van der Waals forces. In multiplexed binding experiments, such as those contemplated here, a plurality of analytes and probes are involved. For example, the experiment may involve testing the binding between a plurality of different nucleic acid molecules or between different proteins. In such experiments analytes preferentially will bind to probes for which they have the greater affinity. Thus, determining that a particular probe is involved in a binding event indicates the presence of an amplicon in the sample that has sufficient affinity for the probe to meet the threshold level of detection of the detection system being used. One may be able to determine the identity of the binding partner based on the specificity and strength of binding between the probe and amplicon.

The specific binding can be, for example, a receptor-ligand, enzyme-substrate, antibody-antigen, or a hybridization interaction. The probe/amplicon binding pair can be nucleic acid to nucleic acid, e.g. DNA/DNA, DNA/RNA, RNA/DNA, RNA/RNA, RNA. The probe/amplicon binding pair can be a polypeptide and a nucleic acid, e.g. polypeptide/DNA and polypeptide/RNA, such as a sequence specific DNA binding protein. The probe/amplicon binding pair or amplicon/probe binding pair can be any nucleic acid and synthetic DNA/RNA binding ligands (such as polyamides) capable of sequence-specific DNA or RNA recognition. The probe/amplicon binding pair can comprise natural binding compounds such as natural enzymes and antibodies, and synthetic binding compounds. The probe/amplicon binding can comprise aptamers, which are nucleic acid or polypeptide species that have been engineered to have specific binding properties, usually through repeated rounds of in vitro selection or equivalently, SELEX (systematic evolution of ligands by exponential enrichment).

The hybridization of the amplicon to the probe results in a change in signal. Generally, the signal due to hybridization will be proportional to the amount of hybridized amplicon. While it can be advantageous to have the proportionality be relatively strict (e.g., a two fold change of the amplicon amount and a two fold change in hybridization signal), one of skill will appreciate that the proportionality can be more relaxed and even non-linear. Thus, for example, an assay where a 5 fold difference in concentration of the amplicon results in a 3 to 6 fold difference in hybridization intensity is sufficient for most purposes. Where more precise quantification is required appropriate controls can be run to correct for variations introduced in sample preparation and hybridization as described herein. Where simple detection of the presence or absence of a nucleotide sequence or large differences of changes in nucleic acid concentration are desired, no elaborate control or calibration is required.

Nucleic Acid Systems

One particularly useful aspect of the present invention involves specific hybridization between an amplicon and a probe, where both comprise nucleic acids.

As nucleic acid probe is a nucleic acid capable of binding to a target nucleic acid of complementary sequence through one or more types of chemical bonds, usually through complementary base pairing, usually through hydrogen bond formation. The nucleic acid probe may include natural (i.e. A, G, C, or T) or modified bases (7-deazaguanosine, inosine, etc.). In addition, the bases in nucleic acid probe may be joined by a linkage other than a phosphodiester bond, so long as it does not interfere with hybridization. Thus, nucleic acid probes may be peptide nucleic acids in which the constituent bases are joined by peptide bonds rather than phosphodiester linkages. The nucleic acid probes can also comprise locked nucleic acids (LNA), LNA, often referred to as inaccessible RNA, is a modified RNA nucleotide. The ribose moiety of the LNA nucleotide is modified with an extra bridge connecting 2' and 4' carbons. The bridge "locks" the ribose in 3'-endo structural conformation, which is often found in A-form of DNA or RNA. LNA nucleotides can be mixed with DNA or RNA bases in the oligonucleotide. Such oligomers are commercially available. The locked ribose conformation can enhance base stacking and backbone pre-organization, and can increase the thermal stability (melting temperature) of oligonucleotides.

In the present invention, the specific hybridization of an oligonucleotide probe to the target nucleic acid can be measured in real-time. An oligonucleotide probe will generally hybridize, bind, or duplex, with a particular nucleotide sequence of an amplicon under stringent conditions even when that sequence is present in a complex mixture. The term "stringent conditions" refers to conditions under which a probe will hybridize preferentially to its target subsequence, and to a lesser extent to, or not at all to, other sequences.

For nucleic acid systems, the nucleic acid probes of the present invention are designed to be complementary to a nucleic acid target sequence in an amplicon, such that hybridization of the amplicon and the probes of the present invention occurs. This complementarity need not be perfect; there may be any number of base pair mismatches which will interfere with hybridization between the target sequence and the single stranded nucleic acids of the present invention. However, if the number of mutations is so great that no hybridization can occur under even the least stringent of hybridization conditions, the sequence is not a complementary target sequence. Thus, an oligonucleotide probe that is not substantially complementary to a nucleic acid analyte will not hybridize to it under normal reaction conditions.

The methods of the present invention thus can be used, for example, to determine the sequence identity of a nucleic acid amplicon in solution by measuring the binding of the amplicon with known probes. The sequence identity can be determined by comparing two optimally aligned sequences or subsequences over a comparison window or span, wherein the portion of the polynucleotide sequence in the comparison window may optionally comprise additions or deletions (i.e., gaps) as compared to the reference sequence (which does not comprise additions or deletions) for optimal alignment of the two sequences. The percentage is calculated by determining the number of positions at which the identical subunit (e.g. nucleic acid base or amino acid residue) occurs in both sequences to yield the number of matched positions, dividing the number of matched positions by the total number of positions in the window of comparison and multiplying the result by 100 to yield the percentage of sequence identity.

The methods of the current invention when applied to nucleic acids, can be used for a variety of applications including, but not limited to, (1) mRNA or gene expression profiling, involving the monitoring of expression levels for example, for thousands of genes simultaneously. These results are relevant to many areas of biology and medicine, such as studying treatments, diseases, and developmental stages. For example, microarrays can be used to identify disease genes by comparing gene expression in diseased and normal cells; (2) comparative genomic hybridization (Array CGH), involving the assessment of large genomic rearrangements; (3) SNP detection arrays for identifying for Single Nucleotide Polymorphisms (SNP's) in the genome of populations; and chromatin immunoprecipitation (chIP) studies, which involve determining protein binding site occupancy throughout the genome, employing ChIP-on-chip technology.

The present invention can be very sensitive to differences in binding between amplicons comprising different nucleic acid species, in some cases, allowing for the discrimination down to a single base pair mismatch. And because the present invention allows the simultaneous measurement of multiple binding events, it is possible to analyze several amplicons simultaneously, where each is intentionally mismatched to different degrees. In order to do this, a "mismatch control" or "mismatch probe" which are probes whose sequence is deliberately selected not to be perfectly complementary to a particular target sequence can be used, for example in expression arrays. For each mismatch (MM) control in an array there, for example, exists a corresponding perfect match (PM) probe that is perfectly complementary to the same particular target sequence of an amplicon. In "generic" (e.g., random, arbitrary, haphazard, etc.) arrays, since the target nucleic acid(s) are unknown, perfect match and mismatch probes cannot be a priori determined, designed, or selected. In this instance, the probes can be provided as pairs where each pair of probes differs in one or more pre-selected nucleotides. Thus, while it is not known a priori which of the probes in the pair is the perfect match, it is known that when one probe specifically hybridizes to a particular target sequence of an amplicon, the other probe of the pair will act as a mismatch control for that target sequence. It will be appreciated that the perfect match and mismatch probes need not be provided as pairs, but may be provided as larger collections (e.g., 3, 4, 5, or more) of probes that differ from each other in particular preselected nucleotides. While the mismatch(es) may be located anywhere in the mismatch probe, terminal mismatches are less desirable as a terminal mismatch is less likely to prevent hybridization of the target sequence. In a particularly preferred embodiment, the mismatch is located at or near the center of the probe such that the mismatch is most likely to destabilize the duplex with the target sequence under the test hybridization conditions. In a particularly preferred embodiment, perfect matches differ from mismatch controls in a single centrally-located nucleotide.

It will be understood by one of skill in the art that control of the characteristics of the solution such as the stringency are important in using the present invention to measure the binding of a amplicon-probe pair, or the concentration of an amplicon. A variety of hybridization conditions may be used in the present invention, including high, moderate and low stringency conditions; see for example Maniatis et al., Molecular Cloning: A Laboratory Manual, 2d Edition, 1989, and Short Protocols in Molecular Biology, ed. Ausubel, et al, hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993). In some embodiments, highly stringent conditions are used. In other embodiments, less stringent hybridization condition; for example, moderate or low stringency conditions may be used, as known in the art; see Maniatis and Ausubel, supra, and Tijssen, supra. The hybridization conditions may also vary when a non-ionic backbone, i.e. PNA is used, as is known in the art.

Stringent conditions are sequence-dependent and will be different in different circumstances. Longer sequences tend to hybridize specifically at higher temperatures. Generally, stringent conditions can be selected to be about 5 degree. C. lower than the thermal melting point ($T_m$) for the specific sequence at a defined ionic strength and pH. The $T_m$ is the temperature (under defined ionic strength, pH, and nucleic acid concentration) at which 50% of the probes complementary to the target sequence hybridize to the target sequence at equilibrium. (As the target analyte sequences are generally present in excess, at $T_m$, 50% of the probes are occupied at equilibrium). Typically, stringent conditions will be those in which the salt concentration is at least about 0.01 to 1.0 M Na ion concentration (or other salts) at pH 7.0 to 8.3 and the temperature is at least about 30° C. for short probes (e.g., 10 to 50 nucleotides). Stringent conditions may also be achieved with the addition of destabilizing agents such as formamide.

Binding/Hybridization Kinetics

One aspect of the current invention is the use of the measurement of the binding kinetics to characterize binding of multiple probes and amplicons in solution. The term "binding kinetics" or "hybridization kinetics" as used herein refers to the rate at which the binding of the analyte to the probe occurs in a binding/hybridization reaction. The term "binding reaction" as used herein describes the reaction between probes and amplicons. The term "hybridization reaction" is a binding reaction wherein the binding comprises hybridization, for example of complementary nucleic acids. In some cases, binding reaction refers to the concurrent binding reactions of multiple amplicons and probes, and in other cases, the term binding reaction refers to the reaction between a single probe with a single amplicon. The meaning will be clear from the context of use. The kinetic measurements can be expressed as the amount of amplicon bound to the probe as a function of time. The binding or hybridization kinetics can provide information about the characteristics of the probe-amplicon binding such as the strength of binding, the concentration of amplicon, the competitive binding of an amplicon, the density of the probes, or the existence and amount of cross-hybridization.

In order to determine binding kinetics, the signal at multiple time points must be determined. The signal at least two time points is required. In most cases, more than two time points will be desired in order to improve the quality of the kinetic information. In some embodiments the signal at, 2-10, 10-50, 50-100, 100-200, 200-400, 400-800, 800-1600, 1600-3200, 3200-6400, 6400-13000, or higher than 13,000 time points will be measured. One of ordinary skill in the art can determine the effective number of points for a given embodiment. For example, where few points are obtained, the quality of information about the binding event can be low, but where the number of data points is very high, the data quality may be high, but the handling, storage, and manipulation of the data can be cumbersome.

The frequency at which the signal is measured may depend on the kinetics of the binding reaction or reactions that are being monitored. As the frequency of measurements gets lower, the time between measurements gets longer. One way to characterize a binding reaction is to refer to the time at which half of the analyte will be bound ($t_{1/2}$). The binding reactions of the invention can have a ($t_{1/2}$) from on the order of milliseconds to on the order of hours, thus the frequency of measurements can vary by a wide range. The time between measurements will generally not be evenly spaced over the time of the binding reaction. In some embodiments, a short time between of measurements will be made at the onset of the reaction, and the time between measurements will be longer toward the end of the reaction. One advantage of the present invention is the ability to measure a wide range of binding rates. A high initial frequency of measurements allows the characterization of fast binding reactions which may have higher binding, and lower frequency of measurements allows the characterization of slower binding reactions. For example, points can initially be measured at a time between points on the order of a microsecond, then after about a millisecond, points can be measured at a time between points on the order of a millisecond, then after about a second, time points can be measured at a time between points on the order of a second. Any function can be used to ramp the change in measurement frequency with time. In some cases, as described below, changes in the reaction conditions, such as stringency or temperature changes will be made during a reaction, after which it may be desirable to change the frequency of measurements to measure the rates of reaction which will be changed by the change in reaction condition.

In some embodiments, a probe will have substantially no amplicon bound to it at the beginning of the binding reaction, then the probe will be exposed to a solution containing the analyte, and the analyte will begin to bind, with more analyte bound to the probe with time. In some cases, the reaction will reach saturation, the point at which all of the analyte that is going to bind has bound. Generally, saturation will occur when a reaction has reached steady state. At steady state, in a given time period, just as many analytes are released as new analytes are bound (the on rate and off rate are equal). In some cases, with very strong binding, where the off-rate for the analyte is essentially zero, saturation will occur when substantially all of the analyte that can bind to the probe will have bound, has bound. Thus, while it is advantageous to measure a change in signal with time that can be correlated with binding kinetics, the measurement of a signal that does not change with time also provides information in the context of a real-time experiment, and can also be useful in the present invention. For example, in some cases the absence of a change in the signal will indicate the level of saturation. In other cases the absence of a change in signal can indicate that the rate of the reaction is very slow with respect to the change in time measured. It is thus a beneficial aspect of this invention to measure binding event in real time both where signals change with time and where the signals do not change with time.

One aspect of the methods of the present invention is the measurement of concentration of an amplicon from the measurement of binding kinetics. Since amplicon binding rate can be concentration-dependant, we can estimate the amplicon abundance in the sample solution using binding rates.

In some embodiments, the concentration of an analyte such as an amplicon can be determined by equations relating to the kinetics of the hybridization process. For example, suppose that the number of probes at a particular spot on the array prior to any hybridization is given by $P_0$. The probability of a specific target such as an amplicon binding to the probe site is given by Prob(binding)=$k$·Prob(target and probe in close proximity)·Prob(probe is free), (1)

where $k \leq 1$ depends of the bonds between the probe and the target and essentially a function of temperature, incubation conditions, and probe density. Here, the first probability is proportional to the number of target molecules available whereas the second probability is $$\text{Probe (probe is free)} = \frac{P(t)}{P_0}, \quad (2)$$

where $P(t)$ is the number of available probes at time t, i.e., those are not yet bound to any target. If we thus denote the forward and backwards target/probe binding reaction rates by $K_+$ and $K_-$, respectively, we may write the following differential equation for the available probe concentration $P(t)$:

$$\frac{dP(t)}{dt} = -\frac{K_+}{P_0}P(t)(C - P_0 - P(t)) + K_-(P_0 - P(t)) \quad (3)$$

where C is the original target quantity in the solution so that $C-(P_0-P(t))$ represents the available target density at time t. The above is a Riccati differential equation that can be solved in closed form. However, instead of doing so, we can note that for small values of t we have $P(t) \cong P_0$, so that the differential equation becomes $$\frac{dP(t)}{dt} = -\frac{K_+}{P_0}P(t)C. \quad (4)$$

This a first-order linear differential equation with time constant $\tau = P_0/K_+C$. Accordingly, the target density can be determined from the reaction rate (or time constant) of $P(t)$. In other words, using many sample measurements of $P(t)$ at different times and fitting them to the curve $$P(t) = P_0 \exp\left(-\frac{K_+}{P_0}C\right)t \quad (5)$$

allows us to estimate the target quantity C. In this case, the reaction rate (or inverse of the time constant) is proportional to the target concentration and inversely proportional to the probe density, something that has been observed in experiments.

One can also attempt to estimate C from the steady-state value of $P(t)$, i.e., $P_\infty$. This can be found by setting $dP(t)/dt=0$ in the original Riccati equation which leads to a quadratic equation for $P_\infty$. In some simple cases, the solution to this quadratic equation can be considerably simplified.

When the target concentration is low: In this case, we can assume $P_0 \gg C$, so that we obtain $P_\infty = P_0 - C$, (6)

i.e., the reduction in available probes is equal to the target concentration.

When the target concentration is high: In this case, we can assume that $P_0 \ll C$, so that we obtain $$P_\infty = \frac{K_-}{K_+} \cdot \frac{P_0^2}{C}. \quad (7)$$

In this case, the number of remaining probes is inversely proportional to the target concentration. This corresponds to probe saturation, which generally is not as good a method of determining C as determining C based on the reaction rate near the beginning of the reaction.

One aspect of the present invention is the determination of the binding or hybridization of amplicon to probe by measuring the rate near the beginning of the reaction. In addition to providing a more reliable estimate of C, measurement near the beginning of the reaction can shorten the time that is required to measure analyte binding over the time required for measuring binding from saturation. In some embodiments of the invention, the binding is measured during the time for less than about the first 0.1, 0.5, 1, 2, 3, 4, 5, 6, 8, 10, 12, 14, 18, 20, 25, 30, 40, 50, 60, 70, 80, or 90 percent of the amplicon to bind as compared to the amount of analyte bound at saturation. In some embodiments, the binding kinetics are determined in a time for less than about the first 20% of the amplicon to bind. In some embodiments, the binding kinetics are determined in a time for less than about the first 1-2% of the amplicon to bind.

Changing Conditions During the Binding Experiment

One aspect of the methods of the present invention is a step of changing the conditions during the binding experiment. In conventional microarrays where only the end-point is determined, only a single set of binding conditions can be tested. In the methods of the present invention, the binding conditions can be changed in order to explore multiple sets of binding conditions during the same binding experiment. The condition which is changed can be, for example, any condition that affects the rate of binding of analyte to probe. The condition which is changed can be, for example, temperature, pH, stringency, analyte concentration, ionic strength, an electric field, or the addition of a competitive binding compound.

In some embodiments, the condition that is changed changes the rate of binding or hybridization. When measuring the binding of multiple amplicons to probes in the same binding medium, as in the present invention, the kinetics of binding can vary widely for different amplicon-probe combinations. The binding rate conditions can be varied, for example, by changing the temperature, concentration, ionic strength, pH, or by applying an electric potential. The binding rates for the different amplicons can in some cases vary by many orders of magnitude, making it difficult and time consuming to measure the binding of all the analytes in one binding experiment. This ability to change the rate conditions can be used to improve the measurement of binding for multiple amplicons that bind at different rates, for example by performing the initial part of the experiment under slower rate conditions, such that rapidly binding amplicons can be readily measured, then raising the rate conditions such that more slowly binding amplicons can be readily measured. This method of changing the binding rate during the binding experiment can also be used for better characterization of a single amplicons or single set of amplicons in solution, for instance, using binding rate conditions to measure the initial portion of the binding kinetics, then increasing the binding rate conditions to measure the later portion of the binding kinetics for a single analyte, for example, to establish the level of saturation. It will be understood by those of skill in the art that this method of changing the rate conditions can result in both improved quality of measurements, such as the measurement of amplicon concentration, and/or in a savings of time. With the present method, for example by measuring the kinetics of binding, then changing the conditions to increase the rate of binding of weaker binding species, the time of the binding experiment can be reduced by greater than about 10%, 20%, 50%, 75%, or by a factor of 2, 4, 8, 10, 50, 100, 1000 or greater than 1000 over the times needed to obtain the same quality information using end-point binding methods.

In some embodiments, the condition that is changed is the stringency. As described above, the stringency can be changed by many factors including temperature, ionic strength, and the addition of compounds such as form amide. In some embodiments of the present invention, the medium is at one stringency at the beginning of the binding reaction, and at a later point the stringency of the medium is changed. This method can be used where different analytes or sets of analytes have different hybridization characteristics, for example, allowing the measurement of the binding of one set of amplicons with a high stringency, then allowing the measurement of another set of amplicons at a lower stringency in the same medium as part of the same binding experiment. This method can also be used for the characterization of binding for a single amplicon by, for instance, measuring binding at high stringency at an initial portion of the binding reaction, then lowering the stringency and measuring a later portion of the binding reaction. The ability to change stringency can also be used to create conditions where a bound amplicon becomes unbound, allowing, for instance, the measurement of the kinetics of binding at one stringency, followed by the measurement of release of the analyte into solution upon raising the stringency. This method also allows the binding of an amplicon to a probe to be measured multiple times, for example, by measuring the kinetics of binding of the amplicon under one set of stringency conditions, changing the stringency to release the amplicon, for instance, by raising the stringency, then measuring the kinetics of binding of the amplicon a subsequent time by changing the stringency conditions again, for example by lowering the stringency. Thus the ability to change the stringency during the binding reaction allows for the measurement of any number of binding and unbinding reactions with the same set of probes and amplicons.

In some embodiments of the method of the present invention, an electric potential is applied during the binding reaction to the fluid volume to electrically change the stringency of the medium. In some embodiments, the system will provide an electrical stimulus to the capturing region using an electrode structure which is placed in proximity of the capturing region. If the amplicon is an electro-active species and/or ion, the electrical stimulus can apply an electrostatic force of the analyte. In some embodiments the electrical potential is direct current (DC). In some embodiments, the electric potential is time-varying. In some embodiments the electric potential has both DC and time varying aspects. Their amplitude of the applied potential can be between 1 mV to 10V, but typically between 10 mV to 100 mV. The frequency of time-varying signal is between 1 Hz to 1000 MHz, but typically between 100 Hz to 100 kHz.

Detection of Signals

For the methods of the present invention, a signal is detected that can be correlated with the binding of amplicons to the plurality of probes. The type of signals appropriate for the invention is any signal that can be amount of amplicon bound to the plurality of probes. Appropriate signals include, for example, electrical, electrochemical, magnetic, mechanical, acoustic, or electromagnetic (light) signals. Examples of electrical signals useful in the present invention that can be correlated with amplicon binding are capacitance and/or impedance. For example, amplicons labeled with metals or metal clusters can change the capacitance and/or the impedance of a surface in contact with a fluid, allowing the amount of analyte bound to the probe on the surface to be determined. The electrical measurement can be made at any frequency including DC, 0-10 Hz, 10-100 Hz, 100-1000 Hz, 1 KHz-10 KHz, 10 KHz-100 KHz, 100 KHz-1 MHz, 1 MHz-10 MHZ, 10 MHz-100 MHz, 100 MHz-1 GHz, or above 1 &Hz. In some embodiments, impedance spectroscopy can be used which obtains impedance versus frequency for any range of frequencies within the range of frequencies described above. Examples of electrochemical signals useful in the present invention that can be correlated with amplicon binding include amperometric and voltammetric measurements, and/or measurements that involve the oxidation or reduction of redox species. For example, the amplicon can be labeled with a compound which undergoes an oxidation or reduction reaction at a known redox potential, and the oxidative or reductive current can be correlated with the amount of amplicon bound to surface probes. Examples of mechanical signals include the use of microelectromechanical (MEMS) devices. For example, the binding of amplicon to probe on the surface of a small surface feature, such as a cantilever, can change the mass of the surface feature, the vibration frequency of which can then be correlated with the amount of analyte bound to the probe. Generally, the higher the mass, the lower the vibration frequency. Examples of acoustic signals include surface acoustic wave (SAW), and surface plasmon resonance signals. A surface acoustic wave (SAW) is an acoustic wave traveling along the surface of a material having some elasticity, with amplitude that typically decays exponentially with the depth of the substrate. The binding of labeled or unlabeled amplicon to probe on a surface can change the SAW characteristics, e.g. amplitude, frequency in a manner that can be correlated with the amount of analyte bound to a probe. Surface plasmon resonance relies on surface plasmons, also known as surface plasmon polaritons, which are surface electromagnetic waves that propagate parallel, usually along a metal/dielectric interface. Since the wave is on the boundary of the metal and the external medium (water for example), these oscillations are very sensitive to any change of this boundary, such as the adsorption of molecules to the metal surface. The binding of labeled or unlabeled analyte to a probe attached to the surface can change the frequency of the resonant surface plasmon in a manner that can be correlated with the amount of amplicon bound to the probes.

Particularly useful signals for the methods of the present invention are electromagnetic (light) signals. Examples of optical signals useful in the present invention are signals from fluorescence, luminescence, and absorption. As used herein, the terms "optical", "electromagnetic" or "electromagnetic wave" and "light" are used interchangeably. Electromagnetic waves of any frequency and wavelength that can be correlated to the amount of analyte bound to probe on the surface can be used in the present invention including gamma rays, x-rays, ultraviolet radiation, visible radiation, infrared radiation, and microwaves. While some embodiments are described with reference to visible (optical) light, the descriptions are not meant to limit the embodiments to those particular electromagnetic frequencies.

For the methods of the present invention it is desired that the signal changes upon the binding of the analyte to the probe in a manner that correlates with the amount of amplicon bound. In some cases, the change in signal will be a change in intensity of the signal. In some embodiments, the signal intensity will increase as more amplicon is bound to probe. In some embodiments, the signal intensity will decrease as more amplicon is bound to probe. In some embodiments, the change in signal is not a change in intensity, but can be any other change in the signal that can be correlated with amplicon binding to probe. For example, the change in signal upon binding of the amplicon can be a change in the frequency of the signal. In some embodiments, the signal frequency will increase as more amplicon is bound to probe. In some embodiments, the signal frequency will decrease as more amplicon is bound to the probe.

The signal that is measured is generally the signal from the region of the solid surface. In some embodiments signal from the solution is used as the signal that can be correlated with the amount of amplicon bound to the probe. The measurement of hybridization of the amplicons to the probes provides an amplicon hybridization measurement. The amplicon hybridization measurement can, in some embodiments, be correlated with the amount of amplicon bound to the probe.

As used herein, the concentration of a substance such as the amplicon is the amount of the substance per volume of fluid in which the amplicon is dissolved. Thus, a measurement of the concentration of the amplicon will provide a measurement of the amount of the amplicon when the volume of the fluid is known.

In some embodiments of the methods of the present invention, labels are attached to the amplicons and/or the probes. Any label can be used on the amplicon or probe which can be useful in the correlation of signal with the amount of analyte bound to the probe. It would be understood by those of skill in the art that the type of label which is used on the amplicon and/or probe will depend on the type of signal which is being used, for example, as described above, a dense label for a mechanical signal, or a redox active label for a voltammetric measurement.

In some embodiments, the signal that can be correlated to the amount of amplicon bound to probe is due to the buildup of label at the surface as more amplicon is bound to the probes on the surface. For example, where the amplicon has a fluorescent label, as more amplicon binds, the intensity of the fluorescent signal can increase in a manner that can be correlated with the amount of amplicon bound to probe on the surface.

In some embodiments, the signal that can be correlated to the amount of amplicon bound to probe is due to a change in the signal from label on the surface upon binding of the amplicon to the probe. For example, where a fluorescent label is on the surface, and the amplicon and/or primers are labeled with a compound capable of changing the fluorescent signal of the surface fluorescent label upon binding of the amplicon with the probes, the change in signal can be correlated with the amount of amplicon bound to probe. In some embodiments, the amplicon is labeled with a quencher, and the decrease in intensity from the surface fluorescent label due to quenching is correlated to the increased amount of amplicon bound to probe. In some embodiments, the amplicon and/or primers are labeled with a fluorescent compound which can undergo energy transfer with the fluorescent label on the surface such that the increase in fluorescence from the amplicon fluorescent label and/or the decrease in fluorescence from the surface fluorescent label can be correlated with the amount of amplicon bound to probe. In some embodiments the surface fluorescent label is bound directly, e.g. covalently to the probe. In some embodiments, the surface fluorescent label is bound to the surface, is not bound to the probe, but is in sufficient proximity that the binding of the amplicon to the probe produces a change in signal from the surface fluorescent label that can be correlated with the amount of amplicon bound to probe.

In some embodiments, the amplicon is unlabeled, and the concentration of the amplicon is determined by competitive binding with another labeled species, which competes with the amplicon for biding to a probe. For example, where we have a solution with an amplicon, A, whose concentration we want to determine, and we have a competitive binding species, B, whose binding characteristics with probe and whose concentration are known, then using the present invention, we can use, for example, an array of probes on a surface to determine the concentration of A by determining the amount of competitive binding of B to a probe. For example, the probe is attached to a surface that is fluorescently labeled, and B is labeled with a quencher such that the level of quenching of the surface fluorescence can be correlated with the amount of B bound to the probe. The rate of binding of B to the probe is measured in real time, and the concentration of A is determined by knowing the characteristics of A as a competitive binder. In some embodiments, the amount of the competitive binding species does not need to be known beforehand.

Electromagnetic Signals—Optical Methods

The use of optical detection provides a variety of useful ways of implementing the methods of the present invention. Optical methods include, without limitation, absorption, luminescence, and fluorescence.

Some embodiments of the invention involve measuring light absorption, for example by dyes. Dyes can absorb light within a given wavelength range allowing for the measurement of concentration of molecules that carry that dye. In the present invention, dyes can be used as labels, on the amplicon and/or primers or on the probe. The amount of dye can be correlated with the amount of amplicon bound to the surface in order to determine binding kinetics. Dyes can be, for example, small organic or organometallic compounds that can be, for example, covalently bound to the amplicon and/or primer or probe. Dyes which absorb in the ultraviolet, visible, infrared, and which absorb outside these ranges can be used in the present invention. Methods such as attenuated total reflectance (ATR), for example for infrared, can be used to increase the sensitivity of the surface measurement.

Some embodiments of the invention involve measuring light generated by luminescence. Luminescence broadly includes chemiluminescence, bioluminescence, phosphorescence, and fluorescence. In some embodiments, chemiluminescence, wherein photons of light are created by a chemical reaction such as oxidation, can be used.

Fluorescent Systems

A useful embodiment of the present invention involves the use of fluorescence. As used herein, fluorescence refers to the process wherein a molecule relaxes to its ground state from an electronically excited state by emission of a photon. As used herein, the term fluorescence also encompasses phosphorescence. For fluorescence, a molecule is promoted to an electronically excited state generally by the absorption of ultraviolet, visible, or near infrared radiation. The excited molecule then decays back to the ground state, or to a lower-lying excited electronic state, by emission of light. An advantage of fluorescence for the methods of the invention is its high sensitivity. Fluorimetry may achieve limits of detection several orders of magnitude lower than for absorption. Limits of detection of $10^{-10}$ M or lower are possible for intensely fluorescent molecules; in favorable cases under stringently controlled conditions, the ultimate limit of detection (a single molecule) may be reached.

A wide variety of fluorescent molecules can be utilized in the present invention including small molecules, fluorescent proteins and quantum dots. Useful fluorescent molecules (fluorophores) include, but are not limited to: 1,5 IAEDANS; 1,8-ANS; 4-Methylumbelliferone; 5-carboxy-2,7-dichlorofluorescein; 5-Carboxyfluorescein (5-FAM); 5-Carboxynapthofluorescein; 5-Carboxytetramethylrhodamine (5-TAMRA); 5-FAM (5-Carboxyfluorescein); 5-HAT (Hydroxy Tryptamine); 5-Hydroxy Tryptamine (HAT); 5-ROX (carboxy-X-rhodamine); 5-TAMRA (5-Carboxytetramethylrhodamine); 6-Carboxyrhodamine 6G; 6-CR 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; Aequorin (Photoprotein); AFPs—AutoFluorescent Protein—(Quantum Biotechnologies); Alexa Fluor 350™; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexion; Alizarin Red; Allophycocyanin (APC); AMC, AMCA-S; AMCA (Aminomethylcoumarin); AMCA-X; Aminoactinomycin D; Aminocoumarin; Aminomethylcoumarin (AMCA); Anilin Blue; Anthrocyl stearate; APC (Allophycocyanin); APC-Cy7; APTRA-BTC; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole); BCECF (high pH); BCECF (low pH); Berberine Sulphate; Beta Lactamase; Bimane; Bisbenzamide; Bisbenzimide (Hoechst); bis-BTC; Blancophor FFG; Blancophor SV; BOBO™-1; BOBO™-3; Bodipy 492/515; Bodipy 493/503; Bodipy 500/510; Bodipy 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy Fl; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; BTC; BTC-SN; Calcein; Calcein Blue; Calcium Crimson™; Calcium Green; Calcium Green-1 Ca.sup.2+Dye; Calcium Green-2 Ca.sup.2+; Calcium Green-SN Ca.sup.2+; Calcium Green-C18 Ca.sup.2$^+$; Calcium Orange; Calcofluor White; Carboxy-X-rhodamine (5-ROX); Cascade Blue™; Cascade Yellow; Catecholamine; CCF2 (GeneBlazer); CFDA; Chlorophyll; Chromomycin A; Chromomycin A; CL-NERF; CMFDA; Coumarin Phalloidin; C-phycocyanine; CPM Methylcoumarin; CTC; CTC Formazan; Cy2™; Cy3.1 8; Cy3.5™; Cy3™; Cy5.1 8; Cy5.5™; Cy5™; Cy7™; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3' DCFDA; DCFH (Dichlorodihydrofluorescein Diacetate); DDAO; DHR (Dihydrorhodamine 123); Di-4-ANEPPS; Di-8-ANEPPS (non-ratio); DiA (4-Di-16-ASP); Dichlorodihydrofluorescein Diacetate (DCFH); DiD—Lipophilic Tracer; DiD (DiIC18(5)); DIDS; Dihydrorhodamine 123 (DHR); DiI (DiIC18(3)); Dinitrophenol; DiO (DiOC18(3)); DiR; DiR (DiIC18(7)); DM-NERF (high pH); DNP; Dopamine; DTAF; DY-630-NHS; DY-635-NHS; ELF 97; Eosin; Erythrosin; Erythrosin ITC; Ethidium Bromide; Ethidium homodimer-1 (EthD-1); Euchrysin; EukoLight; Europium (III) chloride; EYFP; Fast Blue; FDA; Feulgen (Pararosaniline); FIF (Formaldehyde Induced Fluorescence); FITC; Flazo Orange; Fluo-3; Fluo-4; Fluorescein (FITC); Fluorescein Diacetate; Fluoro-Emerald; Fluoro-Gold (Hydroxystilbamidine); Fluor-Ruby; Fluor X; FM 1-43™; FM 4-46; Fura Red™ (high pH); Fura Red™/Fluo-3; Fura-2; Fura-2/BCECF; Genacryl Brilliant Red B; Genacryl Brilliant Yellow 10GF; Genacryl Pink 3G; Genacryl Yellow 5GF; GeneBlazer (CCF2); Gloxalic Acid; Granular blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1, high calcium; Indo-1, low calcium; Indodicarbocyanine (DiD); Indotricarbocyanine (DiR); Intrawhite Cf; JC-1; JO-JO-1; JO-PRO-1; LaserPro; Laurodan; LDS 751 (DNA); LDS 751 (RNA); Leucophor PAF; Leucophor SF; Leucophor WS; Lissamine Rhodamine; Lissamine Rhodamine B; Calcein/Ethidium homodimer; LOLO-1; LO-PRO-1; Lucifer Yellow; Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-indo-1; Magnesium Green; Magnesium Orange; Malachite Green; Marina Blue; Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; Nitrobenzoxadidole; Noradrenaline; Nuclear Fast Red; Nuclear Yellow; Nylosan Brilliant Flavin E8G; Oregon Green; Oregon Green 488-X; Oregon Green™; Oregon Green™ 488; Oregon Green™ 500; Oregon Green™ 514; Pacific Blue; Pararosaniline (Feulgen); PBFI; PE-Cy5; PE-Cy7; PerCP; PerCP-Cy5.5; PE-TexasRed [Red 613]; Phloxin B (Magdala Red); Phorwite AR; Phorwite BKL; Phorwite Rev; Phorwite RPA; Phosphine 3R; PhotoResist; Phycoerythrin B [PE]; Phycoerythrin R [PE]; PKH26 (Sigma); PKH67; PMIA; Pontochrome Blue Black; POPO-1; POPO-3; PO-PRO-1; PO-PRO-3; Primuline; Procion Yellow; Propidium lodid (PL); PyMPO; Pyrene; Pyronine; Pyronine B; Pyrozal Brilliant Flavin 7GF; QSY 7; Quinacrine Mustard; Red 613 [PE-TexasRed]; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine Phalloidine; Rhodamine Red; Rhodamine WT; Rose Bengal; R-phycocyanine; R-phycoerythrin (PE); S65A; S65C; S65L; S65T; SBFI; Serotonin; Sevron Brilliant Red 2B; Sevron Brilliant Red 4G; Sevron Brilliant Red B; Sevron Orange; Sevron Yellow L; SITS; SITS (Primuline); SITS (Stilbene Isothiosulphonic Acid); SNAFL calcein; SNAFL-1; SNAFL-2; SNARF calcein; SNARF1; Sodium Green; SpectrumAqua; SpectrumGreen; SpectrumOrange; Spectrum Red; SPQ (6-methoxy-N-(3-sulfopropyl)quinolinium); Stilbene; Sulphorhodamine B can C; Sulphorhodamine Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; Tetracycline; Tetramethylrhodamine (TRITC); Texas Red™; Texas Red-X™ conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO-1; TO-PRO-3; TO-PRO-5; TOTO-1; TOTO-3; TriColor (PE-Cy5); TRITC TetramethylRodamineIsoThioCyanate; True Blue; TruRed; Ultralite; Uranine B; Uvitex SFC; WW 781; X-Rhodamine; XRITC; Xylene Orange; Y66F; Y66H; Y66W; YO-PRO-1; YO-PRO-3; YOYO-1; YOYO-3, Sybr Green, Thiazole orange (interchelating dyes), or combinations thereof.

Some embodiments of the present invention include the Alexa Fluor dye series (from Molecular Probes/Invitrogen) which cover a broad spectrum and match the principal output wavelengths of common excitation sources such as Alexa Fluor 350, Alexa Fluor 405, 430, 488, 500, 514, 532, 546, 555, 568, 594, 610, 633, 635, 647, 660, 680, 700, and 750. Some embodiments of the present invention include the Cy Dye fluorophore series (GE Healthcare), also covering a wide spectrum such as Cy3, Cy3B, Cy3.5, Cy5, Cy5.5, Cy7. Some embodiments of the present invention include the Oyster dye fluorophores (Denovo Biolabels) such as Oyster-500, -550, -556, 645, 650, 656. Some embodiments of the present invention include the DY-Labels series (Dyomics), for example, with maxima of absorption that range from 418 nm (DY-415) to 844 nm (DY-831) such as DY-415, -495, -505, -547, -548, -549, -550, -554, -555, -556, -560, -590, -610, -615, -630, -631, -632, -633, -634, -635, -636, -647, -648, -649, -650, -651, -652, -675, -676, -677, -680, -681, -682, -700, -701, -730, -731, -732, -734, -750, -751, -752, -776, -780, -781, -782, -831, -480XL, -481XL, -485XL, -510XL, -520XL, -521XL. Some embodiments of the present invention include the ATTO fluorescent labels (ATTO-TEC GmbH) such as ATTO 390, 425, 465, 488, 495, 520, 532, 550, 565, 590, 594, 610, 611X, 620, 633, 635, 637, 647, 647N, 655, 680, 700, 725, 740. Some embodiments of the present invention include CAL Fluor and Quasar dyes (Biosearch Technologies) such as CAL Fluor Gold 540, CAL Fluor Orange 560, Quasar 570, CAL Fluor Red 590, CAL Fluor Red 610, CAL Fluor Red 635, Quasar 670. Some embodiments of the present invention include quantum dots such as the EviTags (Evident Technologies) or quantum dots of the Qdot series (Invitrogen) such as the Qdot 525, Qdot565, Qdot585, Qdot605, Qdot655, Qdot705, Qdot 800. Some embodiments of the present invention include fluorescein, rhodamine, and/or phycoerythrin.

FRET and Quenching

In some embodiments of the invention, fluorescence resonance energy transfer is used to produce a signal that can be correlated with the binding of the amplicon to the probe. FRET arises from the properties of certain fluorophores. In FRET, energy is passed non-radiatively over a distance of about 1-10 nanometers between a donor molecule, which is a fluorophore, and an acceptor molecule. The donor absorbs a photon and transfers this energy non-radiatively to the acceptor (Forster, 1949, Z. Naturforsch. A4: 321-327; Clegg, 1992, Methods Enzymol. 211: 353-388). When two fluorophores whose excitation and emission spectra overlap are in close proximity, excitation of one fluorophore will cause it to emit light at wavelengths that are absorbed by and that stimulate the second fluorophore, causing it in turn to fluoresce. The excited-state energy of the first (donor) fluorophore is transferred by a resonance induced dipole—dipole interaction to the neighboring second (acceptor) fluorophore. As a result, the excited state lifetime of the donor molecule is decreased and its fluorescence is quenched, while the fluorescence intensity of the acceptor molecule is enhanced and depolarized. When the excited-state energy of the donor is transferred to a non-fluorophore acceptor, the fluorescence of the donor is quenched without subsequent emission of fluorescence by the acceptor. In this case, the acceptor functions as a quencher.

Pairs of molecules that can engage in fluorescence resonance energy transfer (FRET) are termed FRET pairs. In order for energy transfer to occur, the donor and acceptor molecules must typically be in close proximity (up to 7 to 10 nanometers. The efficiency of energy transfer can falls off rapidly with the distance between the donor and acceptor molecules.

Molecules that can be used in FRET include the fluorophores described above, and includes fluorescein, 5-carboxyfluorescein (FAM), 2'7'-dimethoxy-4'5'-dichloro-6-carboxyfluorescein (JOE), rhodamine, 6-carboxyrhodamine (R6G), N,N,N',N'-tetramethyl-6-carboxyrhodamine (TAMRA), 6-carboxy-X-rhodamine (ROX), 4-(4'-dimethylaminophenylazo) benzoic acid (DABCYL), and 5-(2'-aminoethyl)aminonaphthalene-1-sulfonic acid (EDANS). Whether a fluorophore is a donor or an acceptor is defined by its excitation and emission spectra, and the fluorophore with which it is paired. For example, FAM is most efficiently excited by light with a wavelength of 488 nm, and emits light with a spectrum of 500 to 650 nm, and an emission maximum of 525 nm. FAM is a suitable donor fluorophore for use with JOE, TAMRA, and ROX (all of which have their excitation maximum at 514 nm).

In some embodiments of the methods of the present invention, the acceptor of the FRET pair is used to quench the fluorescence of the donor. In some cases, the acceptor has little to no fluorescence. The FRET acceptors that are useful for quenching are referred to as quenchers. Quenchers useful in the methods of the present invention include, without limitation, Black Hole Quencher Dyes (Biosearch Technologies such as BHQ-0, BHQ-1, BHQ-2, BHQ-3, BHQ-10; QSY Dye fluorescent quenchers (from Molecular Probes/Invitrogen) such as QSY7, QSY9, QSY21, QSY35, and other quenchers such as Dabcyl and Dabsyl; Cy5Q and Cy7Q and Dark Cyanine dyes (GE Healthcare), which can be used, for example, in conjunction with donor fluors such as Cy3B, Cy3, or Cy5; DY-Quenchers (Dyomics), such as DYQ-660 and DYQ-661; and ATTO fluorescent quenchers (ATTO-TEC GmbH), such as ATTO 540Q, 580Q, 612Q.

In some embodiments of the methods of the invention, both the amplicons and the probes have labels that are members of a FRET pair, and the labels are attached such that when an amplicon binds to a probe, FRET will occur between the labels, resulting in a change in signal that can be correlated with the binding of amplicon to probe in real-time. The change in signal can be the decrease in the intensity of the donor and/or the increase in the intensity of the acceptor. The FRET pair can be chosen such that emission wavelength of the donor fluorophore is far enough from the emission wavelength of the acceptor fluorophore, that the signals can be independently measured. This allows the measurement of both the decrease in signal from the donor and the increase in signal from the acceptor at the same time, which can result in improvements in the quality of the measurement of binding. In some cases, the probe will have a label that is the donor of the donor-acceptor pair. In some cases, the amplicon will have a label that is the donor of the donor acceptor pair.

In some embodiments of the methods of the invention, the amplicon will have a fluorescent label that is a member of a FRET pair, and the other member of the FRET pair will be attached to the surface, wherein the member of the FRET pair attached to the surface is not covalently linked to the probe. In some cases, the amplicon will have a label that is the donor of the donor-acceptor pair. In some cases, the amplicon will have a label that is the acceptor of the donor acceptor pair. In some embodiments, the member of the FRET pair that is attached to the surface is attached to an oligonucleotide which is attached to the surface (a surface-bound label). The oligonucleotide that is labeled with the FRET pair can be a nucleotide sequence that does not have a sequence anticipated to specifically bind to an amplicon. The use of a surface-bound label allows for the labeling of multiple areas of an array without having to label each specific binding probe. This can simplify the production of the array and reduce costs. We have found that even though the surface-bound FRET pairs are not covalently bound to the probe, they can be sensitive to the binding of the amplicon labeled with the other member of the FRET pair in a manner that allows the change in signal to be correlated with the amount of amplicon bound to probe.

In some embodiments of the methods of the present invention, the amplicon is labeled with a quencher, and the probe is labeled with a donor fluorophore. The amplicon is labeled with the quencher such that when amplicon binds with the probe, the fluorescence from the fluorescent label on the probe is quenched. Thus, the signal, measured in real-time, can be correlated with the amount of binding of the amplicon and the probe, allowing for the measurement of the kinetics of the binding. In some embodiments of the methods of the present invention, the amplicon is labeled with a quencher, and the probe is labeled with a donor fluorophore, that is not covalently attached to it. The quencher is labeled such that when amplicon binds with the probe, the fluorescence from the fluorescent label on the probe is quenched. Thus, the signal, measured in real-time, can be correlated with the amount of binding of the amplicon and the probe, allowing for the measurement of the kinetics of the binding.

In some embodiments of the methods of the present invention, the amplicon is labeled with a quencher, and the surface is labeled with a donor fluorophore wherein the donor fluorophore is not covalently linked to the probe (e.g. with a surface bound fluorescent label). The quencher is labeled such that when amplicon binds with the probe, the fluorescence from the fluorescent label on the surface is quenched. Thus, the signal, measured in real-time, can be correlated with the amount of binding of the amplicon and the probe, allowing for the measurement of the kinetics of the binding.

Where the probe is labeled with a fluorophore, one aspect of the invention is the use of an image of the fluorescently labeled probe on the surface obtained before binding has occurred in order to effectively establish a baseline signal for the state where no binding of amplicon to probe has occurred. In conventional arrays, in which unlabeled probe is treated with labeled amplicon, and the signal is measured after hybridization and washing, it can be difficult to know exactly how much probe is actually on the array in the region of interest. Thus, differences in array manufacture can affect the quality of the data. In the present invention, where the probe is labeled with fluorophore, the image of the labeled probe on the surface provides a measurement of the amount of probe actually on the surface, increasing the quality and reliability of the binding measurement.

Figure 9:
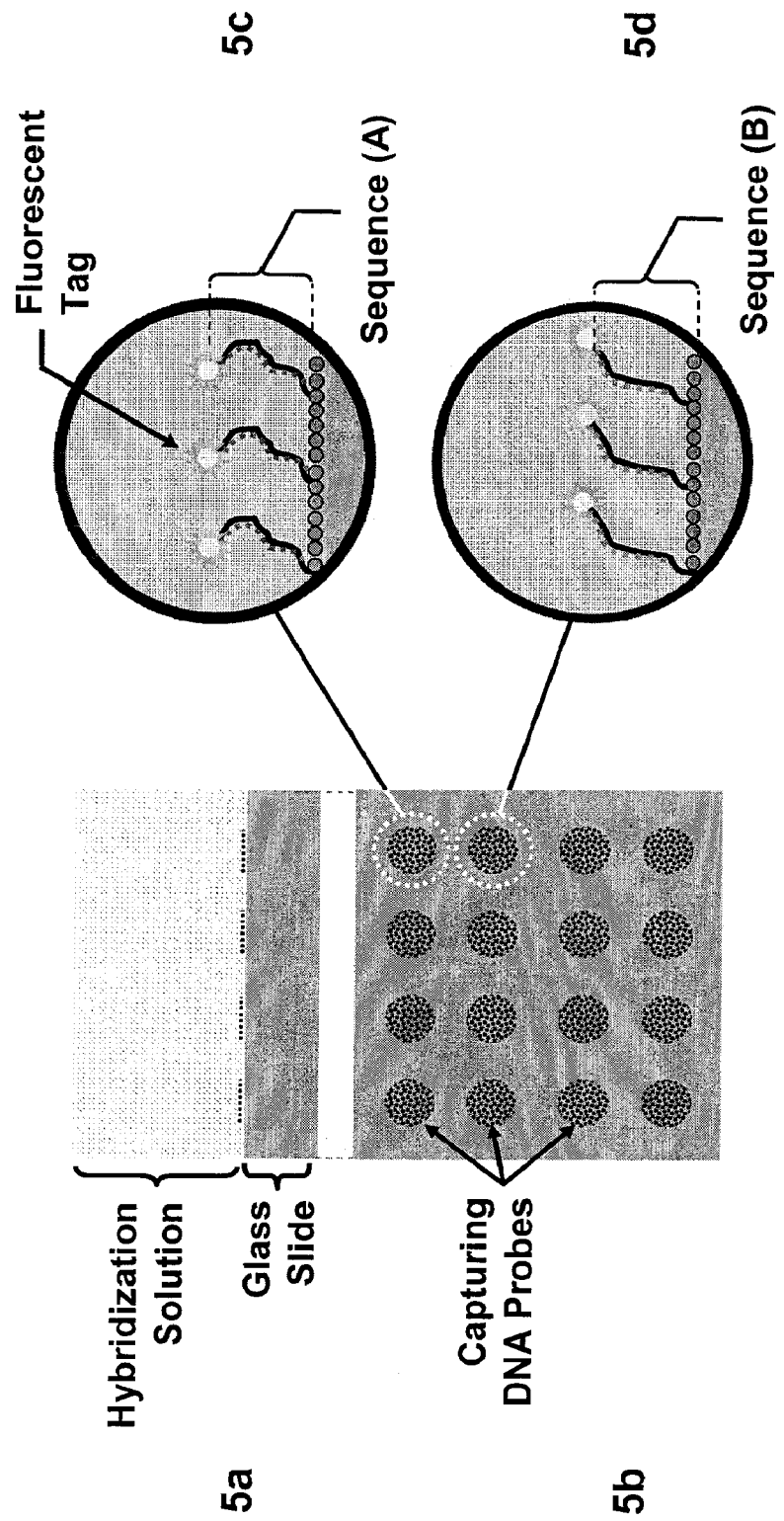
FIG. 9 shows a real-time array of the present invention where the probes are labeled with fluorescent moieties.
Figure 10:
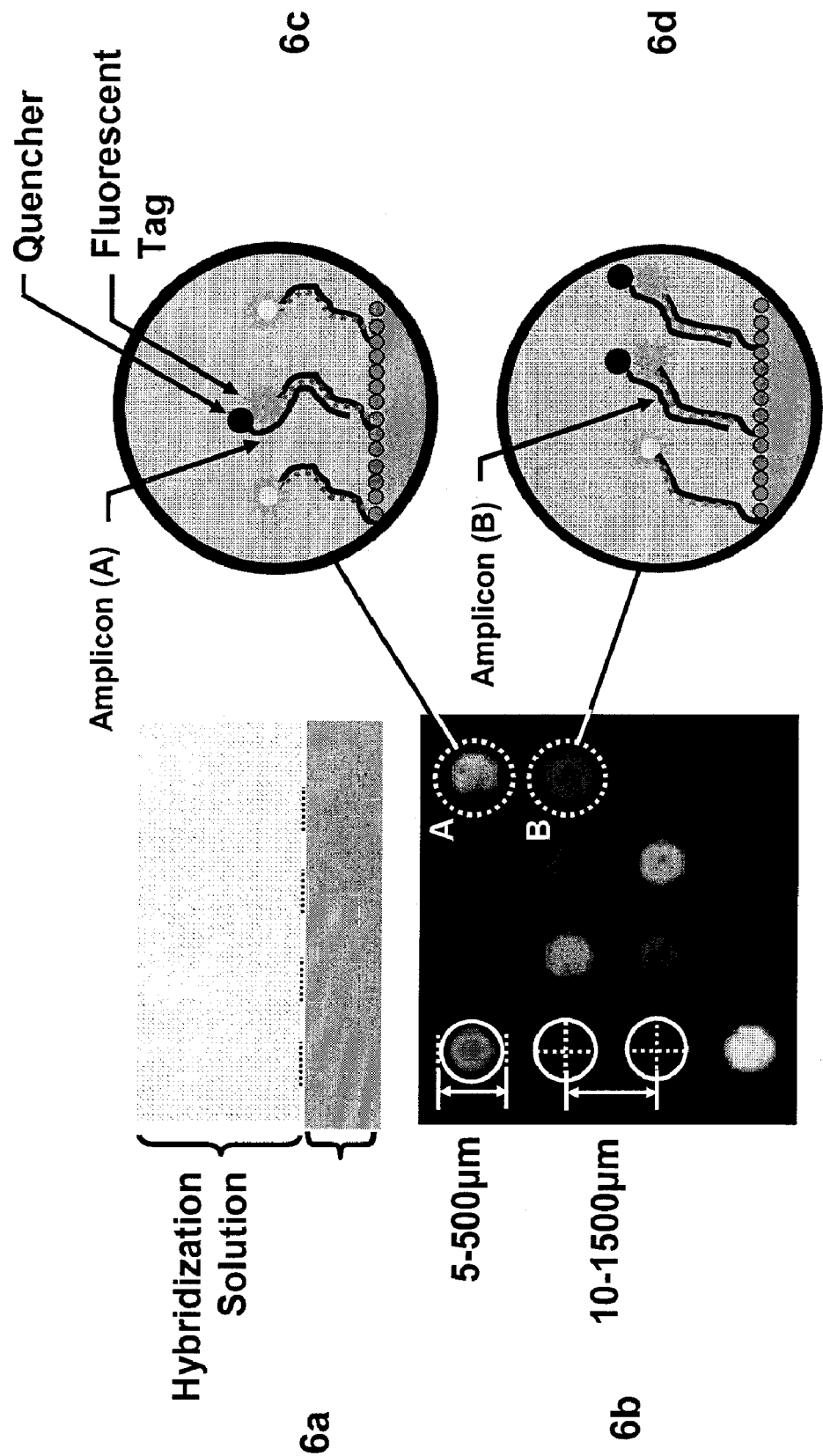
FIG. 10 shows a real-time array of the present invention where the probes are labeled with fluorescent moieties, the amplicons are labeled with quenchers, and the fluorescent intensity on various spots can be used to measure the amount of amplicon specifically bound to probe.

One exemplary embodiment of a real-time microarray useful for carrying out the method of the invention is shown in FIGS. 9 and 10. FIG. 9B shows a top view of a 4 by 4 microarray that has 16 independently addressable spots, each spot having bound DNA probes, wherein the probes are labeled with fluorescent label. FIG. 9C shows a close up view of one of the spots illustrating the attached probe of sequence (A), each probe having a fluorescent label. FIG. 9D shows the close up view of a second spot with attached probes of sequence (B), each probe having a fluorescent label. FIG. 9A shows a side view of the array, showing that the array is in contact with the hybridization solution. FIG. 9 represents a time at which no amplicon is bound to probe on the array.

FIG. 10 illustrates the same array as in FIG. 9 after hybridization for some time with amplicons having a quencher attached. FIGS. 10A and 10B shows a side view and top view of the array, still in contact with the hybridization solution. The different spots on the array in FIG. 10B have different light intensities, indicating that there is a different amount of binding of amplicon at each spot, and therefore a different amount of fluorescence from the spots. FIG. 10C shows a close up view illustrating that a small amount of amplicon (A) has specifically bound (hybridized) to probe (A) resulting in quenching of each molecule of probe to which analyte is bound. FIG. 10D illustrates that a larger amount of amplicon (B) has specifically bound (hybridized) to probe (B), resulting in a higher level of quenching than observed for spot (A). The signal from each of the spots on the array can be measured at various time points during the binding reaction between analytes and probes, while the solution containing the analyte is in contact with the solid surface of the microarray, allowing a real-time measurement of the amount of analyte-probe binding, and allowing the measurement of binding kinetics at each spot.

The methods of the invention can be used to measure the presence or amount of nucleotide sequences in samples at low levels. In some embodiments, the presence or amount of nucleic acid can be measured where the nucleic acid is present in a sample at the level of nanomoles, picomoles, femtomoles. In some cases it can determine the presence or amount of nucleotide sequences down to a single molecule.

Nucleic Acid Amplification

One aspect of the invention relates to performing a nucleic acid amplification on two or more nucleotide sequences to produce two or more amplicons in a fluid that is in contact with an array of probes. The amplification of a nucleotide sequence can be performed by any method of amplification. Methods of amplification include, for example: polymerase chain reaction (PCR), strand displacement amplification (SDA), and nucleic acid sequence based amplification (NASBA), and Rolling Circle Amplification (RCA).

The polymerase chain reaction (PCR) is widely used and described, and involves the use of primer extension combined with thermal cycling to amplify a target sequence; see U.S. Pat. Nos. 4,683,195 and 4,683,202. In addition, there are a number of variations of PCR which also find use in the invention, including quantitative PCR or Q-PCR, "quantitative competitive PCR" or "QC-PCR", "arbitrarily primed PCR" or "AP-PCR", "immuno-PCR", "Alu-PCR", "PCR single strand conformational polymorphism" or "PCR-SSCP", allelic PCR, "reverse transcriptase PCR" or "RT-PCR", "biotin capture PCR", "vectorette PCR". "panhandle PCR", and "PCR select cDNA subtraction", among others. Strand displacement amplification (SDA) is generally described in Walker et al., in U.S. Pat. Nos. 5,455,166 and 5,130,238. Nucleic acid sequence based amplification (NASBA) is generally described in U.S. Pat. No. 5,409,818.

The amplification method can use temperature cycling or be isothermal. The amplification method can be exponential or linear. For amplifications with temperature cycling, a temperature cycle generally corresponds to an amplification cycle. Isothermal amplifications can in some cases have amplification cycles, such as denaturing cycles, and in other cases, the isothermal amplification reaction will occur monotonically with out any specific amplification cycle.

One aspect of the invention performing PCR amplification on two or more nucleotide sequences to produce two or more amplicons in a fluid that is in contact with an array of probes. PCR is used to amplify specific regions, or nucleotide sequences of a DNA strand. This region can be, for example, a single gene, just a part of a gene, or a non-coding sequence. PCR methods typically amplify DNA fragments of up to 10 kilo base pairs (kb), although some techniques allow for amplification of fragments up to 40 kb in size.

The PCR generally requires several components: (1) The DNA template that contains the region of the nucleic acid sequence to be amplified; (2) one or more primers, which are complementary to the DNA regions at the 5' and 3' ends of the DNA region that is to be amplified; (3) a DNA polymerase (e.g. Taq polymerase or another DNA polymerase with a temperature optimum at around 70° C.), used to synthesize a DNA copy of the region to be amplified; (4) Deoxynucleotide triphosphates, (dNTPs); (5) a buffer solution, which provides a suitable chemical environment for optimum activity and stability of the DNA polymerase; and (6) a divalent cation such as magnesium or manganese ions.

Prior to the first cycle, the reaction can be subjected to a hold step during an initialization step, the PCR reaction can be heated to a temperature of 94-98° C., and this temperature is then held for 1-9 minutes. This first hold is employed to ensure that most of the DNA template and primers are denatured, i.e., that the DNA is melted by disrupting the hydrogen bonds between complementary bases of the DNA strands. In some embodiments a hot-start PCR can be utilized.

Temperature cycling can then begin with one step at, for example, 94-98° C. for e.g. 20-30 seconds (denaturation step). The denaturation is followed by the annealing step. In this step the reaction temperature is lowered so that the primers can anneal to the single-stranded DNA template. The temperature at this step depends on the melting temperature of the primers, and is usually between 50-64° C. for e.g. 20-40 seconds.

The annealing step is followed by an extension/elongation step during which the DNA polymerase synthesizes new DNA strands complementary to the DNA template strands. The temperature at this step depends on the DNA polymerase used. Taq polymerase has a temperature optimum of about 70-74° C.; thus, a temperature of 72° C. may be used. The DNA polymerase condenses the 5'-phosphate group of the dNTPs with the 3'-hydroxyl group at the end of the nascent (extending) DNA strand, i.e., the polymerase adds dNTP's that are complementary to the template in 5' to 3' direction, thus reading the template in 3' to 5' direction. The extension time may depend on both on the DNA polymerase used and on the length of the DNA fragment to be amplified. Thus, in the process described, each temperature cycle has three phases; denaturation, annealing, and elongation. The amplified products from the amplification are referred to as amplicons. Generally, 10-40 cycles, usually 20-30 cycles of PCR are performed.

In some embodiments, the amplification methods of the invention utilize primers. A primer is a nucleic acid strand, or a related molecule that serves as a starting point for DNA replication. A primer is often required because most DNA polymerases cannot begin synthesizing a new DNA strand from scratch, but can only add to an existing strand of nucleotides. The primers of the invention are usually short, chemically synthesized DNA molecules with a length about 10 to about 30 bases. The length of primers can be for example about 20-30 nucleotides, and the sequence of the primers are complementary to the beginning and the end of the DNA fragment to be amplified. They anneal (adhere) to the DNA template at these starting and ending points, where DNA polymerase binds and begins the synthesis of the new DNA strand.

The design of primers is well known in the art. Pairs of primers should generally have the similar melting temperatures (Tm). A primer with a Tm significantly higher than the reaction's annealing temperature may mishybridize and extend at an incorrect location along the DNA sequence, while Tm significantly lower than the annealing temperature may fail to anneal and extend at all.

In some embodiments of the invention, degenerate primers are used. These are actually mixtures of similar, but not identical, primers. Degenerate primers can be used, for example, when primer design is based on protein sequence. As several different codons can code for one amino acid, it is often difficult to deduce which codon is used in a particular case. Therefore primer sequence corresponding to the amino acid isoleucine might be "ATH", where A stands for adenine, T for thymine, and H for adenine, thymine, or cytosine, according to the genetic code for each codon. Use of degenerate primers can greatly reduce the specificity of the PCR amplification.

In some embodiments of the invention, the primers are labeled, and the labels become incorporated into the amplicons formed by such primers. The primers can be labeled with one or more labels that are for example fluorescent, quenchers, or members of a FRET pair. Methods of attaching these moieties to primers is well known in the art.

One aspect of the invention is an array of probes that is in fluid contact with an amplification reaction in which multiple amplicons are formed with multiple primer sets. The array of probes in fluid contact with the amplification reaction allows for the quantitation of the amount of amplicon generated at each cycle. As with Q-PCR, the amount of amplicon generated at each cycle can be plotted against the number of cycles, which can be used to accurately determine the amount of nucleic acid sequence from which the amplicons were generated.

Figure 11:
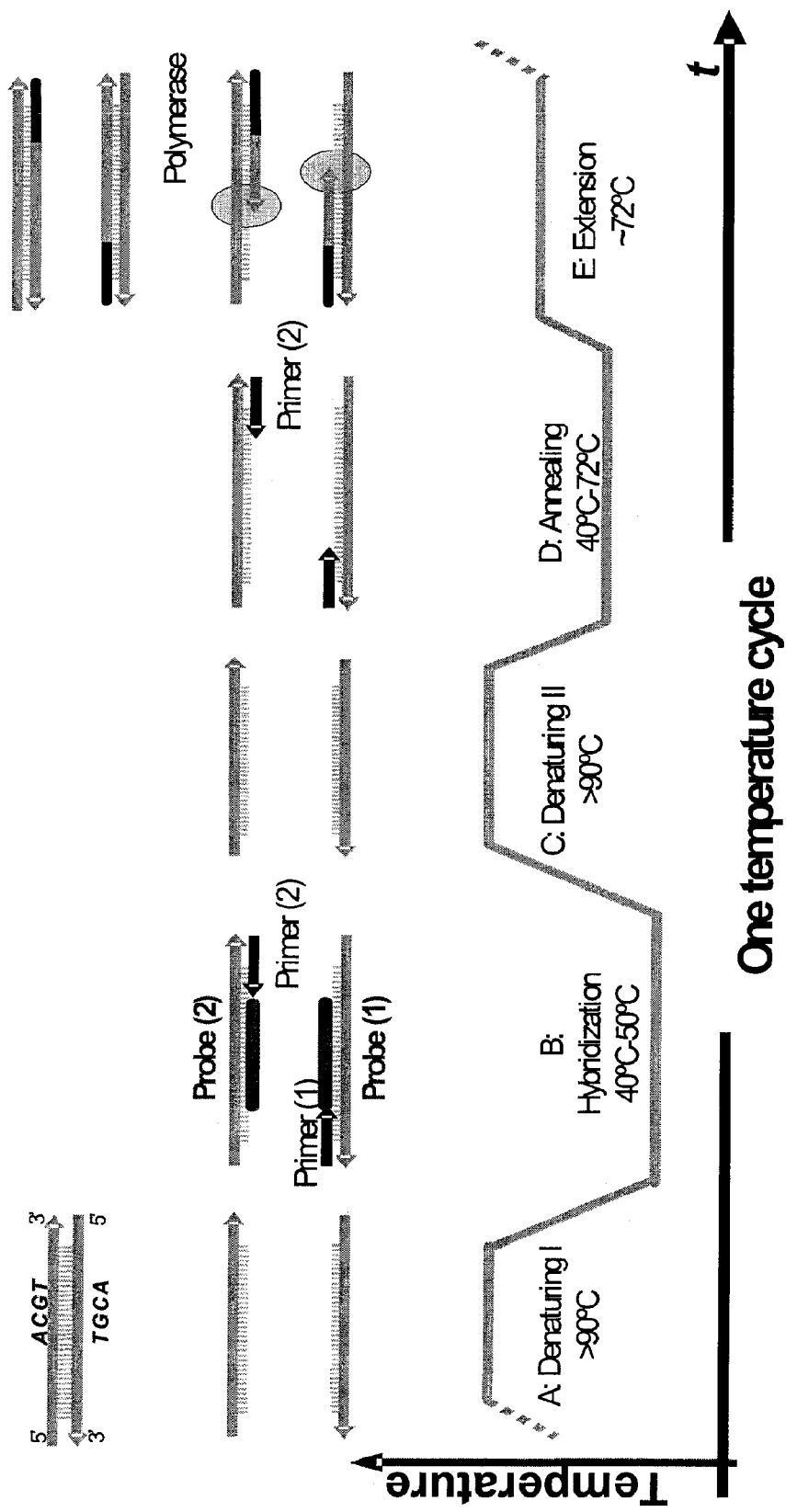
FIG. 11 shows an embodiment of a temperature cycle of the present invention where the temperature cycle has 5 phases.

The measurement of the amount of amplicon during or after each cycle is facilitated by measuring the hybridization kinetics of the amplicons to the probes on the array. In some embodiments, the rate of hybridization of the amplicon to the probe is measured during the annealing phase, the denaturing phase or the elongation phase. In a three phase PCR, typically, the rate of amplicon hybridization to probe is measured during the annealing phase of the PCR temperature cycle, where the rate of going from unbound to bound amplicon can be measured and the rate can be correlated with the concentration of the analytes in the fluid. Measuring binding during the denaturing phase can allow the determination of the "off" rate the amplicons. In some embodiments, more than 3 temperature phases are used within a temperature cycle, and the separate temperature phases can be used do define specific hybridization conditions. For example, as shown in FIG. 11, a 5 phase temperature cycle can be used. The 5 phase temperature cycle shown in FIG. 11 has 3 phases that are similar to the 3 phases of a conventional PCR, and in addition, there is another denaturing phase followed by a hybridization phase. In this embodiment, the kinetics of amplicon hybridization is measured during the hybridization phase. The 5 phase method allows the hybridization phase to be optimized for measuring amplicon binding, while the annealing phase is optimized for primer annealing. In some embodiments, the temperature of the hybridization phase is lower than the temperature of the annealing phase. In some embodiments, the temperature of the hybridization phase is higher than that of the annealing phase.

In some embodiments, 3, 4, 5, 6 or more phases can be used. For example, in some embodiments, the hybridization phase can comprise multiple temperatures, allowing several hybridization conditions to be measured during one amplification cycle. In some cases, the number of phases can vary over the amplification, for example using a 3 phase cycle in some cycles, and a 5 phase cycle in others.

In some embodiments, amplicon hybridization is measured after every cycle. In some embodiments, amplicon hybridization is measured at some but not all of the amplification cycles. For example, in some embodiments, the first several cycles to about 10 cycles may provide little information because the level of amplicon is below the detection threshold, and in such cases, hybridization at few or none of the earlier cycles may be measured, while in the later cycles, hybridization at every cycle or almost every cycle may be measured. In contrast, the data during the exponential phase of amplification can yield the most useful data, and in this region, the amplicon hybridization may be measured during of after every or almost every cycle. In some embodiments, amplicon hybridization is measured on average during or after every 2, 3, 4, 5, 6, 7, 8, 9, or 10 amplification cycles.

One aspect of the invention is a method for performing multiplex quantitative PCR comprising (a) measuring the amount of 10 or more amplicons corresponding to 10 or more different nucleotide sequences in a single fluid volume during or after multiple amplification cycles to determine amplicon amount-amplification cycle values, and (b) using the amplicon amount-amplification cycle values to determine the presence or amount of the 10 or more nucleotide sequences in a sample. In some embodiments, the invention provides a method of performing multiplex PCR of 20 or more amplicons corresponding to 20 or more different nucleotide sequences are used to determine the amount of 20 or more nucleotide sequences. In some embodiments, the invention provides a method of performing multiplex PCR of 50 or more amplicons corresponding to 50 or more different nucleotide sequences are used to determine the amount of 50 or more nucleotide sequences. Multiplex Q-PCR refers to a quantitative PCR reaction wherein the concentration of more than one amplicon corresponding to more than one nucleic acid sequence is measured in the same amplification reaction in the same fluid volume. It is known in the art, for instance, that real-time PCR or Q-PCR systems can incorporate detector dyes with different emission wavelengths, such that each dye can be detected in the same solution. These prior art method can be used for a small number of different amplicons, but are limited by the overlap of the fluorescent emission spectra. It is also known in the art, that where there are a larger number of amplicons, to split the sample into a number of different wells, for instance on a plate, and perform Q-PCR on the plate at one time in order to amplify the sample in each well of the plate. The present invention allows for larger numbers of amplicons, and therefore a larger number of nucleic acid sequences to be measured in the same amplification reaction in the same fluid. The present invention allows for example for a multiplex quantitative PCR reaction of greater that 10, 20, 50, 100, 200, 500, 1,000, 2,000, 5,000, 10,000, 50,000, 100,000, 500,000, 1,000,000 or more nucleic acid sequences in the same amplification reaction in the same fluid.

One aspect of the methods of the present invention includes the step of performing an algorithm on real-time binding data to determine cross-hybridization of amplicons for multiple probes on a substrate. One embodiment involves improving the quality of analyte-probe binding measurements by determining and correcting for cross-hybridization. Algorithms for determining cross-hybridization are described in U.S. patent Ser. No. 11/758,621, incorporated herein by reference.

Arrays

One aspect of the invention is an array that has a solid surface with a plurality of probes attached to it, where the array can be used for the real-time measurement of binding of amplicons to the plurality of probes.

The arrays of the present invention comprise probes attached to a solid substrate. The solid substrate may be biological, nonbiological, organic, inorganic, or a combination of any of these, existing as particles, strands, precipitates, gels, sheets, tubing, spheres, containers, capillaries, pads, slices, films, plates, slides, semiconductor integrated chips, etc. The solid substrate is preferably flat but may take on alternative surface configurations. For example, the solid substrate may contain raised or depressed regions on which synthesis or deposition takes place. In some embodiments, the solid substrate will be chosen to provide appropriate light-absorbing characteristics. For example, the substrate may be a polymerized Langmuir Blodgett film, functionalized glass, Si, Ge, GaAs, Gap, $SiO_2$, $SiN_4$, modified silicon, or any one of a variety of gels or polymers such as (poly)tetrafluoroethylene, (poly)vinylidenedifluoride, polystyrene, polycarbonate, or combinations thereof.

The substrate can be a homogeneous solid and/or unmoving mass much larger than the capturing probe where the capturing probes are confined and/or immobilized within a certain distance of it. The mass of the substrate is generally at least 100 times larger than capturing probes mass. In certain embodiments, the surface of the substrate is planar with roughness of 0.1 nm to 100 nm, but typically between 1 nm to 100 nm. In other embodiments the substrate can be a porous surface with roughness of larger than 100 nm. In other embodiments, the surface of the substrate can be non-planar. Examples of non-planar substrates are spherical magnetic beads, spherical glass beads, and solid metal and/or semiconductor and/or dielectric particles. As used herein, the term array and the term microarray are used interchangeably.

In some embodiments the substrate is optically clear, allowing light to be transmitted through the substrate, and allowing excitation and or detection to occur from light passing through the substrate. In some embodiments the substrate is opaque. In some embodiments, the substrate is reflective, allowing for light to pass through the surface layer containing probes and reflect back to a detector.

In some embodiments, the array is incorporated into the fluid container in which the amplification reaction will take place. In some cases, the array is part of the wall or base of the container. In some cases the array mates with other elements, forming a seal, and creating a fluid container for carrying out the amplification reaction.

In some embodiments, glass slides are used to prepare biochips. The substrates (such as films or membranes) can also be made of silica, silicon, plastic, metal, metal-alloy, anopore, polymeric, and nylon. The surfaces of substrates can be treated with a layer of chemicals prior to attaching probes to enhance the binding or to inhibit non-specific binding during use. For example, glass slides can be coated with self-assembled monolayer (SAM) coatings, such as coatings of as aminoalkyl silanes, or of polymeric materials, such as acrylamide and proteins. A variety of commercially available slides can be used. Some examples of such slides include, but are not limited to, 3D-link® (Surmodics), EZ-Rays® (Mosaic Technologies), Fastslides® (Schleicher and Schuell), Superaldehyde®, and Superamine® (CEL Technologies).

Probes can be attached covalently to the solid surface of the substrate (but non-covalent attachment methods can also be used).

A number of different chemical surface modifiers can be added to substrates to attach the probes to the substrates. Examples of chemical surface modifiers include N-hydroxy succinimide (NHS) groups, amines, aldehydes, epoxides, carboxyl groups, hydroxyl groups, hydrazides, hydrophobic groups, membranes, maleimides, biotin, streptavidin, thiol groups, nickel chelates, photoreactive groups, boron groups, thioesters, cysteines, disulfide groups, alkyl and acyl halide groups, glutathiones, maltoses, azides, phosphates, and phosphines. Glass slides with such chemically modified surfaces are commercially available for a number of modifications. These can easily be prepared for the rest, using standard methods (Microarray Biochip Technologies, Mark Schena, Editor, March 2000, Biotechniques Books).

In one embodiment, substrate surfaces reactive towards amines are used. An advantage of this reaction is that it is fast, with no toxic by-products. Examples of such surfaces include NHS-esters, aldehyde, epoxide, acyl halide, and thio-ester. Most proteins, peptides, glycopeptides, etc. have free amine groups, which will react with such surfaces to link them covalently to these surfaces. Nucleic acid probes with internal or terminal amine groups can also be synthesized, and are commercially available (e.g., from IDT or Operon). Thus, nucleic acids can be bound (e.g., covalently or non-covalently) to surfaces using similar chemistries.

The substrate surfaces need not be reactive towards amines, but many substrate surfaces can be easily converted into amine-reactive substrates with coatings. Examples of coatings include amine coatings (which can be reacted with bis-NHS cross-linkers and other reagents), thiol coatings (which can be reacted with maleimide-NHS cross-linkers, etc.), gold coatings (which can be reacted with NHS-thiol cross linkers, etc.), streptavidin coatings (which can be reacted with bis-NHS cross-linkers, maleimide-NHS cross-linkers, biotin-NHS cross-linkers, etc.), and BSA coatings (which can be reacted with bis-NHS cross-linkers, maleimide-NHS cross-linkers, etc.). Alternatively, the probes, rather than the substrate, can be reacted with specific chemical modifiers to make them reactive to the respective surfaces.

A number of other multi-functional cross-linking agents can be used to convert the chemical reactivity of one kind of surface to another. These groups can be bifunctional, tri-functional, tetra-functional, and so on. They can also be homo-functional or hetero-functional. An example of a bi-functional cross-linker is X-Y-Z, where X and Z are two reactive groups, and Y is a connecting linker. Further, if X and Z are the same group, such as NHS-esters, the resulting cross-linker, NHS—Y—NHS, is a homo-bi-functional cross-linker and would connect an amine surface with an amine-group containing molecule. If X is NHS-ester and Z is a maleimide group, the resulting cross-linker, NHS—Y-maleimide, is a hetero-bi-functional cross-linker and would link an amine surface (or a thiol surface) with a thio-group (or amino-group) containing probe. Cross-linkers with a number of different functional groups are widely available. Examples of such functional groups include NHS-esters, thio-esters, alkyl halides, acyl halides (e.g., iodoacetamide), thiols, amines, cysteines, histidines, di-sulfides, maleimide, cis-diols, boronic acid, hydroxamic acid, azides, hydrazines, phosphines, photoreactive groups (e.g., anthraquinone, benzophenone), acrylamide (e.g., acrydite), affinity groups (e.g., biotin, streptavidin, maltose, maltose binding protein, glutathione, glutathione-S-transferase), aldehydes, ketones, carboxylic acids, phosphates, hydrophobic groups (e.g., phenyl, cholesterol), etc. Such cross-linkers can be reacted with the surface or with the probes or with both, in order to conjugate a probe to a surface.

Other alternatives include thiol reactive surfaces such as acrylate, maleimide, acyl halide and thio-ester surfaces. Such surfaces can covalently link proteins, peptides, glycopeptides, etc., via a (usually present) thiol group. Nucleic acid probes containing pendant thiol-groups can also be easily synthesized.

Alternatively, one can modify glass surfaces with molecules such as polyethylene glycol (PEG), e.g. PEGs of mixed lengths.

Other surface modification alternatives (such as photo-crosslinkable surfaces and thermally cross-linkable surfaces) are known to those skilled in the art. Some technologies are commercially available, such as those from Mosiac Technologies (Waltham, Mass.), Exiqon™ (Vedbaek, Denmark), Schleicher and Schuell (Keene, N.H.), Surmodics™ (St. Paul, Minn.), Xenopore™ (Hawthorne, N.J.), Pamgene (Netherlands), Eppendorf (Germany), Prolinx (Bothell, Wash.), Spectral Genomics (Houston, Tex.), and Combimatrix™ (Bothell, Wash.).

Surfaces other than glass are also suitable for such devices. For example, metallic surfaces, such as gold, silicon, copper, titanium, and aluminum, metal oxides, such as silicon oxide, titanium oxide, and iron oxide, and plastics, such as polystyrene, and polyethylene, zeolites, and other materials can also be used. The devices can also be prepared on LED (Light Emitting Diode) and OLED (Organic Light Emitting Diode) surfaces. An array of LEDs or OLEDs can be used at the base of a probe array. An advantage of such systems is that they provide easy optoelectronic means of result readout. In some cases, the results can be read-out using a naked eye.

Probes can be deposited onto the substrates, e.g., onto a modified surface, using either contact-mode printing methods using solid pins, quill-pins, ink-jet systems, ring-and-pin systems, etc. (see, e.g., U.S. Pat. Nos. 6,083,763 and 6,110,426) or non-contact printing methods (using piezoelectric, bubble-jet, syringe, electro-kinetic, mechanical, or acoustic methods. Devices to deposit and distribute probes onto substrate surfaces are produced by, e.g., Packard Instruments. There are many other methods known in the art. Preferred devices for depositing, e.g., spotting, probes onto substrates include solid pins or quill pins (Telechem/Biorobotics).

The arrays of the present invention can also be three-dimensional arrays such as porous arrays. Such as devices consisting of one or more porous gel-bound probes in an array or an array of arrays format. A device can have one or more such structures and the structures can be of any geometric shape and form. The structures can also be vertically straight, angled, or twisted. Thus, each device denotes a (multiplexed) reaction site. The device can be used to perform reactions simultaneously or sequentially. Any of the known substrates and chemistries can be used to create such a device. For example, glass, silica, silicon wafers, plastic, metals; and metal alloys can all be used as the solid support (see. e.g., Stillman B A, Tonkinson J L, Scleicher and Schuell; Biotechniques, 29(3), 630-635, 2000; Rehmna et. al; Mosaic Technologies Inc., Nucleic Acids Research, 27(2), 649-655, 1999). In other embodiments, the intermediate species can be immobilized to the substrate using mechanical and/or electrostatic and/or and magnetic forces. Examples are magnetic beads with magnetic fields and glass beads with electrostatic fields. Bead based methods are described, for example in Gunderson et al., Genome Research, 870-877, 2004.

In other embodiments, the microarrays are manufactured through the in-situ synthesis of the probes. This in-situ synthesis can be achieved using phosphoramidite chemistry and/or combinatorial chemistry. In some cases, the deprotection steps are performed by photodeprotection (such as the Maskless Array Synthesizer (MAS) technology, (NimbleGen,; or the photolithographic process, by Affymetrix). In other cases, deprotection can be achieved electrochemically (such as in the Combimatrix procedure). Microarrays for the present invention can also be manufactured by using the inkjet technology (Agilent).

For the arrays of the present invention, the plurality of probes are located on multiple addressable regions on the solid substrate. In some embodiments the solid substrate has about 2, 3, 4, 5, 6, or 7-10, 10-50, 50-100, 100-500, 500-1,000, 1,000-5,000, 5,000-10,000, 10,000-50,000, 50,000-100,000, 100,000-500,000, 500,000-1,000,000 or over 1,000,000 addressable regions with probes.

The spots may range in size from about 1 nm to 10 mm, in some embodiments from about 1 to 1000 micron and more in some embodiments from about 5 to 100 micron. The density of the spots may also vary, where the density is generally at in some embodiments about 1 spot/cm$^2$, in some embodiments at least about 100 spots/cm$^2$ and in other embodiments at least about 400 spots/cm$^2$, where the density may be as high as $10^6$ spots/cm$^2$ or higher.

The shape of the spots can be square, round, oval or any other arbitrary shape.

In some embodiments, the optical signal moiety, for example, a fluorescent moiety is bound directly to the surface, but is not covalently bound to a probe, and in these cases the probe need not be labeled. The fluorescent moiety can be bound to the surface or synthesized in-situ by any of the methods described above for probes. The fluorescent moiety can be attached to an oligonucleotide that is not a probe, for example, having a sequence that is not complementary to target amplicons in solution.

In some embodiment, a fluorescent moiety on the surface (surface-bound label) can be brought to the proximity of the probe via post-probe-synthesis or post-probe-deposition methods.

In some embodiments, the label can be bound to the probe by non-covalent means, such as by hybridization. For example, in certain embodiments of the present invention, some or all of the probes on the microarray may contain two different sequence segments: one segment that consists of a sequence that is specific to the probe and specific for the detection of a given target amplicon, and another segment that is a sequence that is common to all or many of the probes on the microarray. These two sequence segments can be immediately adjacent to each other on the probe, or separated by a linker. In this embodiment, the microarray is first hybridized with a (labeled oligonucleotide that is complementary to the common sequence segment, thus resulting in a microarray in which the spots or features where the probes are located also now contain fluorescent labels. These non-covalently bound labels can be bound to the probe such that FRET and or quenching of the label occurs upon binding of an amplicon to the specific portion of the probe. This method can be advantageous, for instance by (1) lowering the cost of manufacturing microarrays that can be used in the real-time platform and/or (2) enabling the use of in-situ synthesized arrays in the real time platform. The labeled oligonucleotide can be a locked nucleic acid (LNA) oligonucleotide. LNA oligonucleotides can be useful because the LNA modification can result in enhanced hybridization properties (for example, diminishing the sequence length that is needed to achieve a certain Tm) (Jepsen et al., Oligonucleotides. 2004; 14(2):130-46).

Systems

One aspect of the invention is a system comprising: (a) a PCR amplification reaction chamber capable of receiving: (i) a substrate comprising a surface with an array of nucleic acid probes at independently addressable locations, and (ii) a fluid to be held contact with the substrate, the fluid comprising a nucleic acid sample comprising multiple nucleotide sequences, primers, and enzymes; (b) a temperature controller capable of carrying out multiple PCR temperature phases and temperature cycles comprising: (i) a heating and cooling module for raising and lowering the temperature of the fluid and/or the substrate; and (ii) a temperature sensor; and (c) a detector capable of detecting light signals as a function of time from the independently addressable locations on the substrate within the chamber at a specific phase or phases during or after a plurality of temperature cycles while the fluid is in contact with the substrate. In some embodiments, the system further comprises: (d) an analysis block comprising a computer and software capable of determining the amounts of amplified products hybridized to the array of probes using the detected light as a function of time, and of determining the amounts of multiple nucleotide sequences in a sample using the amounts of amplified products determined during or after a plurality of temperature cycles.

The fluid volume can be introduced and held in the system by any method that will maintain the fluid in contact with the solid support. In many cases the fluid is held in a chamber. In some embodiments the chamber is open on one face, in other embodiments the chamber will mostly enclose the fluid. In some embodiments, the chamber will have one or more ports for introducing and/or removing material (usually fluids)

from the chamber. In some embodiments one side of the chamber comprises the solid substrate on which the probes are attached. In some embodiments the chamber is integral to the solid substrate. In some embodiments, the chamber is a sub-assembly to which the solid substrate with probes can be removably attached. In some embodiments, some or all of the fluid chamber is an integral part of the instrument that comprises the detector. The chamber can be designed such that the signal that can be correlated with amplicon-probe binding can be detected by a detector outside of the chamber. For instance, all or a portion of the chamber can be transparent to light to allow light in or out of the chamber to facilitate excitation and detection of fluorophores.

The system can incorporate one or more microfluidic devices. Microfluidic devices are fluid systems in which the volumes of fluid are small, typically on the order of microliters to nanoliters. In some embodiments the microfluidics can handle tens to thousands of samples in small volumes. Microfluidics used in the invention can be active or passive. By using active elements such as valves in the microfluic device, microfluidic circuits can be created. This allows not only the use of small reagent volumes but also a high task parallelization since several procedures can processed and physically be fitted on the same chip.

In microfluidic channels the flow of liquid can be completely laminar, that is, all of the fluid moves in the same direction and at the same speed. Unlike turbulent flow this allows the transport of molecules in the fluid to be very predictable. The microfluidic devices useful in the invention can be made of glass or plastic. In some embodiments, polydimethylsiloxane (PDMS), a type of silicone can be used. Some advantages of PDMS are that it is inexpensive, optically clear and permeable to several substances, including gases. In some embodiments soft lithography or micromolding can be used to create PDMS based microfluidic devices. The devices can use pressure driven flow, electrodynamic flow, or wetting driven flow.

In some embodiments the microfluidic device has multiple chambers, each chamber having a real-time microarray. In some embodiments, the array is incorporated into the microfluidic device. In some embodiments, the microfluic device is formed by adding features to a planar surface having multiple real-time microarrays in order to create chambers wherein the chamber correspond to the real-time microarray. In some embodiments, a substrate having 3-dimensional features, for example a PDMS surface with wells and channels, is placed in contact with a surface having multiple real-time microarrays to form a microfluidic device having multiple arrays in multiple chambers.

A device having multiple chambers, each with a real-time microarray can be used in order to analyze multiple samples simultaneously. In some embodiments, multiple chambers have sample fluid derived from the same sample. Having sample fluid from the same sample in multiple chambers can be useful, for example to measure each with different arrays for analyzing different aspects of the same sample, or for example for increasing accuracy by parallel measurements on identical arrays. In some cases, different amplicons within the same sample will have different optimum temperature profile conditions. Thus, in some embodiments, the same sample is divided into different fluid volumes, and the different fluid volumes are in different chambers with real-time microarrays; and at least some of the different fluid volumes are given a different temperature cycle.

In some embodiments, multiple chambers have sample fluid from different sources. Having sample fluid from different sources can be useful in order to increase throughput by measuring more samples in a given time period on a given instrument. In some embodiments, the microfluidic with multiple chambers containing real-time microarrays can be used for diagnostic applications. The device may have about 2, 3, 4, 5, 6, 7, 8, 9, 10, 10-15, 15-20, 20-30, 30-50, 50-75, 75-100, or more than 100 chambers each having a real time microarray.

The detector assembly can comprise a single detector or an array of detectors or transducers. As used herein, the terms detector and transducer are used interchangeably, and refer to a component that is capable of detecting a signal that can be correlated with the amount of amplicon-probe binding. Where the detector system is an array of transducers, in some embodiments, the detector system is a fixed array of transducers, wherein one or more transducers in the transducer array corresponds to one independently addressable area of the array. In some embodiments, the detector or the array of transducers scans the array such that a given detector or transducer element detects signals from different addressable areas of the array during a binding reaction.

In some embodiments the detector array is in contact with the solid substrate. In some embodiments, the detector is at a distance away from the substrate. Where the detector is a distance away from the substrate, in some embodiments, the detector or detector array is capable of scanning the substrate in order to measure signal from multiple addressable areas. In some embodiments, the detector is an optical detector which is optically coupled to the substrate. The detector can be optically coupled to the substrate, for example with one or more lenses or waveguides.

Figure 12:
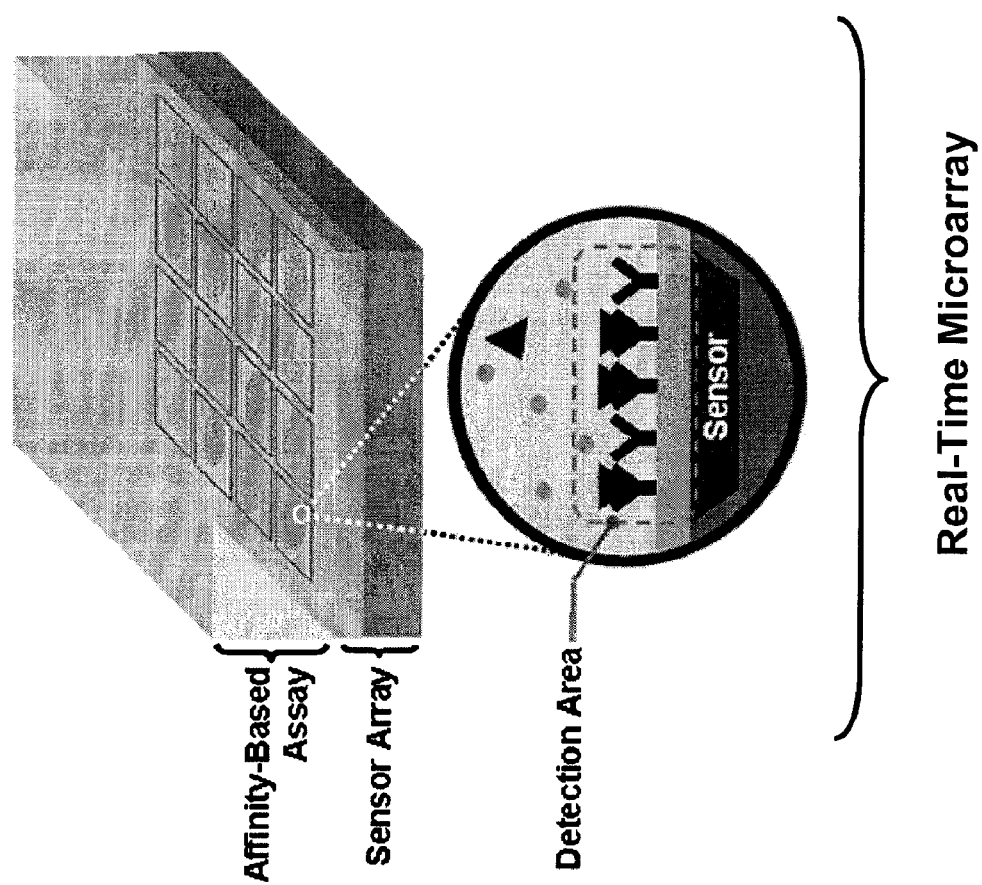
FIG. 12 shows a real-time microarray system where the detection system comprises a sensor array in intimate proximity of the capturing spots.

FIG. 12 shows an example of a real-time microarray system where the detection system comprises a sensor array in intimate proximity of the capturing spots. In this embodiment, individual sensors detect the binding events of a single capturing spots.

In some embodiments, the detector is optically coupled through spatially confined excitation. This method is useful to optically couple the substrate to detector for a small region of substrate with probes. This method generally requires only a single detector, since only one region can create signal at a time. The method can be used in scanning systems, and is applicable in assays which an excitation is required for detection, such as fluorescence spectroscopy or surface plasmon resonance (SPR) methods.

In some embodiments, the detector is optically coupled through imaging using focal plane detector arrays: In this method the signal generated from the system is focused on a focal point detector array. This approach useful for optical detection systems where signal focusing can be carried out using lenses and other optical apparatus. Examples of detectors in these embodiments are complementary metal oxide semiconductor (CMOS) and charge coupled device (CCD) image sensors.

In some embodiments, the detector is optically coupled through surface imaging: In this method the detectors are placed in intimate proximity of the capturing probes such that the signal generated from the capturing region can only be observed by the dedicated detector. If a microarray with multiple capturing spots is used, multiple detectors are used, each dedicated to an individual spot. This method can be used in electrochemical-, optical-, and magnetic-based biosensors.

In some embodiments, the detector is optically coupled through surface imaging using signal couplers: In this method the detectors are not place in proximity of the capturing spots, however a signal coupler is used to direct signal from the capturing region to a detector. This method is generally used in optical detection systems where the signal coupling elements is a plurality of optical waveguide. Examples of signal coupling elements include fiber optic cables, fiber optic bundles, fiber optic faceplates, and light pipes.

Were a microfluidic device with multiple chambers, each chamber containing a real-time microarray is used, the instrument can have one detection device that measures multiple arrays, or each chamber can have its own detector or its own set of detectors.

The detectors of the present invention must be capable of capturing signal at multiple time points in real time, during the binding reaction. In some embodiments the detector is capable of measuring at least two signals in less than about 1 psec, 5 psec, 0.01 nsec, 0.05 nsec, 0.1 nsec, 0.5 nsec, 1 nsec, 5 nsec, 0.01 µsec, 0.05 µsec, 0.1 µsec, 0.5 µsec, 1 µsec, 5 µsec, 0.01 msec, 0.05 msec, 0.1 msec, 0.5 msec, 1 msec, 5 msec, 10 msec, 50 msec, 100 msec, 0.5 sec, 1 sec, 5 sec, 10 sec, or 60 sec.

In some embodiments the detector detects the signal at the substrate. In some embodiments the detector will detect the signal in the solution. In some embodiments, the detector will detect signal in both the solution and at the substrate.

In some embodiments the detector system is capable of detecting electrical, electrochemical, magnetic, mechanical, acoustic, or electromagnetic (light) signals.

Where the detector is capable of detecting optical signals, the detector can be, for example a photomultiplier tube (PMT), a CMOS sensor, or a (CCD) sensor. In some embodiments, the detector comprises a fiber-optic sensor.

In some embodiments, the system comprising the detector is capable of sensitive fluorescent measurements including synchronous fluorimetry, polarized fluorescent measurements, laser induced fluorescence, fluorescence decay, and time resolved fluorescence.

In some embodiments, the system comprises a light source, for example, for excitation of fluorescence. The light source is generally optically coupled to the substrate, for example with one or more lenses or waveguides. The light source can provide a single wavelength, e.g. a laser, or a band of wavelengths.

Figure 13:
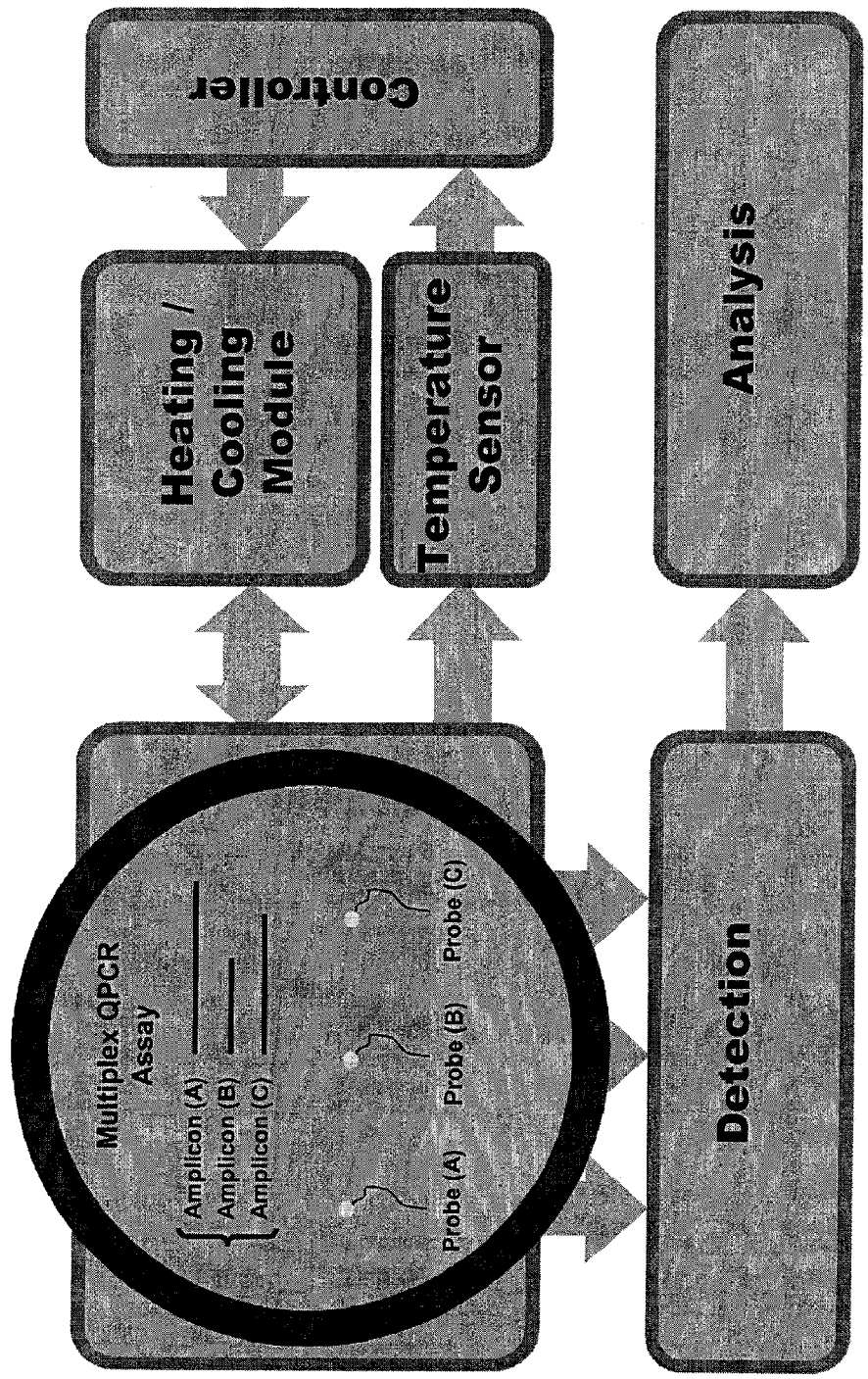
FIG. 13 shows a block diagram of a real-time microarray system of the present invention.

FIG. 13 shows a block diagram of the components of an embodiment of a multiplex Q-PCR system of the present invention. The system comprises of (a) reaction chamber which includes the microarray substrate with probes where the probes are designed for binding with a multiplicity of amplicons generated in the amplification reaction in the chamber (here, probes A, B, and C, on separate addressable locations are capable of specifically binding to amplicons A, B, and C respectively); (b) a temperature controller comprising: (i) a heating and cooling module and (ii) a temperature sensor; and (c) detector, the detector optionally connected to (d) an analysis block, where the latter is a part of a computing system.

Figure 14:
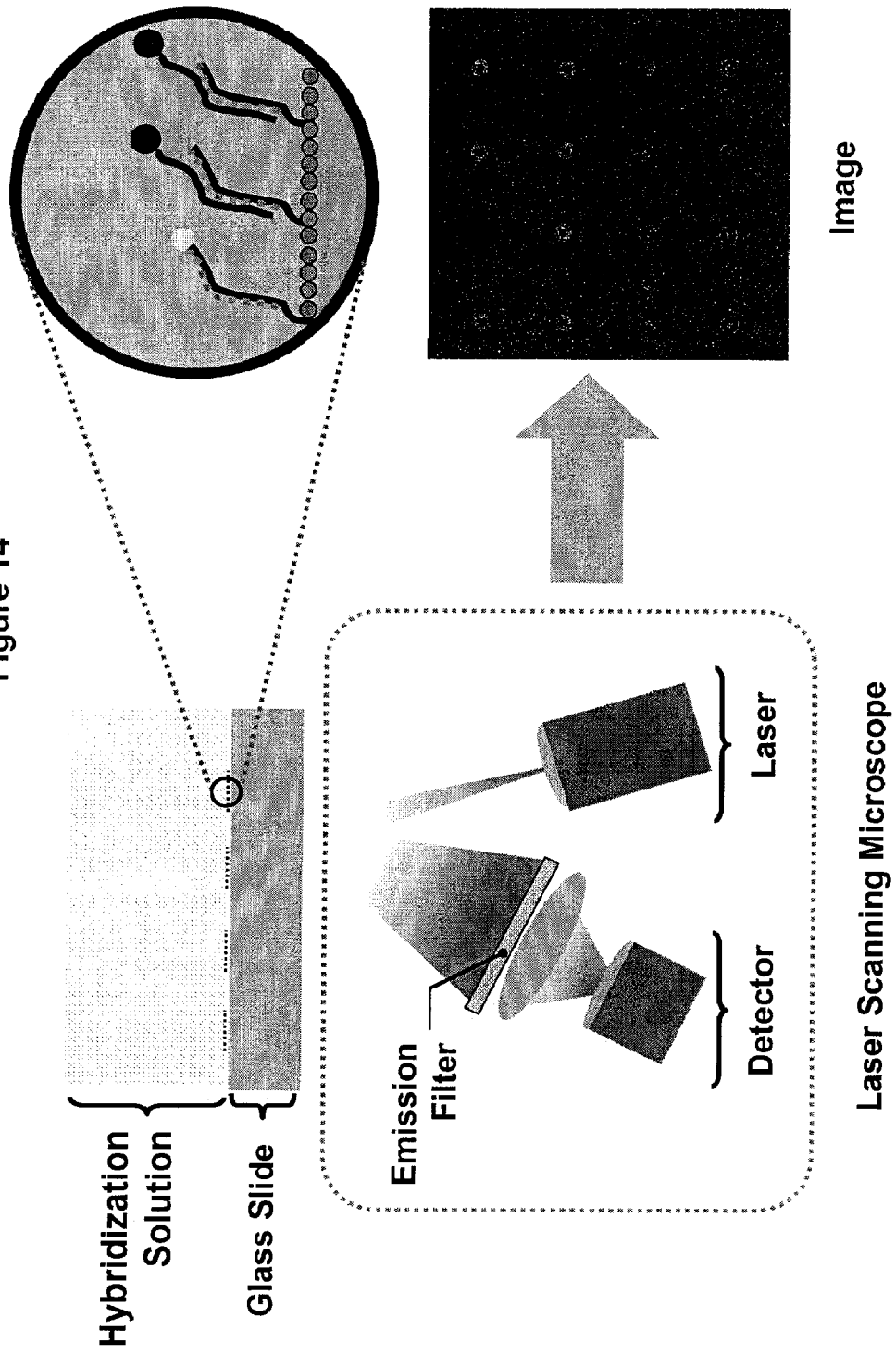
FIG. 14 shows an example of a real-time array system where binding of BHQ2 quencher-labeled cDNA molecules are detected using a fluorescent laser-scanning microscope.

FIG. 14 shows an example of a real-time microarray system where real-time binding of BHQ2 quencher-labeled cDNA molecules are detected using a fluorescent laser-scanning microscope. The substrate in this example is a transparent glass slides and the probes are 25 bp Cy5-labeled oligonucleotides. In this embodiment, the light source (laser) and detector are both located on the back of the substrate.

In some embodiments, the system comprises an instrument that can accept a sub-assembly. The sub assembly comprises a chamber that will hold the fluid volume and the solid substrate having a surface and a plurality of probes. The sub-assembly can be loaded into the instrument in order to monitor the hybridization of amplicons to probes in real time.

In some embodiments, the system comprises: an assay assembly comprising means to engage a microarray and means to perform an assay on a surface of the microarray; and a detector assembly comprising means to detect signals measured at multiple time points from each of a plurality of spots on the microarray during the performance of the assay.

In some embodiments, the means to perform the assay comprise a compartment wherein the surface of the microarray comprises a floor of the compartment and means to deliver reagents and analytes into the compartment. Any method can be used to seal the microarray to the compartment including using adhesives and gaskets to seal the fluid. Any method can be used to deliver reagents and analytes including using syringes, pipettes, tubing, and capillaries.

In some embodiments, the system comprises a means of controlling the temperature. Control of temperature can be important to allow control of binding reaction rates, e.g. by controlling stringency. The temperature can be controlled by controlling the temperature at any place within the system including controlling the temperature of the fluid or the temperature of the solid substrate. Any means can be used for controlling the temperature including resistive heaters, Peltier devices, infrared heaters, fluid or gas flow. The temperatures can be the same or different for solution or substrate or different parts of each. Ideally the temperature is consistently controlled within the binding region. In some embodiments the temperature is controlled to within about 0.01, 0.05, 0.1, 0.5, or 1° C. In some embodiments, for example for a PCR amplification reaction, the temperature is controlled to within 0.1° C.

In some embodiments the system is capable of changing the temperature during the amplification in order to define the phases of the temperature cycles. In some embodiments, the temperature can be rapidly changed during the amplification reaction. In some embodiments, the system is capable of changing the temperature at a rate of temperature change corresponding to a change of 1° C. in less than about 0.01 msec, 0.1 msec, 0.5 msec, 1 msec, 5 msec, 10 msec, 50 msec, 100 msec, 0.5 sec, 1 sec, 10 sec, or 60 sec. In some embodiments, for example for a PCR amplification reaction, the system is capable of changing temperature at a rate of greater than about 5° C., 10° C., or 20° C. per second.

In other embodiments the temperature is changed slowly, gradually ramping the temperature over the course of the binding reaction.

One exemplary embodiment of changing the temperature involves a change in temperature to change the binding stringency and probability. By changing temperature we can alter the stringency and observe the capturing the new capturing process with a new set of capturing probabilities.

In some embodiments, the system is capable of measuring temperature in one or multiple locations in the solution or on the solid substrate. The temperature can be measured by any means including, for example, by thermometer, thermocouple, or thermochromic shift.

In some embodiments the system comprises a feedback loop for temperature control wherein the measured temperature is used as an input to the system in order to more accurately control temperature.

In some embodiments, the system comprises an apparatus to add or remove material from the fluid volume. In some embodiments, the system can add or remove a liquid from the fluid volume. In some embodiments, the system is capable of adding or removing material from the fluid volume in order to change the: concentration, pH, stringency, ionic strength, or to add or remove a competitive binding agent. In some embodiments, the system is capable of changing the volume of the fluid volume.

One exemplary embodiment of adding material to the fluid volume comprises the addition of incubation buffer. By adding the incubation buffer, the concentration of analytes in the system will decrease and therefore the binding probability and kinetic of binding will both decrease. Furthermore, if the reaction has already reached equilibrium, the addition of the buffer will cause the system to move another equilibrium state in time.

Another exemplary embodiment of adding material to the fluid volume is adding a competing binding species. The competing species can be of the same nature of the analyte but in general they are molecules which have affinity to capturing probes. For DNA microarrays for example, the competing species can be synthesized DNA oligo-nucleotides with partially or completely complementary sequence to the capturing probes. In immunoassays, the competing species are antigens.

In some embodiments the system comprises elements to apply an electric potential to the fluid volume to electrically change the stringency of the medium. In some embodiments, the system will provide an electrical stimulus to the capturing region using an electrode structure which is placed in proximity of the capturing region. If the analyte is an electroactive species and/or ion, the electrical stimulus can apply an electrostatic force of the analyte. In certain embodiments, this electrostatic force is adjusted to apply force on the bonds between analyte and capturing probe. If the force is applied to detach the molecule, the affinity of the analyte-probe interaction is reduced and thus the stringency of the bond is evaluated. The electrical stimulus is generally a DC and/or time-varying electrical potentials. Their amplitude can be between 1 mV to 10 V, but typically between 10 mV to 100 mV. The frequency of time-varying signal can be between 1 Hz to 1000 MHz, in some embodiments, the frequency of the time-varying signal is between 100 Hz to 100 kHz. The use of electric potential to control stringency is described in U.S. Pat. No. 6,048,690.

In some embodiments the system comprises a computing system for analyzing the detected signals. In some embodiments, the system is capable of transferring time point data sets to the computing system wherein each time point data set corresponds to detected signal at a time point, and the computing system is capable of analyzing the time point data sets, in order to determine a property related to the analyte and probe. The methods of the current invention can, in some cases, generate more data, sometimes significantly more data than for conventional microarrays. Thus a computer system and software that can store and manipulate the data (for instance, images taken at time points) can be essential components of the system. The data can be analyzed in real-time, as the reaction unfolds, or may be stored for later access.

The information corresponding to detected signal at each time point can be single values such as signal amplitude, or can be more complex information, for instance, where each set of signal information corresponds to an image of a region containing signal intensity values at multiple places within an addressable location.

The property related to analyte and/or probe can be, for example, analyte concentration, binding strength, or competitive binding, and cross-hybridization.

In some embodiments the computing system uses algorithms, for example the algorithms described herein and in U.S. patent application Ser. No. 11/758,621 for determining concentration and/or cross-hybridization.

One aspect of the invention is software for use in performing the calculation of the amount of nucleotide sequences in the sample from the information on the change in optical signal as a function of amplification cycle. The software is capable of, for example, of calculating the CT value, including, for instance, fitting the exponential portion of the curve, determining the background threshold. The software is capable of carrying out these calculations efficiently for large numbers of amplicons and nucleotide sequences.

In some embodiments, the system has software for interfacing with the instrument, for example allowing the user to display information in real-time and allowing for user to interact with the reaction (i.e., add reagents, change the temperature, change the pH, dilution, etc.).

Uses

The methods and systems of the present invention can be used to measure nucleotide sequences in a variety of sample types including cDNA, genomic DNA, RNA, cells, or viruses.

The methods and systems of the present invention are useful for the determination of the presence and amount of multiple nucleotide sequences in a sample. Where the probe and analyte are nucleic acids, the present invention provides methods of expression monitoring and for measuring genetic information. The invention allows for many nucleotide sequences relating to genes, e.g. 10, 100, 1,000, 10,000, 100,000, or more genes to be analyzed at once. The term expression monitoring is used to refer to the determination of levels of expression of particular, typically preselected, genes. For example, amplicons derived from nucleic acid samples such as messenger RNA that reflect the amount of expression of genes are hybridized to the arrays during or after amplification cycles, and the resulting hybridization signal as a function of time provides an indication of the amount of amplicon which can then be used to determine the level of expression of each gene of interest. In some cases, the whole transcriptome can be measured comprising all or a substantial portion of the expression in a cell, or group of cells. In some embodiments the expression of only a few genes, such as 5 to 100 genes is measured, for example, to diagnose a specific condition. In some embodiments, the array has a high degree of probe redundancy (multiple probes per gene) the expression monitoring methods provide accurate measurement and do not require comparison to a reference nucleic acid.

The methods and systems of this invention may be used in a wide variety of circumstances including detection of disease, identification of differential gene expression between two samples (e.g., a pathological as compared to a healthy sample), screening for compositions that upregulate or downregulate the expression of particular genes, and so forth. They can be used for the analysis of genetic DNA including determination of single-nucleotide polymorphisms (SNPs) for genotyping and allele discrimination assays and for the detection of DNA and RNA viruses. The methods and systems of the invention can also be used for the detection of genetically modified organisms (GMO).

The methods and systems of the invention can be used for genetic testing and diagnostics. They can be used for example for newborn screening (e.g. for phenylketonuria or congenital hypothyroidism; diagnostic testing (such as to diagnose or rule out a specific genetic or chromosomal condition or to confirm a diagnosis when a particular condition is suspected based on physical mutations and symptoms); carrier testing: (e.g. to identify people who carry one copy of a gene mutation that, when present in two copies, predictive and presymptomatic testing: (For example, testing for BRCA1 in relation to the risk of breast cancer); forensic testing (e.g. to identify an individual for legal purposes, e.g. to identify crime or catastrophe victims, rule out or implicate a crime suspect, or establish biological relationships between people (for example, paternity); or for research testing (e.g. finding unknown genes, learning how genes work and advancing our understanding of genetic conditions).

EXAMPLES

Example 1

This example demonstrates the use of a real-time microarray to measure the binding of multiple analytes to multiple probes.

Figure 15:
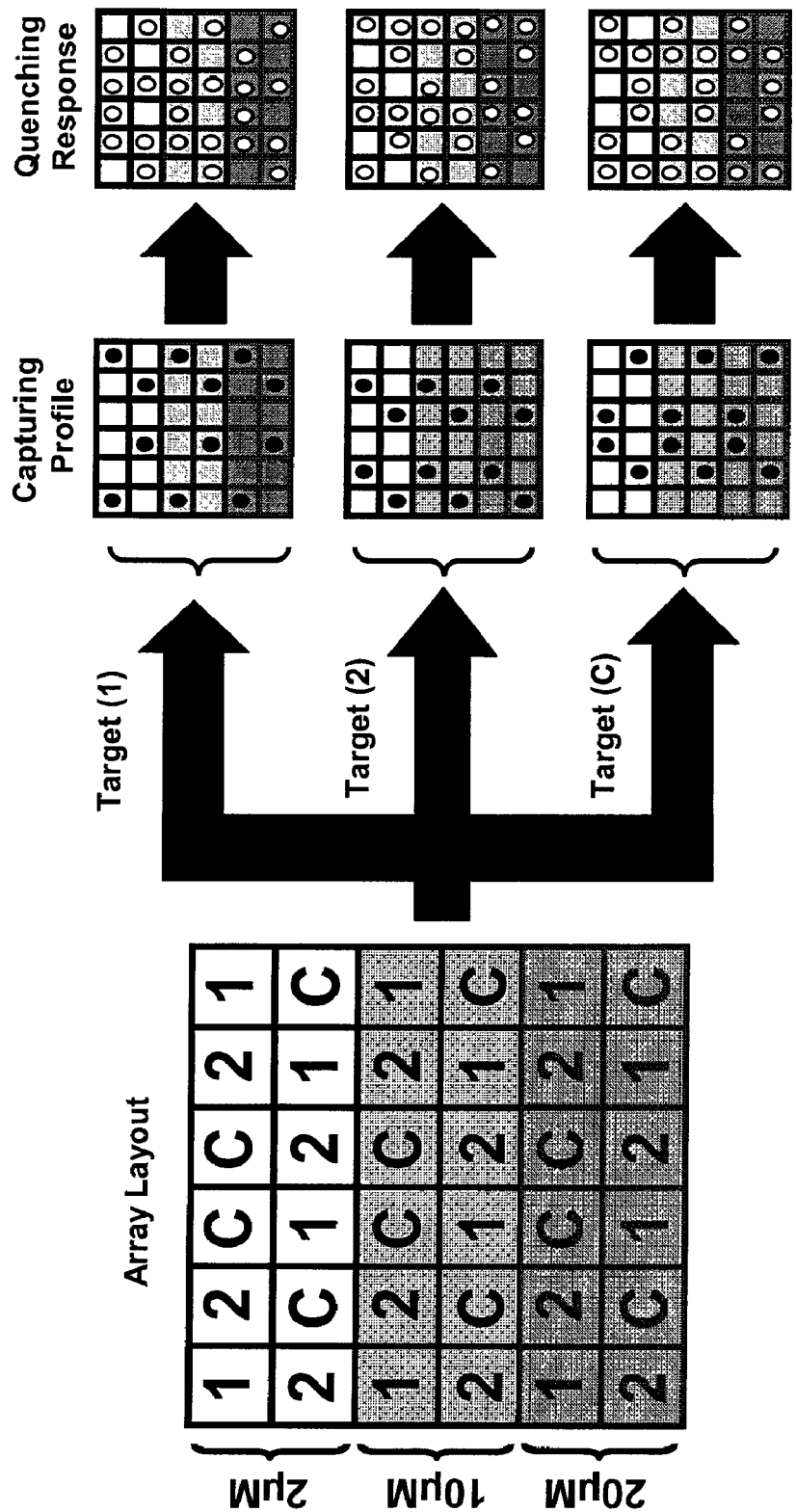
FIG. 15 shows an example of a layout of a 6×6 DNA array.
Figure 16:
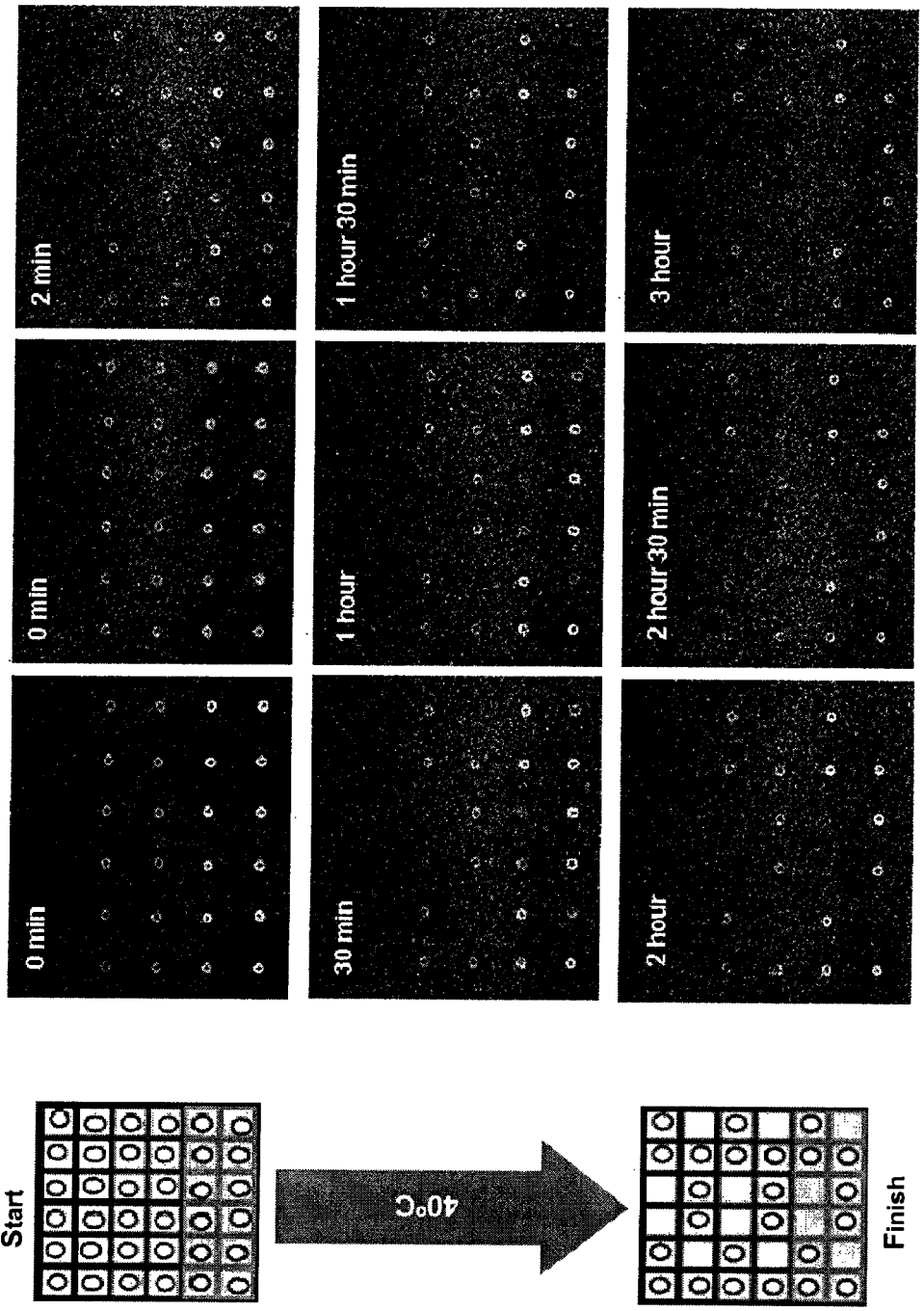
FIG. 16 shows a few samples of real-time measurements in a microarray experiment where control target analytes are added to the system demonstrating the measurement of hybridization in real time.
Figure 17:
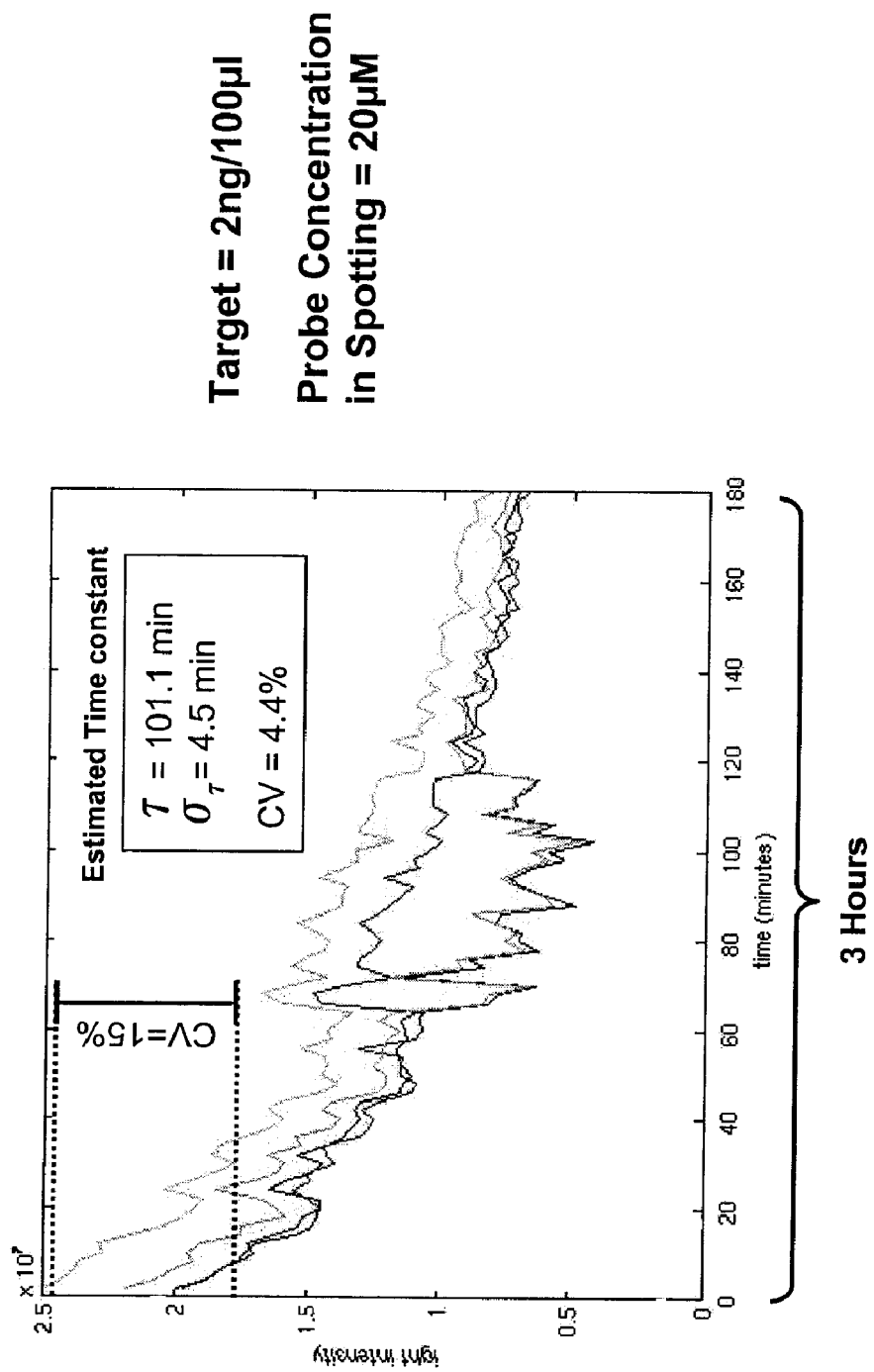
FIGS. 17-20 each show real-time data for 4 different spots with similar oligonucleotide capturing probes. A target DNA analyte is introduced in the system at time zero and quenching (reduction of signal) occurs upon hybridization.
Figure 18:
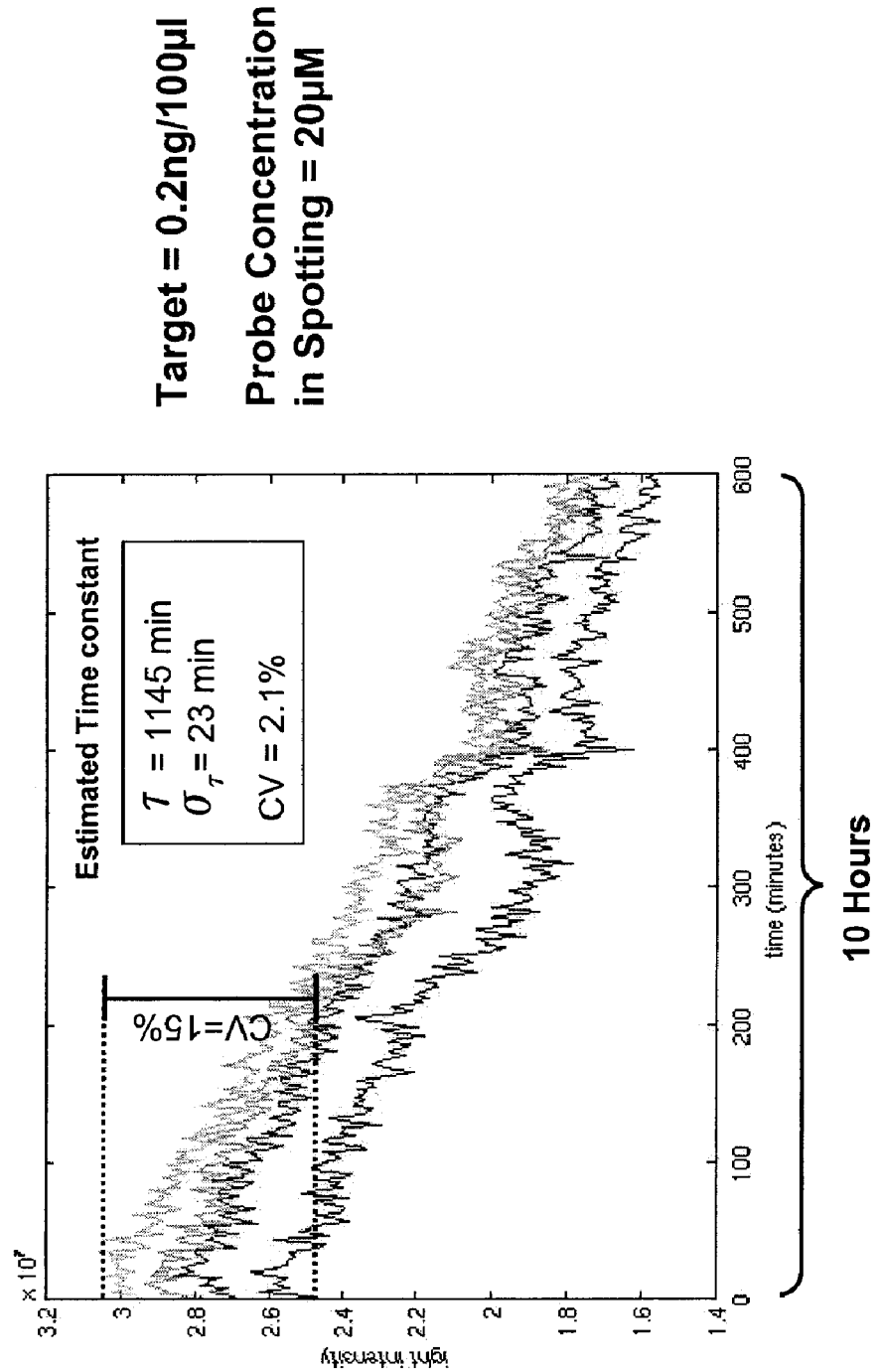
Figure 19:
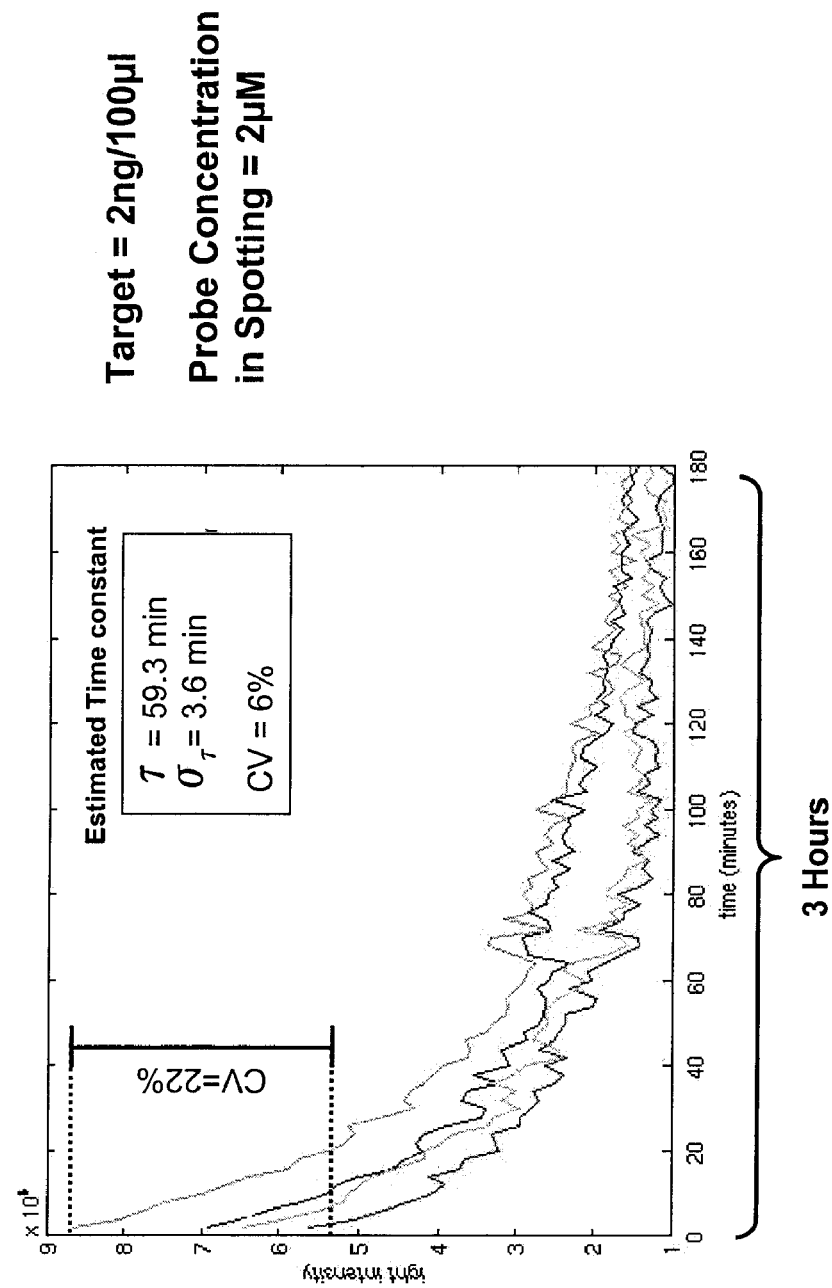
Figure 20:
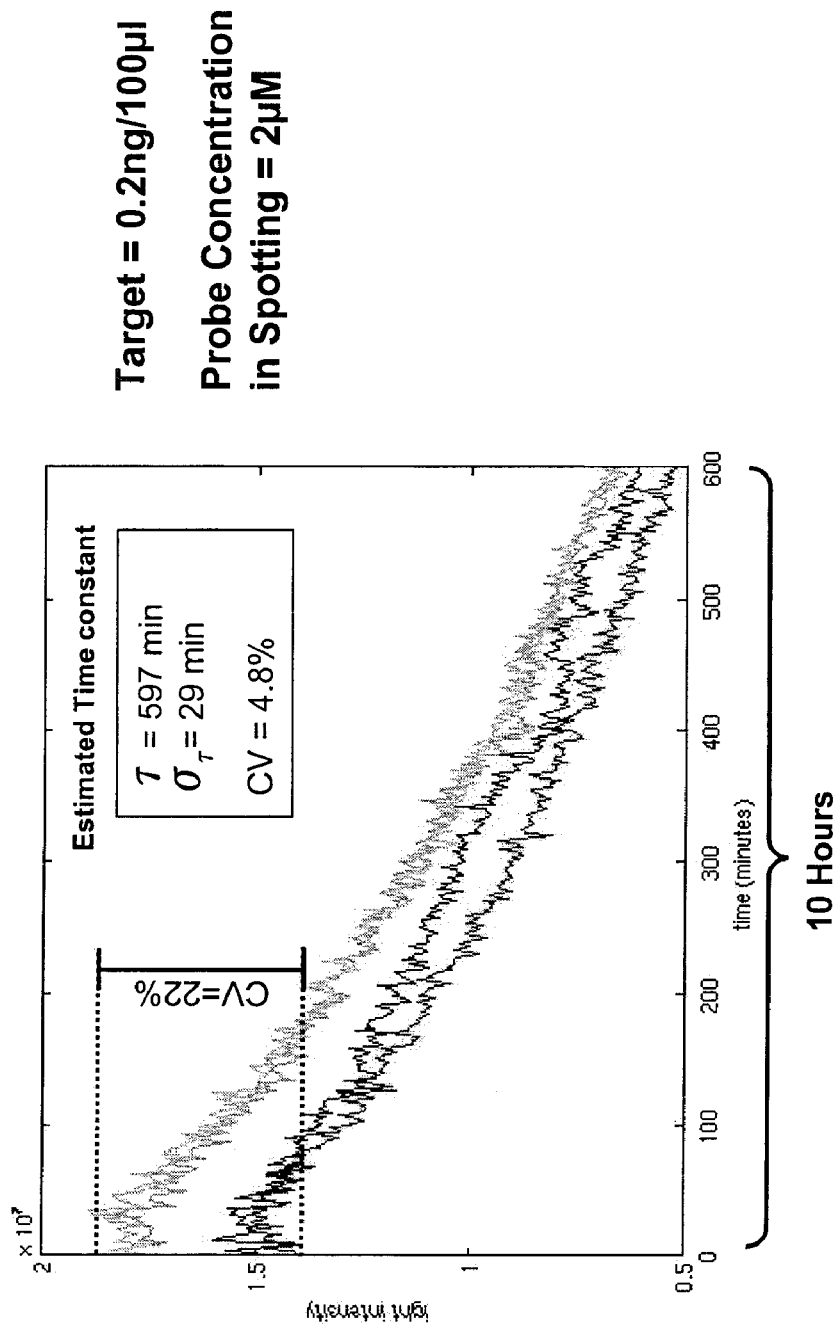

FIG. 15 shows the layout of a 6×6 DNA microarray. Three different DNA probes (1, 2, and Control) with three different concentrations (2 μM, 10 μM, and 20 μM) are spotted and immobilized on the surface as illustrated. The probes contain a single Cy3 fluorescent molecule at the 5' end. The DNA targets in this experiment contain a quencher molecule. The analyte binding in this system results in quenching of fluorescent molecules in certain spots. FIG. 16 shows a few samples of the real-time measurements of the microarray experiment wherein the control targets are added to the system. As illustrated in FIG. 16, the spots are quenched due to analyte binding.

FIGS. 17-20 each show data for 4 different spots with similar oligonucleotide capturing probes. The target DNA analyte is introduced in the system at time zero and quenching (reduction of signal) occurs only when binding happens. For FIG. 17, the light intensity coefficient of variation was about 15%, however the estimated time constant rate from real-time measurements had only 4.4% variations. For FIG. 18 the light intensity coefficient of variation was about 15%, however the estimated time constant rate from real-time measurements had only 2.1% variations. For FIG. 19 the light intensity coefficient of variation was about 22%, however the estimated time constant rate from real-time measurements had only 6% variations. For FIG. 20 the light intensity coefficient of variation was about 22%, however the estimated time constant rate from real-time measurements had only a 4.8% variation.

Figure 21:
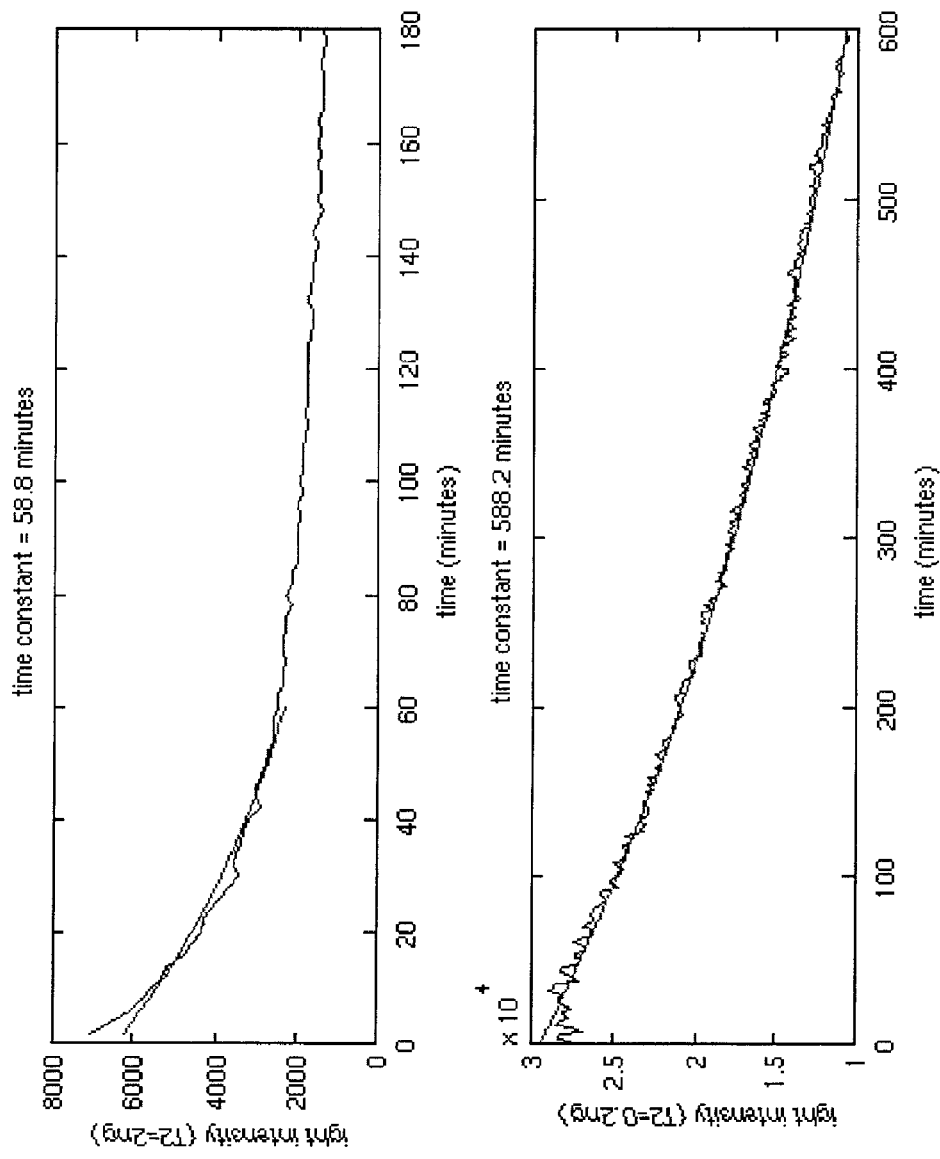
FIG. 21 shows the signals measured during two real-time experiments wherein a target analyte (target 2) is applied to the microarray, at 2 ng and at 0.2 ng.

In FIG. 21, the signals measured during two real-time experiments wherein target 2 is applied to the microarray, first at 2 ng and then at 0.2 ng, are shown. The measured light intensities at the corresponding probe spots decay over time as the targets to the probes bind and the quenchers come in close proximity to the fluorescent labels attached to the end of the probes. The rate of the decay, which can be estimated by a curve fitting technique, is proportional to the amount of the target present. The time constant of the measured process is defined as the inverse of the rate of decay. The ratio of the time constants of the two processes is 10, which is precisely the ratio of the amounts of targets applied in the two experiments.

Example 2

This example provides a derivation of an algorithm, and the use of the algorithm to determine analyte concentration, such as amplicon concentration, from a real-time binding data. The derivation proceeds as follows:

Assume that the hybridization process starts at t=0, and consider discrete time intervals of the length Δt. Consider the change in the number of bound target molecules during the time interval (iΔt, (i+1)Δt). We can write $$n_b(i+1)-n_b(i)=[n_t-n_b(i)]p_b(i)\Delta t-n_b(i)p_r(i)\Delta t,$$

where $n_t$ denotes the total number of target molecules, $n_b(i)$ and $n_b(i+1)$ are the numbers of bound target molecules at t=iΔt and t=(i+1)Δt, respectively, and where $p_b(i)$ and $p_r(i)$ denote the probabilities of a target molecule binding to and releasing from a capturing probe during the $i^{th}$ time interval, respectively. Hence, $$\frac{n_b(i+1)-n_b(i)}{\Delta t}=[n_t-n_b(i)]p_b(i)-n_b(i)p_r(i). \quad (1)$$

It is reasonable to assume that the probability of the target release does not change between time intervals, i.e., $p_r(i)=p_r$, for all i. On the other hand, the probability of forming a target-probe pair depends on the availability of the probes on the surface of the array. If we denote the number of probes in a spot by $n_p$, then we can model this probability as $$p_b(i)=\left(1-\frac{n_b(i)}{n_p}\right)\cdot p_b=\frac{n_p-n_b(i)}{n_p}p_b, \quad (2)$$

where $p_b$ denotes the probability of forming a target-probe pair assuming an unlimited abundance of probes.

By combining (1) and (2) and letting Δt→0, we arrive to $$\frac{dn_b}{dt}=(n_t-n_b)\frac{n_p-n_b}{n_p}p_p-n_b p_r \quad (3)$$
$$=n_t p_b-\left[\left(1+\frac{n_t}{n_p}\right)p_b+p_r\right]n_b+\frac{p_b}{n_p}n_b^2$$

Note that in (3), only $n_b=n_b(t)$, while all other quantities are constant parameters, albeit unknown. Before proceeding any further, we will find it useful to denote $$\alpha=\left(1+\frac{n_t}{n_p}\right)p_b+p_r, \beta=n_t p_b, \gamma=\frac{p_b}{n_p}. \quad (4)$$

Clearly, from (4), $$p_b=\frac{\beta}{n_t}, n_p=\frac{p_b}{\gamma}, p_r=\alpha-\left(1+\frac{n_t}{n_p}\right)p_b.$$

Using (4), we can write (3) as $$\frac{dn_b}{dt}=\beta-\alpha n_b+\gamma n_b^2=\gamma(n_b-\lambda_1)(n_b-\lambda_2), \quad (5)$$

where $\lambda_1$ and $\lambda_2$ are introduced for convenience and denote the roots of $$\beta-\alpha n_b+\gamma n_b^2=0.$$

Note that $\gamma=\beta/(\lambda_1\lambda_2)$. The solution to (5) is found as $$n_b(t)=\lambda_1+\frac{\lambda_1(\lambda_1-\lambda_2)}{\lambda_2 e^{\beta\left(\frac{1}{\lambda_1}-\frac{1}{\lambda_2}\right)t}-\lambda_1}. \quad (6)$$

We should point out that (3) describes the change in the amount of target molecules, $n_b$, captured by the probes in a single probe spot of the microarray. Similar equations, possibly with different values of the parameters $n_p$, $n_t$, $p_b$, and $p_r$, hold for other spots and other targets.

Estimating Parameters of the Model

The following is an outline of a procedure for estimation of the parameters. Ultimately, by observing the hybridization process, we would like to obtain $n_t$, $n_p$, $p_b$, and $p_r$. However, we do not always have direct access to $n_b(t)$ in (6), but rather to $y_b(t)=kn_b(t)$, where k denotes a transduction coefficient. In particular, we observe $$y_b(t) = \lambda_1^* + \frac{\lambda_1^*(\lambda_1^* - \lambda_2^*)}{\lambda_2^* e^{\beta\left(\frac{1}{\lambda_1^*} - \frac{1}{\lambda_2^*}\right)} - \lambda_1^*}, \quad (7)$$

where $\lambda_1^* = k\lambda_1$, $\lambda_2^* = k\lambda_2$, and $\beta^* = k\beta$.

For convenience, we also introduce $$\gamma^* = \frac{\beta^*}{\lambda_1^* \lambda_2^*} = \frac{\gamma}{k}, \quad \alpha^* = \gamma^*(\lambda_1^* + \lambda_2^*) = \alpha. \quad (8)$$

From (5), it follows that $$\beta^* = \frac{dy_b}{dt}\bigg|_{t=0}. \quad (9)$$

Assume, without a loss of generality, that $\lambda_1^*$ is the smaller and $\lambda_2^*$ the larger of the two, i.e., $\lambda_1^* = \min(\lambda_1, \lambda_2)$, and $\lambda_2^* = \max(\lambda_1, \lambda_2)$. From (7), we find the steady-state of $y_b(t)$, $$\lambda_1^* = \lim y_b(t), t \to \infty. \quad (10)$$

So, from (9) and (10) we can determine $\beta^*$ and $\lambda_1^*$, two out of the three parameters in (7). To find the remaining one, $\lambda_2^*$, one needs to fit the curve (7) to the experimental data.

Having determined $\beta^*$, $\lambda_1$, and $\lambda_2^*$, we use (8) to obtain $\alpha^*$ and $\gamma^*$. Then, we should use (4) to obtain $p_b$, $p_r$, $n_p$, and $n_t$ from $\alpha^*$, $\beta^*$, and $\gamma^*$. However, (4) gives us only 3 equations while there are 4 unknowns that need to be determined. Therefore, we need at least 2 different experiments to find all of the desired parameters. Assume that the arrays and the conditions in the two experiments are the same except for the target amounts applied. Denote the target amounts by $n_t$, and $n_t$; on the other hand, $p_b$ and $p_r$ remain the same in the two experiments. Let the first experiment yield $\alpha_1^*$, $\beta_1^*$, and $\gamma_1^*$, and the second one yield $\alpha_2^*$, $\beta_2^*$, and $\gamma_2^*$ (we note that $\gamma_1^* \cdot \gamma_2^*$). Then it can be shown that $$p_b = \frac{\beta_1^* \gamma_1^* - \beta_2^* \gamma_2^*}{\alpha_1^* - \alpha_2^*}, \quad (11)$$

and $$p_r = \alpha_1^* - p_b - \frac{\beta_1^* \gamma_1^*}{p_b}. \quad (12)$$

Moreover, $$n_p = \frac{p_b}{k\gamma_1^*}, \quad (13)$$

and $$n_{t_1} = \frac{\beta_1^* \gamma_1^*}{p_b^2} n_p, \quad n_{t_2} = \frac{\beta_2^* \gamma_2^*}{p_b^2} n_p. \quad (14)$$

We note that quantities (13)-(14) are known within the transduction coefficient k, where $k = y_b(0)/n_p$. To find k and thus unambiguously quantify $n_p$, $nt_{t1}$, and $n_{t2}$, we need to perform a calibration experiment (i.e., an experiment with a known amount of targets $n_t$).

Figure 22:
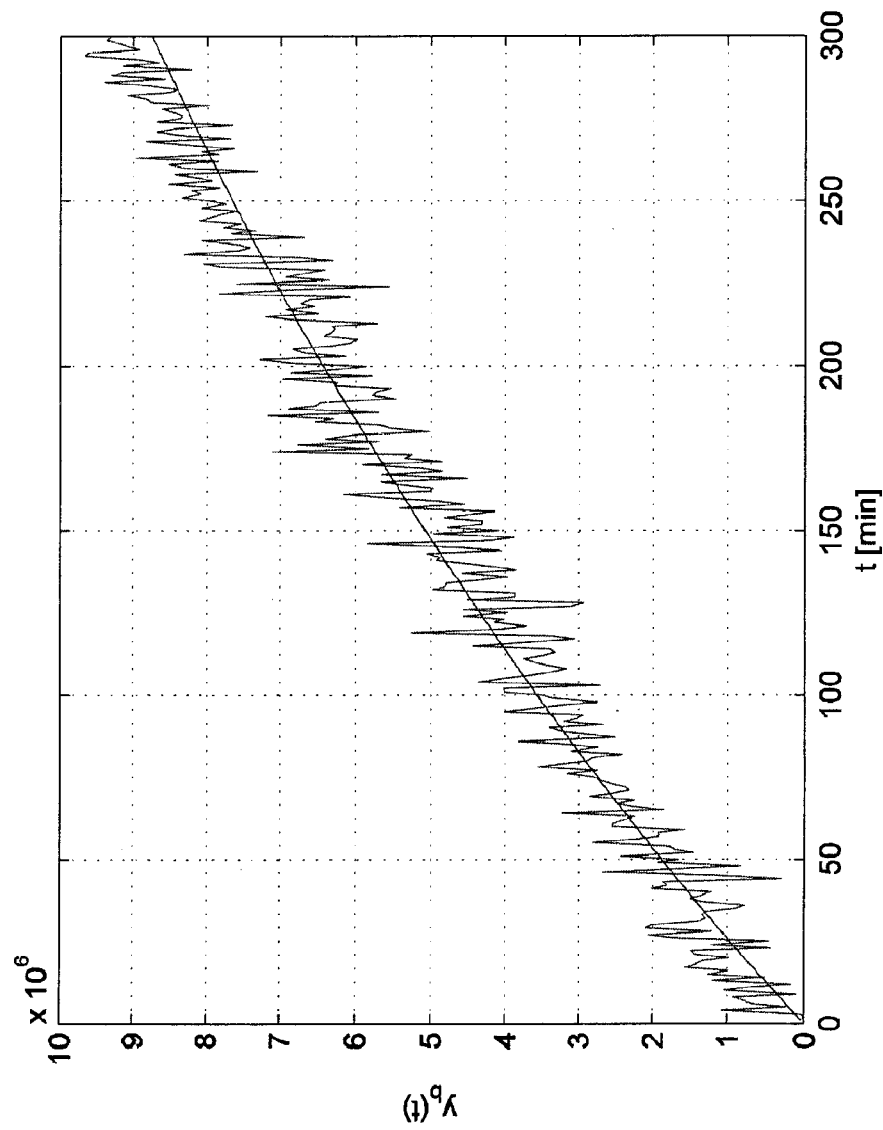
FIG. 22 shows the signal measured in a real-time array, and the fit of the data to an algorithm for determining amount of analyte present in the fluid, where 80 ng of the target is applied to the array in 50 µl.
Figure 23:
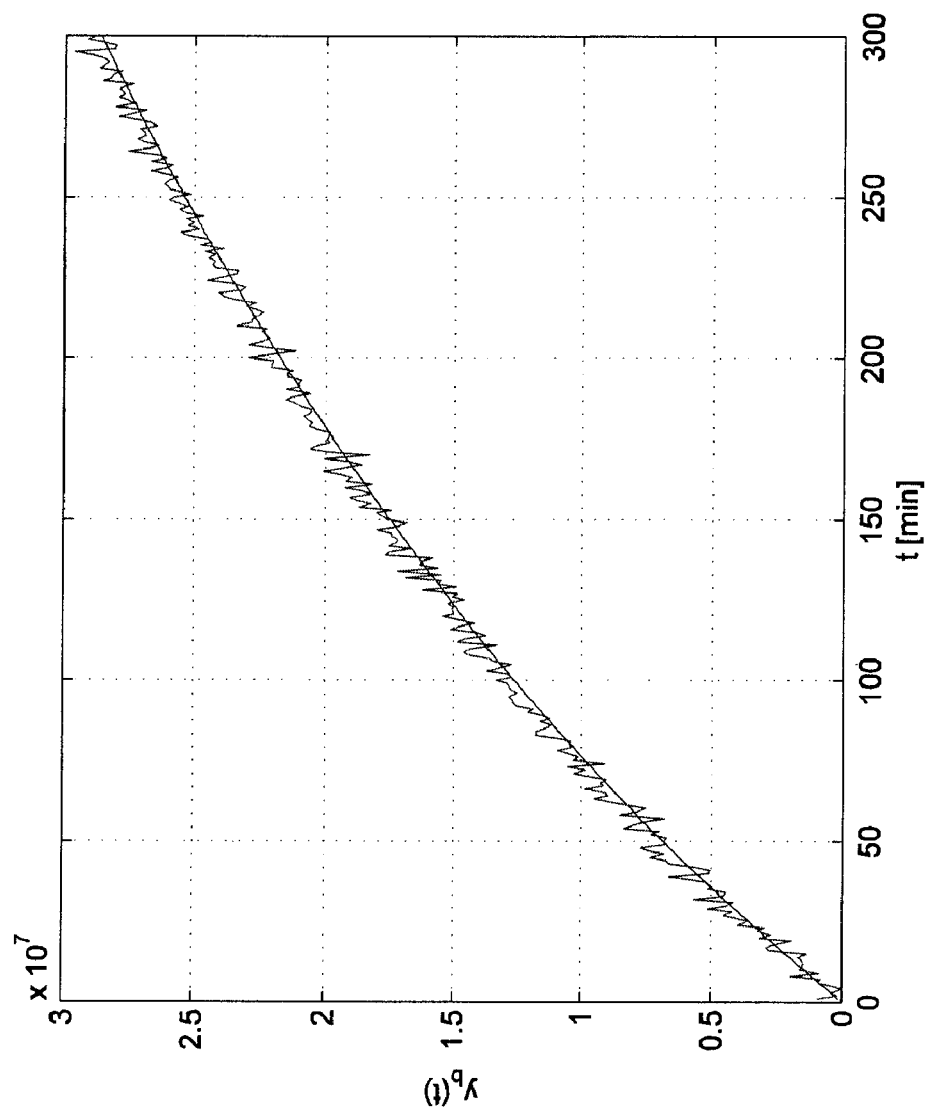
FIG. 23 shows signal measured in a real-time array, and the fit of the data to an algorithm for determining amount of analyte present in the fluid, where 16 ng of the target is applied to the array in 50 µl.

Experiments were performed that were designed to test the validity of the proposed model and demonstrate the parameter estimation procedure. To this end, two DNA microarray experiments are performed. The custom 8-by-9 arrays contain 25mer probes printed in 3 different probe densities. The targets are Ambion mRNA Spikes, applied to the arrays with different concentrations. The concentrations used in the two experiments are 80 ng/50 μl and 16 ng/50 μl. The signal measured in the first experiment, where 80 ng of the target is applied to the array, is shown in FIG. 22. The smooth line shown in the same figure represents the fit obtained according to (7). In the second experiment, 16 ng of the target is applied to the array. The measured signal, and the corresponding fit obtained according to (7), are both shown in FIG. 23.

Applying (11)-(14), we obtain $p_b = 1.9 \times 10^{-3}$, $p_r = 2.99 \times 10^{-5}$.

Furthermore, we find that $$n_{t1}/n_{t2} = \beta_1^*/\beta_2^* = 3.75. \quad (15)$$

Note that the above ratio is relatively close to its true value, 80/16=5. Finally, assuming that one of the experiments is used for calibration, we find that the value of the transduction coefficient is $k=4.1 \times 10^{-4}$, and that the number of probe molecules in the observed probe spots is $n_p = 1.6 \times 10^{-11}$.

What is claimed is:

1. A method comprising:
   (a) performing a nucleic acid amplification on two or more nucleotide sequences to produce two or more amplicons in a fluid;
   (b) providing an array comprising a solid surface with a plurality of nucleic acid probes at independently addressable locations, said array configured to contact said fluid; and
   (c) measuring the hybridization of the amplicons to the two or more nucleic acid probes while the fluid is in contact with the array to obtain an amplicon hybridization measurement wherein the amplicons comprise a quencher.

2. The method of claim 1 wherein primers are used to create the amplicons and the primers comprise a quencher.

3. The method of claim 2 wherein one of the primers in a primer pair comprises a quencher.

4. The method of claim 2 wherein both of the primers in a primer pair comprise a quencher.

5. The method of claim 1 wherein quenchers are incorporated into the amplicons as they are formed.

6. The method of claim 5 wherein d-NTP's are used to make the amplicons, and one or more of the d-NTP's used to make the amplicon comprises a quencher.

7. The method of claim 1 wherein the amplicon hybridization measurement is performed by measuring fluorescence from fluorescent moieties attached to the solid surface.

8. The method of claim 7, wherein the fluorescent moieties are covalently attached to the nucleic acid probes.

9. The method of claim 7, wherein the fluorescent moieties are attached to the substrate and are not covalently attached to the nucleic acid probes.

10. The method of claim 7 wherein the amplicons comprise quenchers, and the measuring of hybridization is performed by measuring a decrease in fluorescence due to hybridization of amplicons to the nucleic acid probes.

11. A method comprising:
 (a) providing an array comprising a solid support having a surface and a plurality of different probes, the different probes immobilized to the surface at different addressable locations, each addressable location comprising a fluorescent moiety;
 (b) performing PCR amplification on a sample comprising a plurality of nucleotide sequences; the PCR amplification carried out in a fluid, wherein:(i) a PCR primer for each nucleic acid sequence comprises a quencher; and (ii) the fluid is in contact with the probes, whereby amplified molecules can hybridize with probes, thereby quenching signal from the fluorescent moiety;
 (c) detecting the signals from the fluorescent moieties at the addressable locations over time;
 (d) using the signals detected over time to determine the amount of amplified molecules in the fluid; and
 (e) using the amount of amplified molecules in the fluid to determine the amount of the nucleotide sequences in the sample.

12. The method of claim 11 wherein the determining of the amount of amplified molecules is performed during or after multiple temperature cycles of the PCR amplification.

13. The method of claim 11 wherein more than one PCR primer for each nucleic acid sequence comprises a quencher.

14. The method of claim 11 wherein the detecting of the signals from the fluorescent moieties at the addressable locations over time comprises measuring the rate of hybridization of the amplified molecules with the probes.

15. The method of claim 11 wherein the sample comprises messenger RNA or nucleotide sequences derived from messenger RNA, and the determination of the amount of nucleic acid sequence in the sample is used to determine the level of gene expression in a cell or group of cells from which the sample was derived.

16. The method of claim 11 wherein the sample comprises genomic DNA or nucleotide sequences derived from genomic DNA, and the determination of the amount of nucleic acid sequence in the sample is used to determine the genetic makeup of a cell or group of cells from which the sample was derived.

17. The method of claim 11 wherein two or more PCR primers corresponding to two or more different nucleotide sequences have different quenchers.

18. The method of claim 11 wherein two or more different addressable locations comprise different fluorescent moieties.

19. The method of claim 17 or 18 wherein the different quenchers and/or different fluorescent moieties are used to determine cross-hybridization.

20. A diagnostic test for determining the state of health of an individual comprising performing the method of claim 11 on a sample from such individual.

* * * * *